(12) United States Patent
Ramasubramanian et al.

(10) Patent No.: US 8,566,121 B2
(45) Date of Patent: Oct. 22, 2013

(54) PERSONALIZED MEDICAL ADHERENCE MANAGEMENT SYSTEM

(76) Inventors: Narayanan Ramasubramanian, Fremont, CA (US); Anand Subra, Plymouth, MN (US)

(*) Notice: Subject to any disclaimer, the term of this patent is extended or adjusted under 35 U.S.C. 154(b) by 1141 days.

(21) Appl. No.: 12/101,063

(22) Filed: Apr. 10, 2008

(65) Prior Publication Data

US 2008/0201174 A1 Aug. 21, 2008

Related U.S. Application Data

(63) Continuation-in-part of application No. 11/511,703, filed on Aug. 28, 2006, now abandoned.

(60) Provisional application No. 60/712,751, filed on Aug. 29, 2005, provisional application No. 60/923,124, filed on Apr. 12, 2007.

(51) Int. Cl.
*G06Q 10/00* (2012.01)
*G06Q 50/00* (2012.01)

(52) U.S. Cl.
USPC .................................................. 705/3; 705/2

(58) Field of Classification Search
USPC ............................................................ 705/3
See application file for complete search history.

(56) References Cited

U.S. PATENT DOCUMENTS

| | | | |
|---|---|---|---|
| 5,642,731 A | 7/1997 | Kehr | |
| 5,832,488 A | 11/1998 | Eberhardt | |
| 6,151,586 A * | 11/2000 | Brown | 705/2 |
| 6,234,964 B1 | 5/2001 | Iliff | |
| 6,305,377 B1 | 10/2001 | Portwood et al. | |
| 6,415,295 B1 | 7/2002 | Feinberg | |
| 6,770,029 B2 | 8/2004 | Iliff | |
| 6,974,328 B2 | 12/2005 | Aspe et al. | |
| 7,577,573 B2 * | 8/2009 | Janas et al. | 705/2 |
| 2002/0169635 A1 * | 11/2002 | Shillingburg | 705/2 |
| 2003/0014284 A1 | 1/2003 | Jones | |
| 2005/0108051 A1 * | 5/2005 | Weinstein | 705/2 |
| 2005/0165626 A1 | 7/2005 | Karpf | |
| 2005/0283385 A1 * | 12/2005 | Hunkeler et al. | 705/2 |
| 2006/0020175 A1 | 1/2006 | Berry et al. | |

OTHER PUBLICATIONS

U.S. Appl. No. 11/511,703, filed Aug. 28, 2006 Non-Final OA, Jun. 12, 2008.

(Continued)

*Primary Examiner* — Hiep V Nguyen
(74) *Attorney, Agent, or Firm* — Hickman Palermo Truong Becker Bingham Wong LLP

(57) ABSTRACT

Techniques and systems are described hereafter for reducing medical non-adherence by (1) developing the adherence-profile of a member, (2) using the profile to automatically generate a set of interventions, (3) categorizing, prioritizing and selecting the interventions, (4) incorporating the selected interventions into a personalized member user interface page, (5) serving the selected interventions to the member at the appropriate times via multiple channels, (6) observing and measuring member responses, (7) recording member responses in a database and analyzing the responses, (8) adapting the interventions, based on the analysis, to keep the member actively engaged, (9) escalating the interventions if the member response is inadequate, (10) updating the member's adherence profile based on analysis of the database, (11) providing member reports to authorized parties for purposes of paying member incentives, predicting member's utilization of high-cost healthcare services, etc., and (12) providing aggregate de-identified reports for purposes of predicting future risk reserve set asides, drug production and supply chain replenishment requirements.

26 Claims, 37 Drawing Sheets

(56) References Cited

OTHER PUBLICATIONS

Medication Compliance Stats (Ref. 4) 25 pages.

"Healthpages.com" dowloaded Nov. 16, 2006 from the Internet < http://www.heathpages.com/ > (Ref. 5) 2 pages.

Prochaska et al., "Detailed Overview of the Transtheoretical Model" (Ref. 6) 12 pages.

"The Burden of Chronic Diseases and their Risk Factors" (198 pages).

"World Health Statistics 2005" (Ref. 1 CDC, WHO, ADA, etc. disease prevalence stats) 59 pages.

"Loss Ratios and Heath Coverages (Nov. 1998) Loss Ratio Work Group" (Ref. 2 definition of loss ratio) 25 pages.

"The Hidden Epidemic Finding a Cure for Unfilled Prescriptions and Missed Doses" (Dec. 2003) The Boston Consulting Group (Ref. 3 medication compliance BCG study) (8 pages).

Medication Compliance Stats (Ref. 4) retrieved Jan. 16, 2007, 25 pages.

"Healthpages.com" dowloaded Nov. 16, 2006 from the Internet < http: //www.heathpages.com/> (Ref. 5) 2 pages.

Prochaska et al., "Detailed Overview of the Transtheoretical Model" (Jan. 2001) (Ref. 6) 12 pages.

CDC Morbidity and Mortality Weekly Report (Aug. 2003) (Ref. 7 CDC unscrreened stats) 84 pages.

"National Center for Health Statistics" downloaded Nov. 16, 2006 from the Internet < http://www.cdc.gov/nchs/nhis.htm > (Ref. 8) 3 pages.

"Etiquette & Effectiveness: How Should a Smart Home Interact", Honeywell Laboratories, 2003 (Ref. 9) 14 pages.

"The Burden of Chronic Diseases and their Risk Factors" (2004) (198 pages).

\* cited by examiner

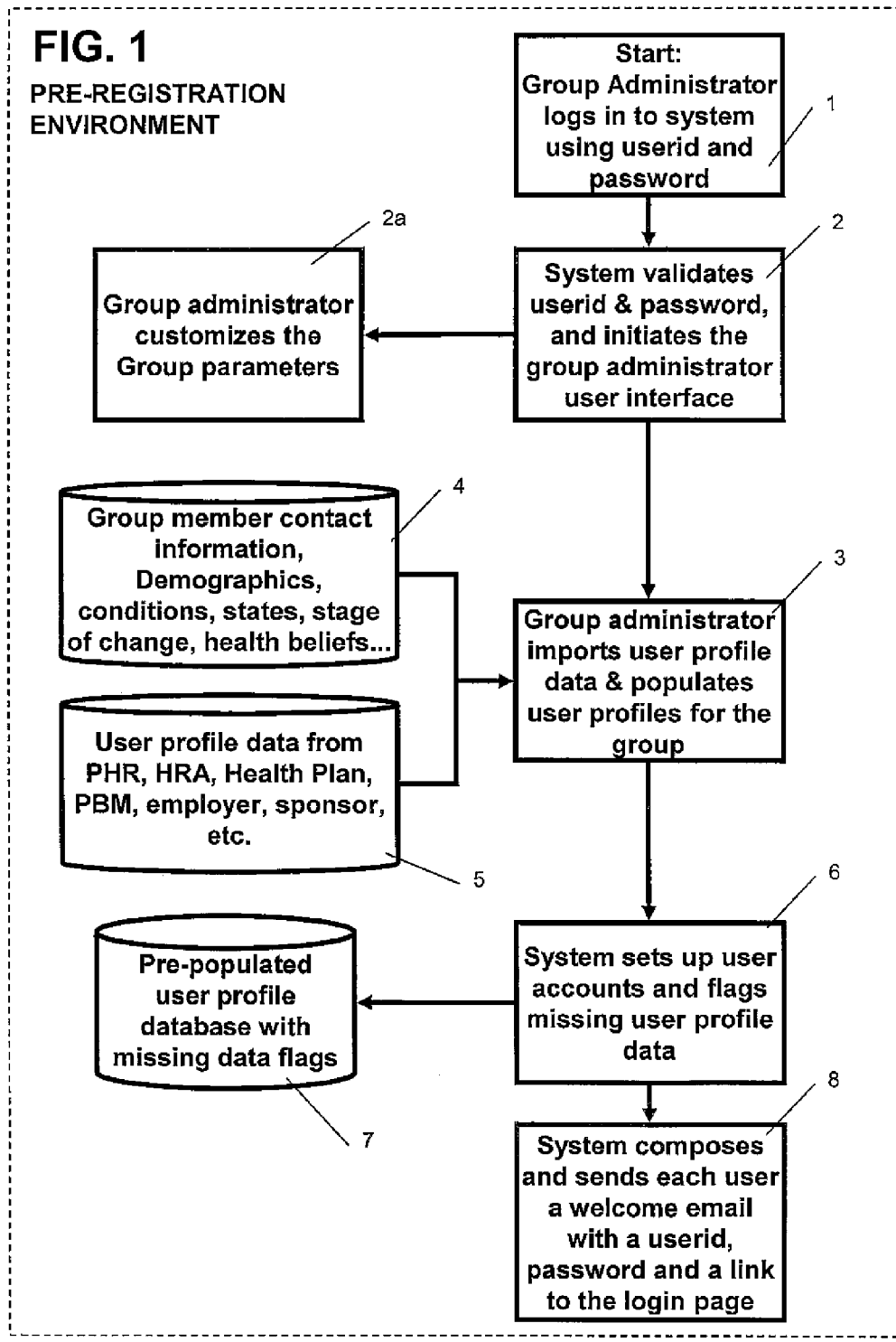

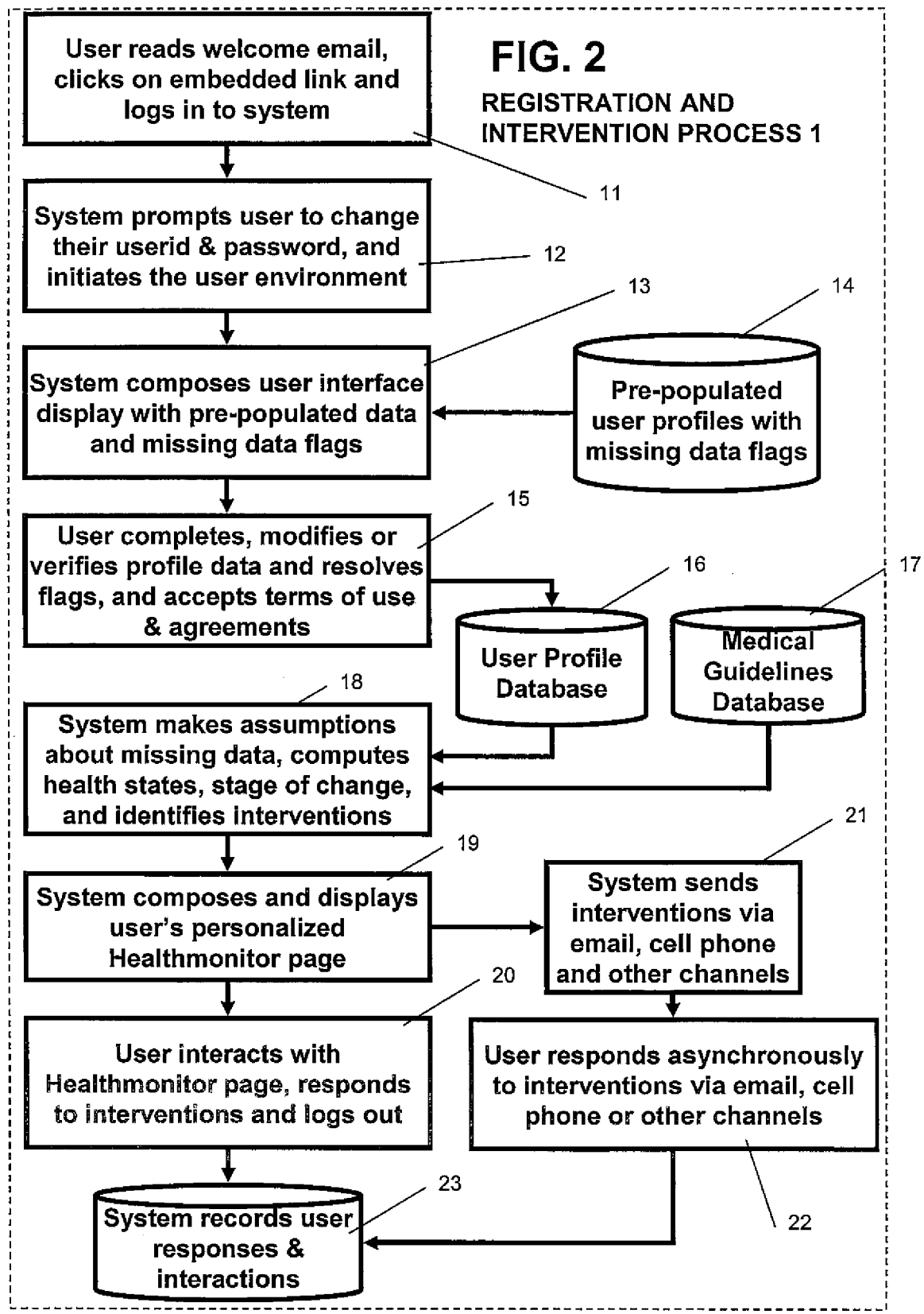

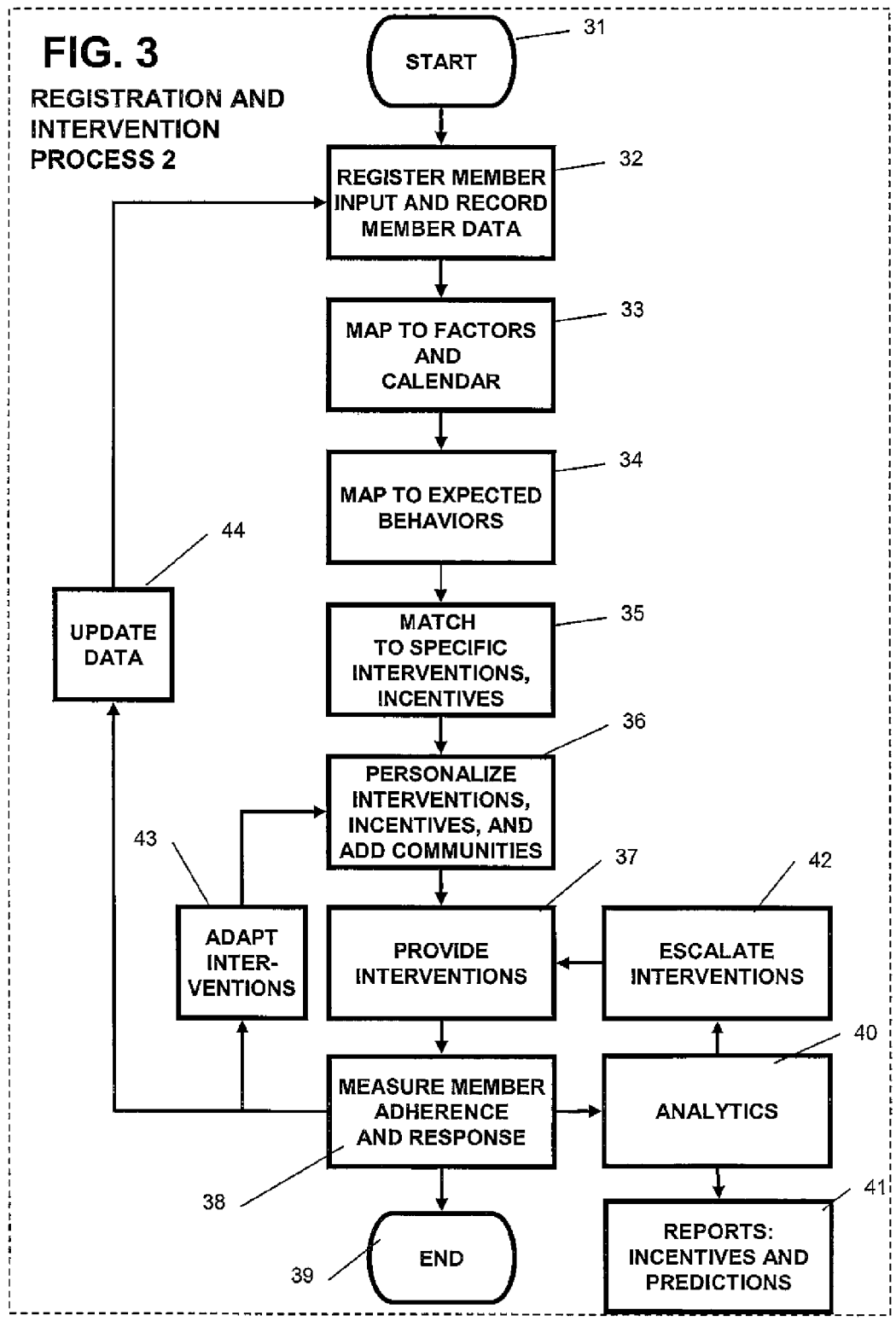

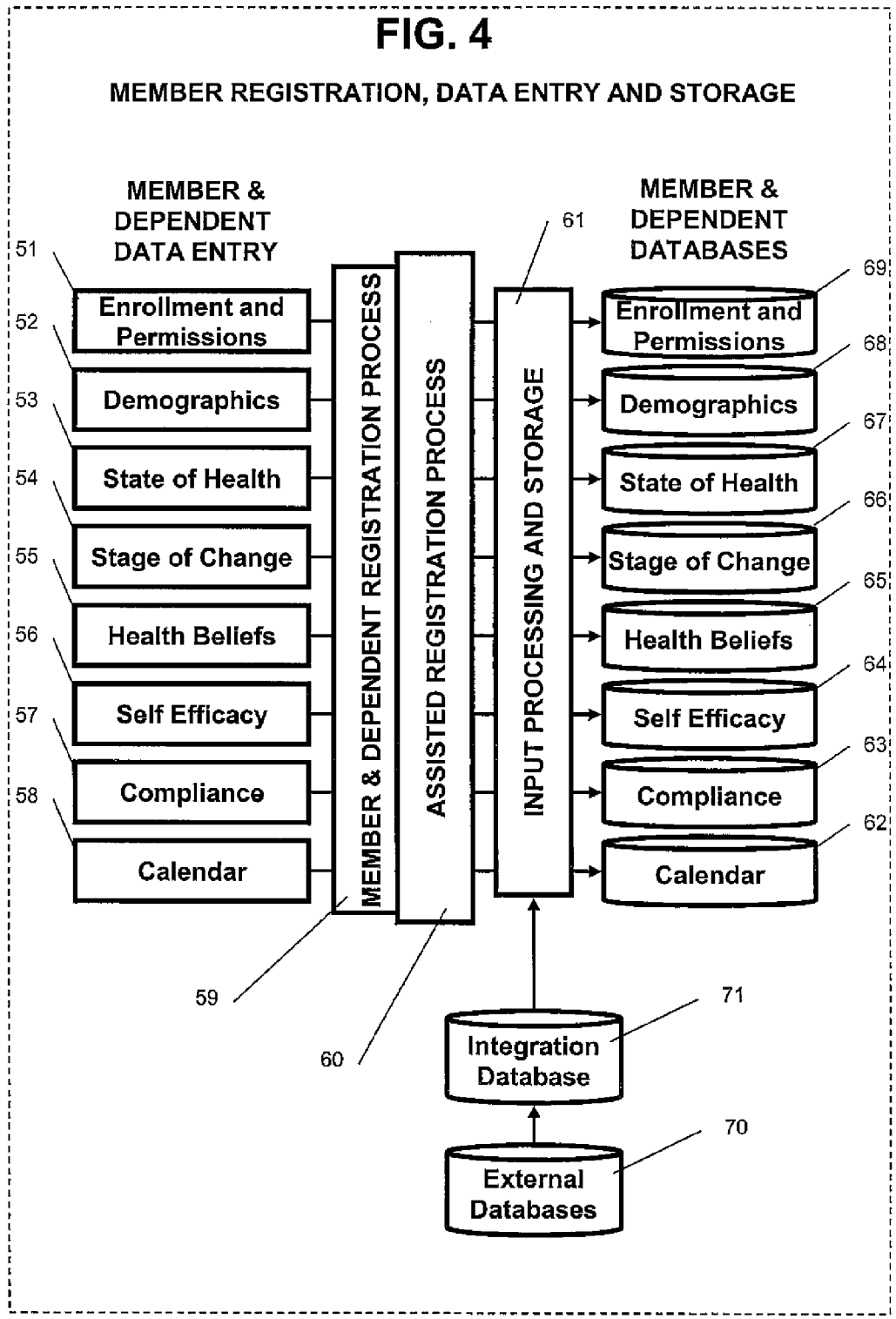

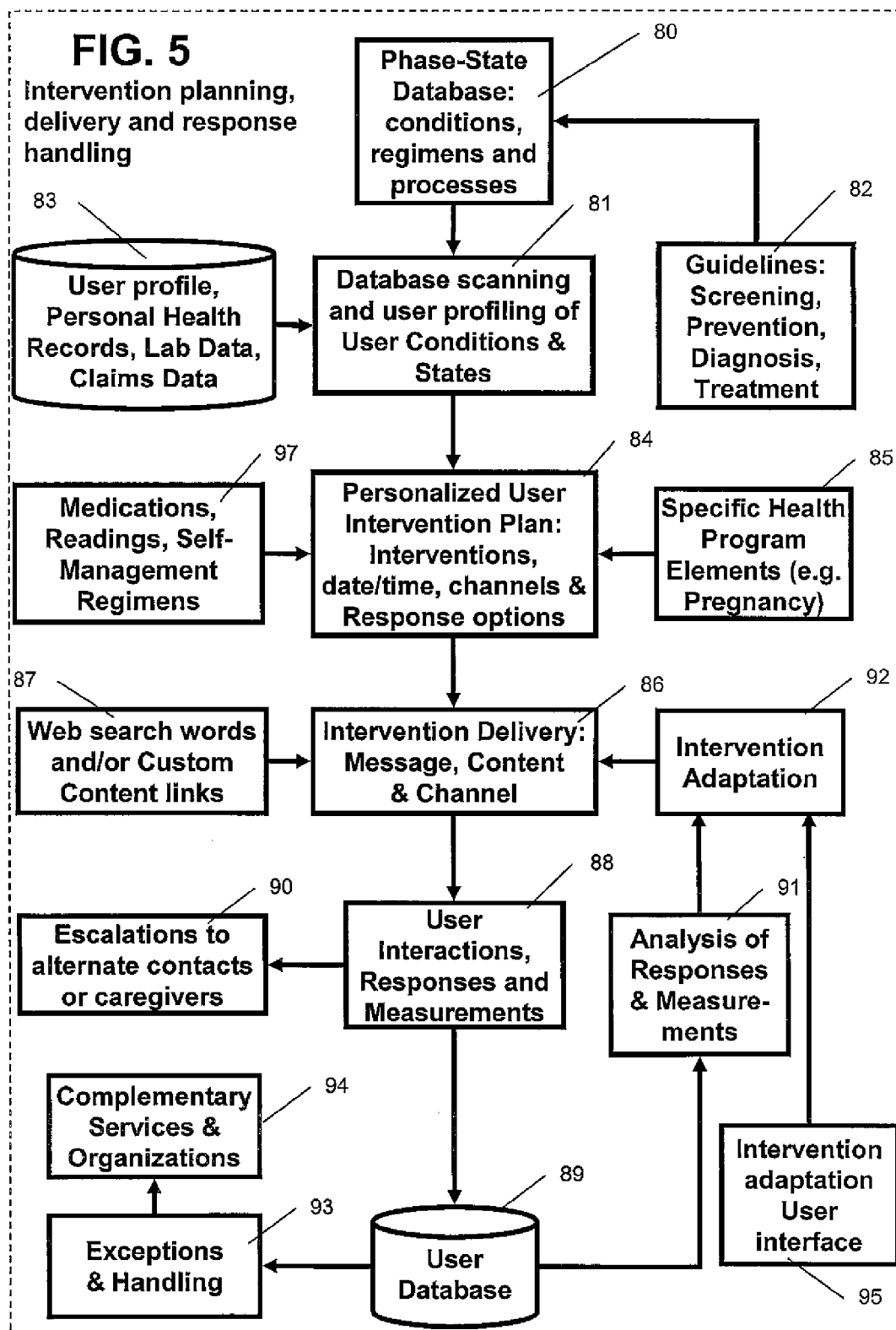

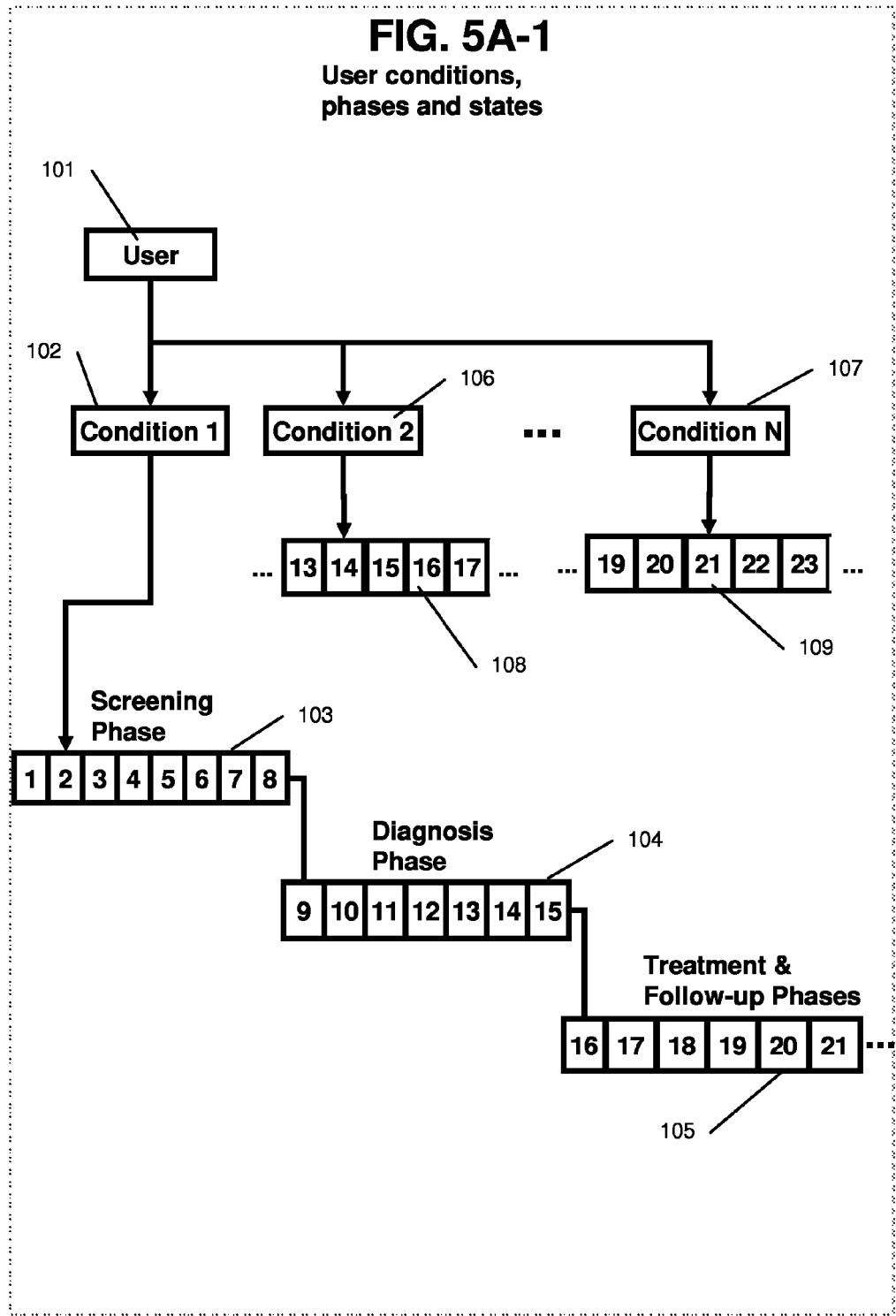

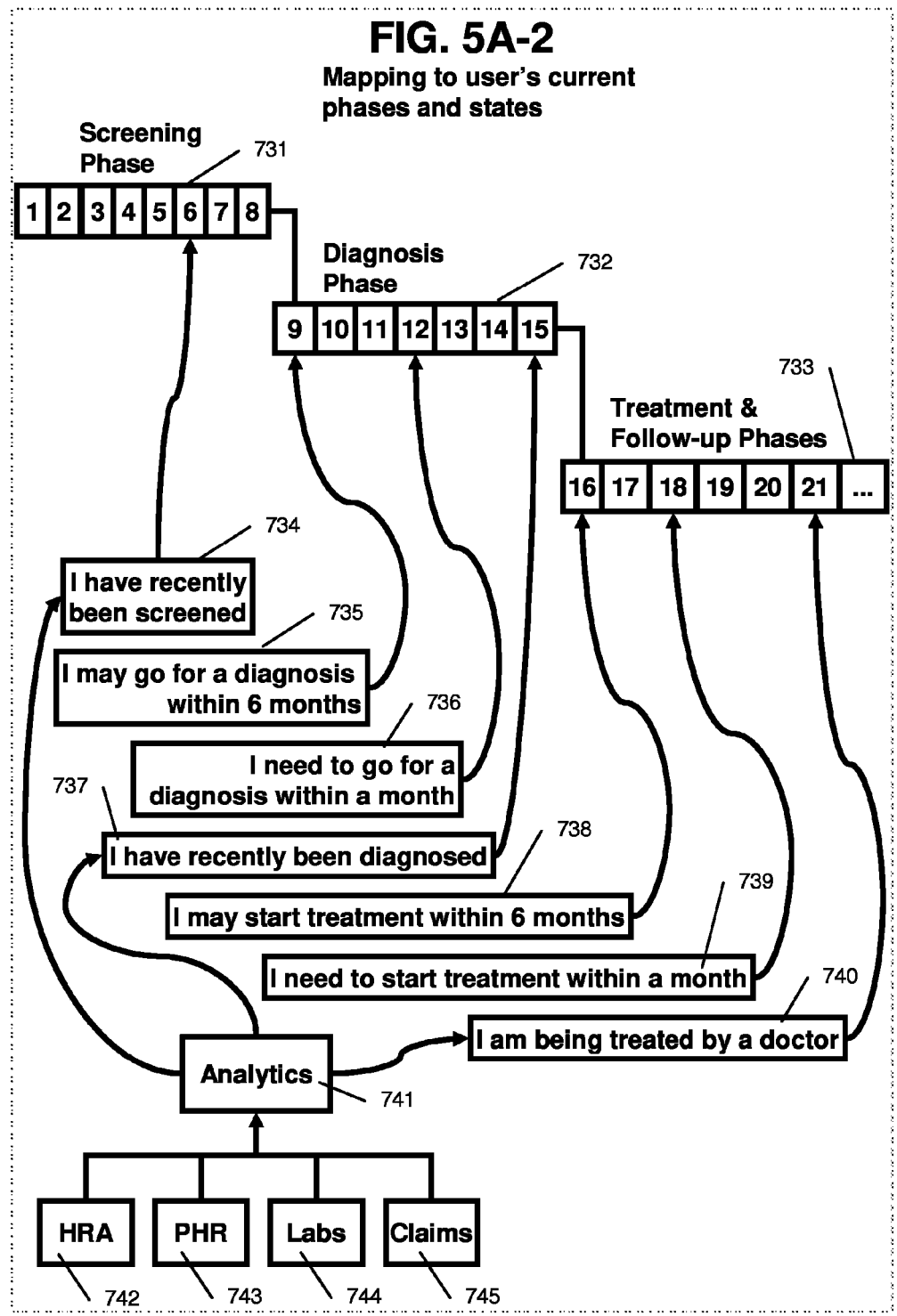

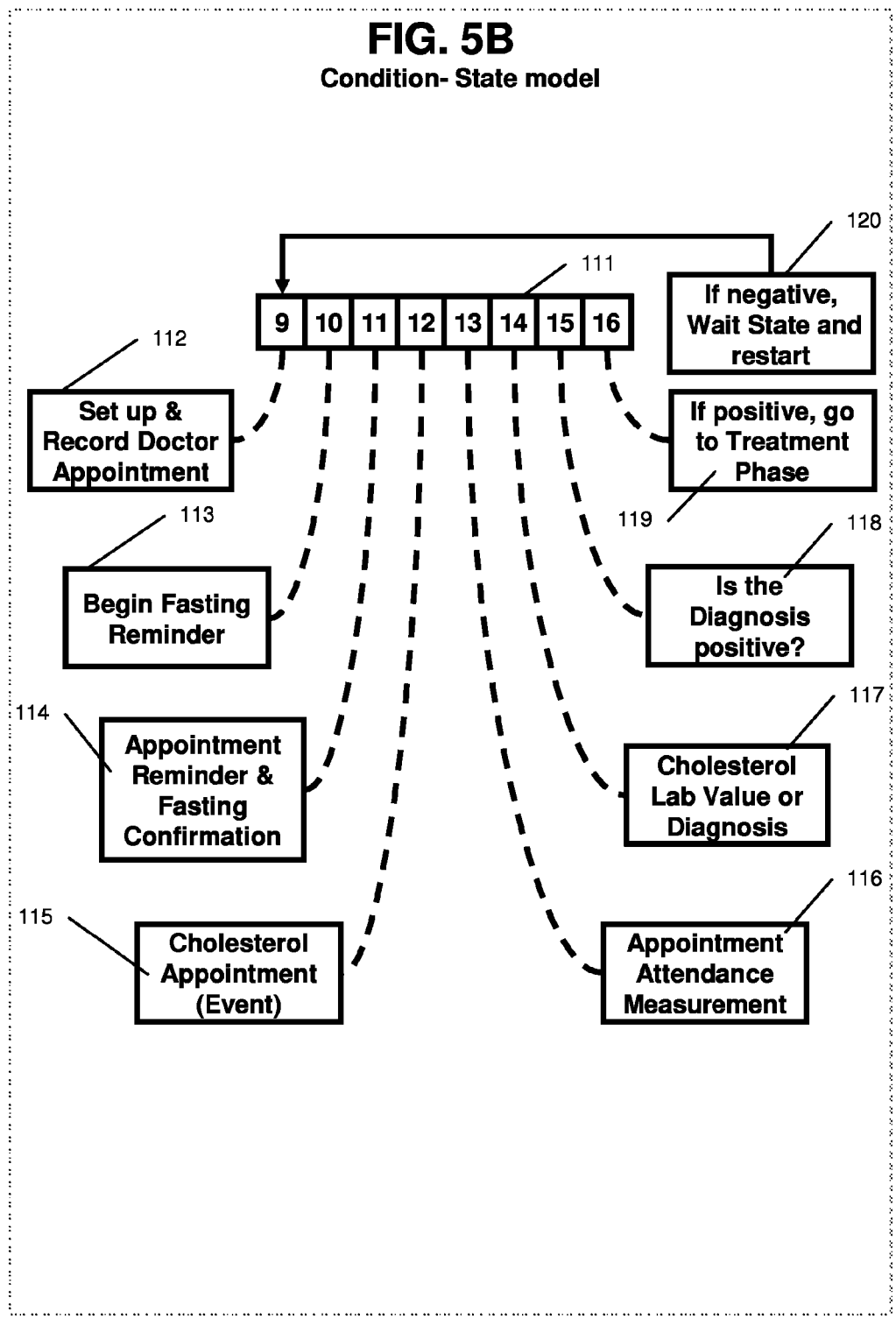

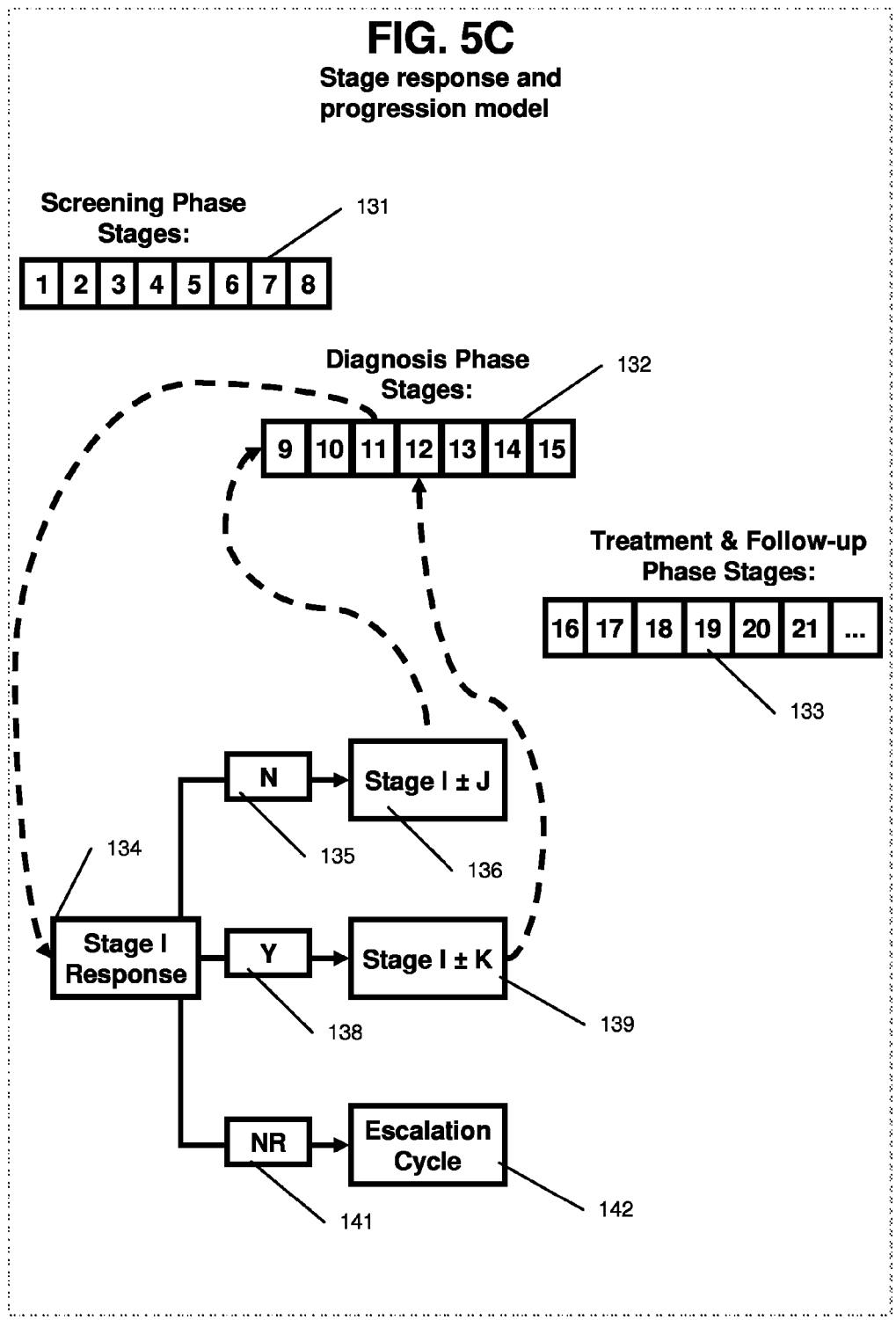

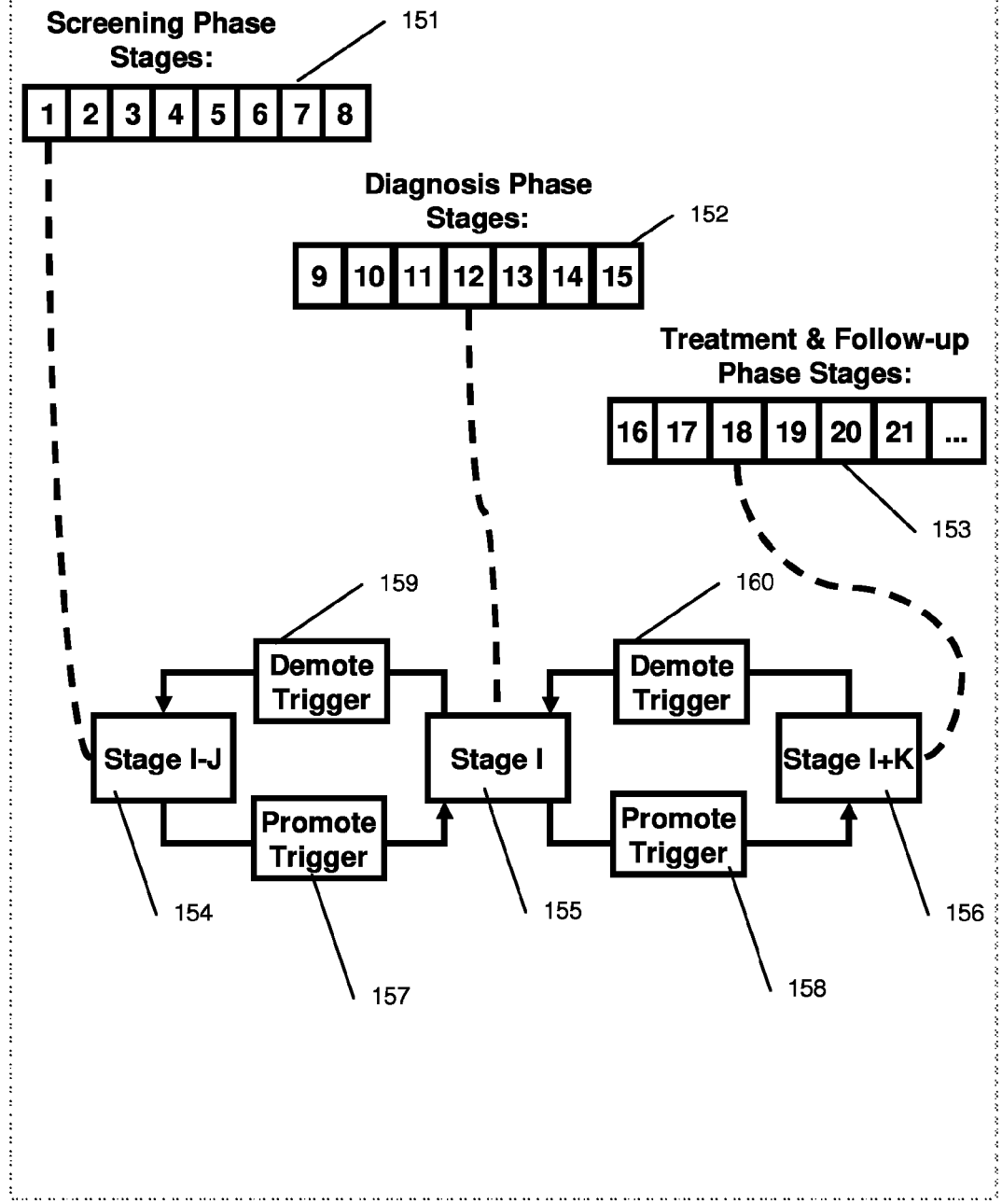

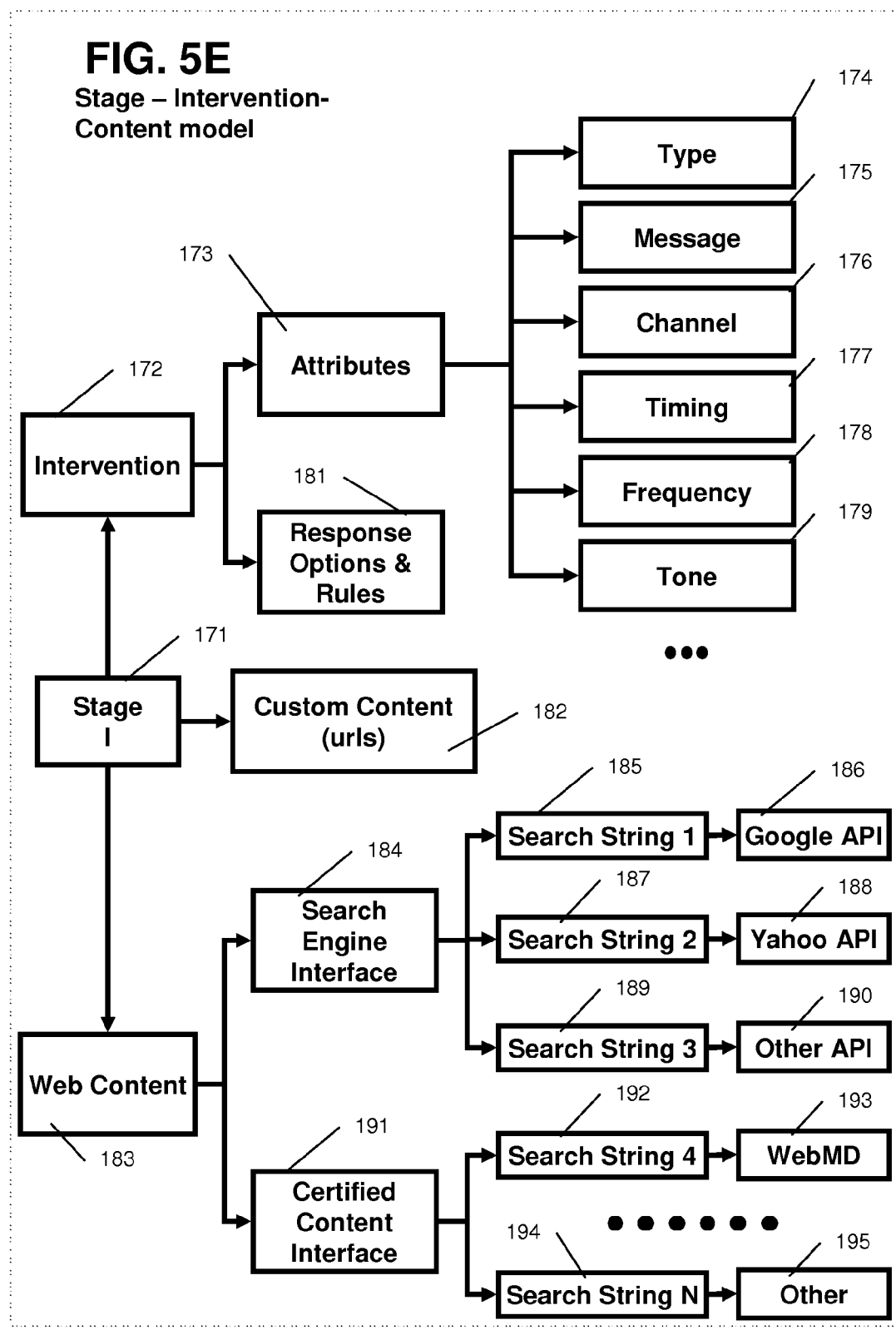

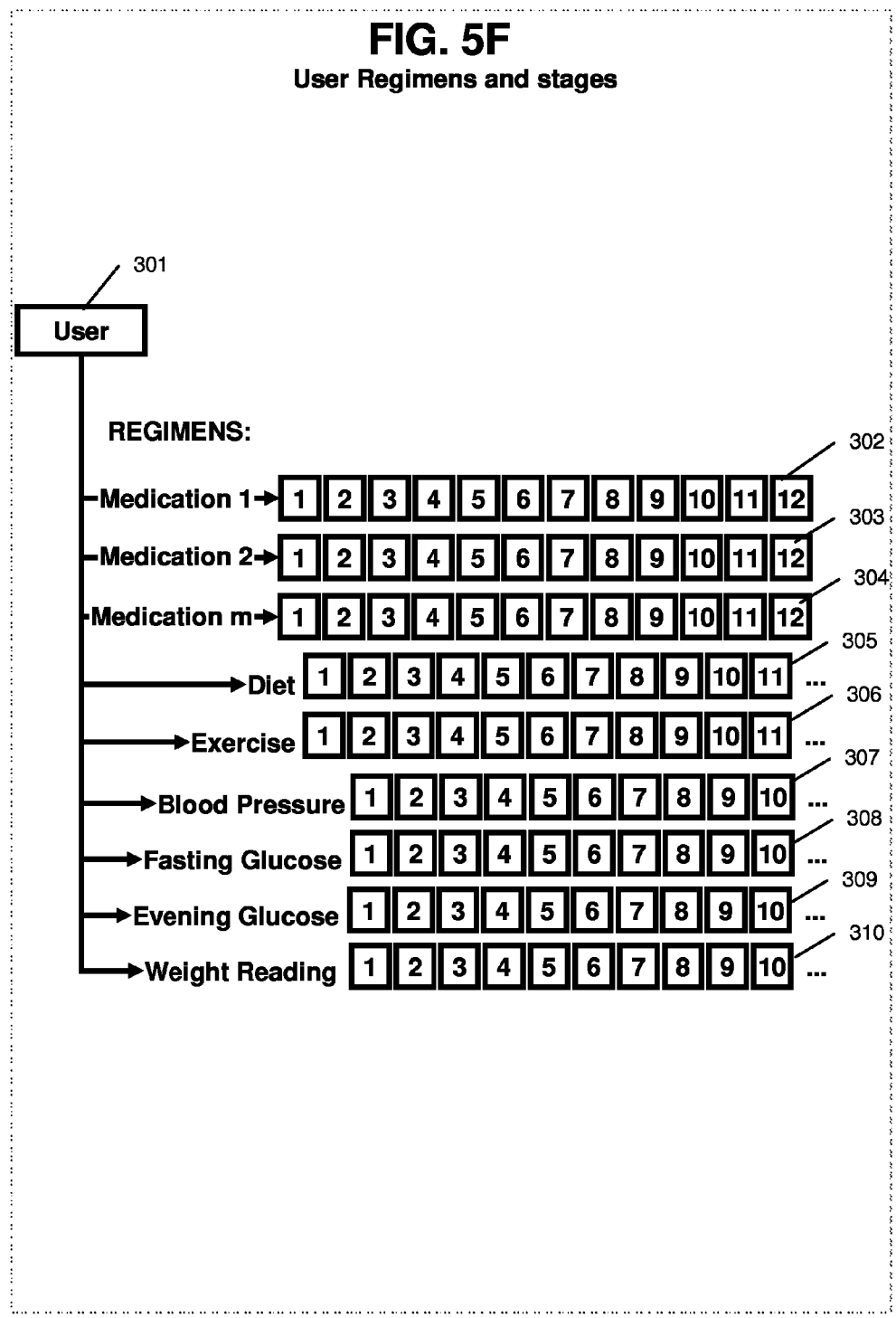

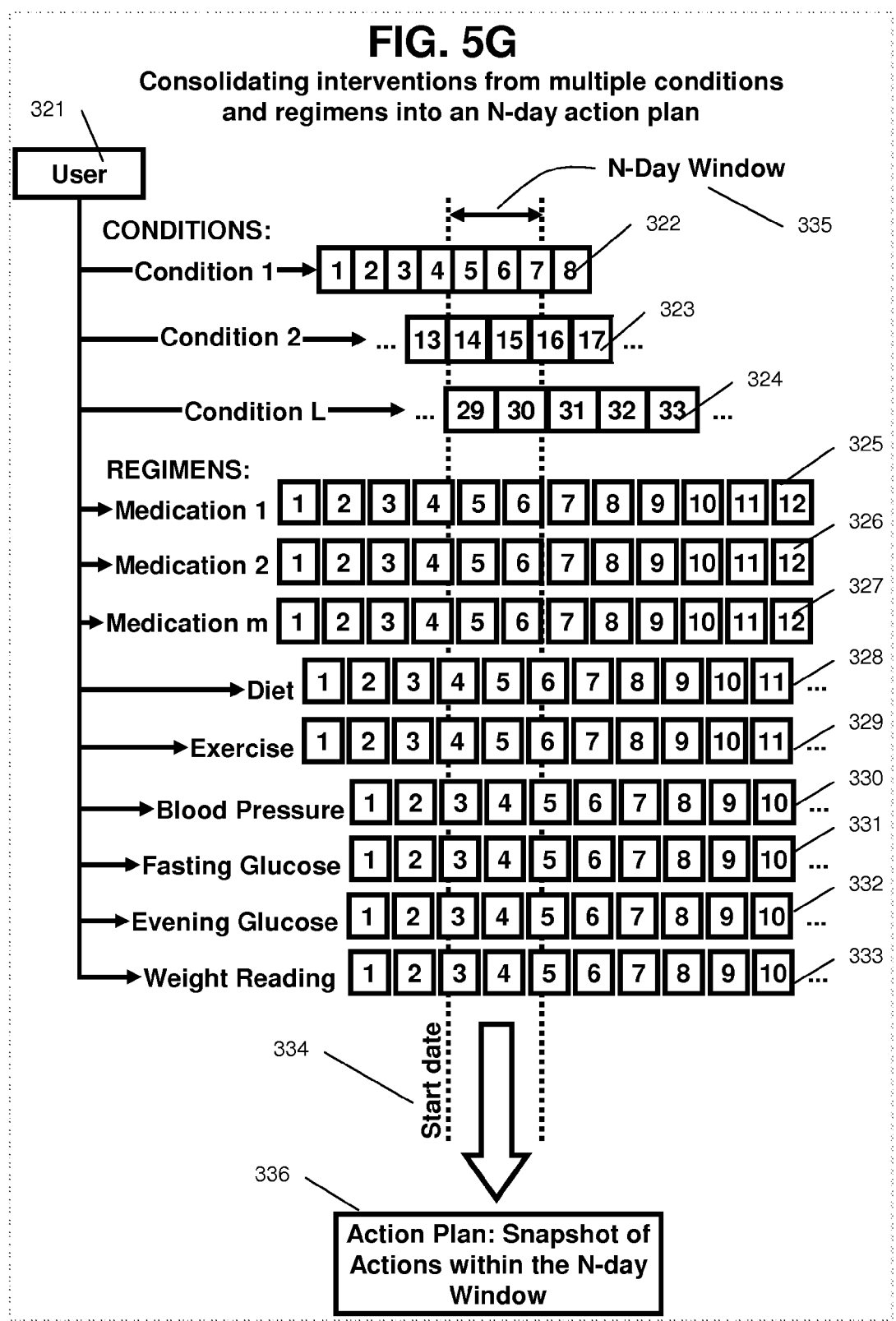

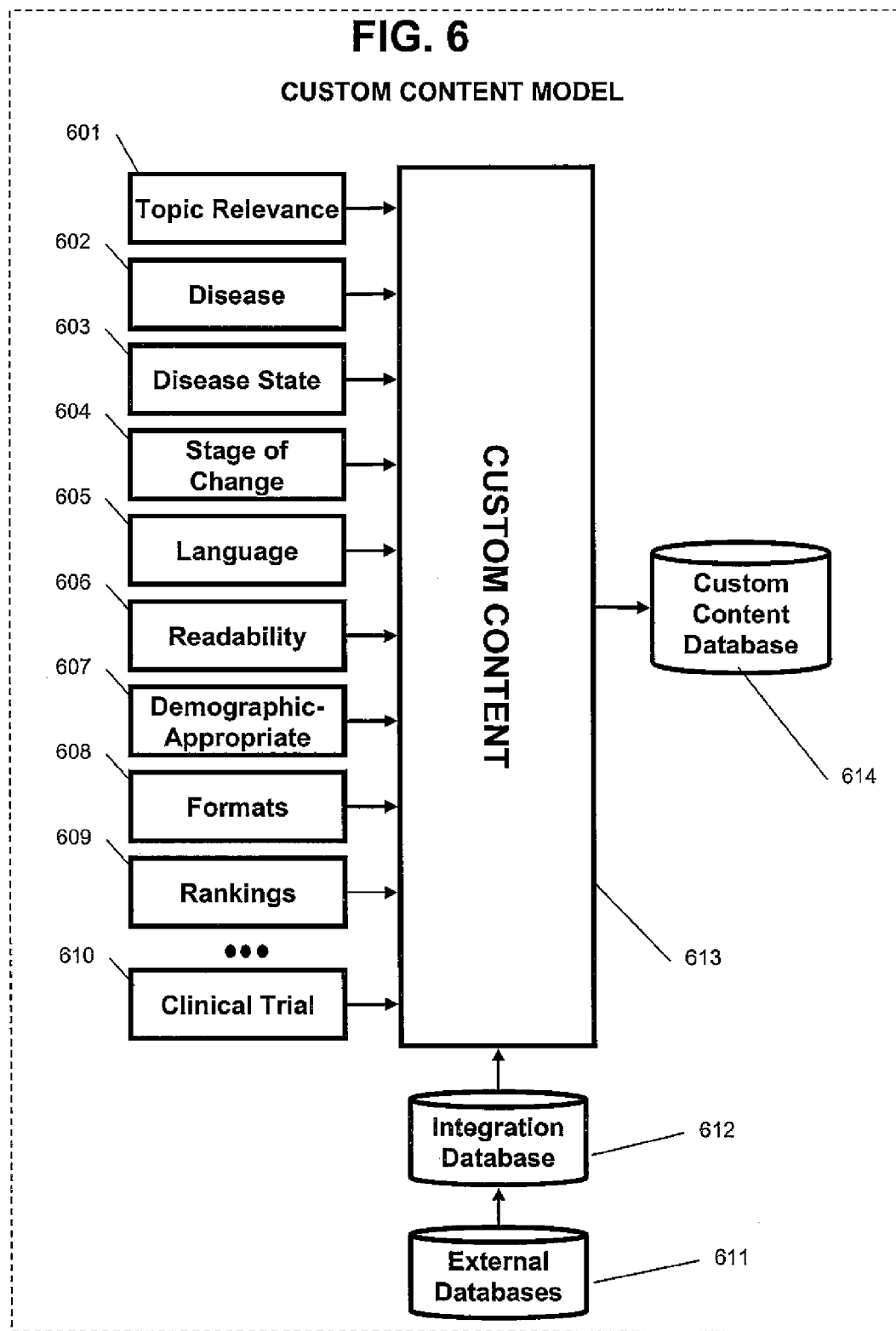

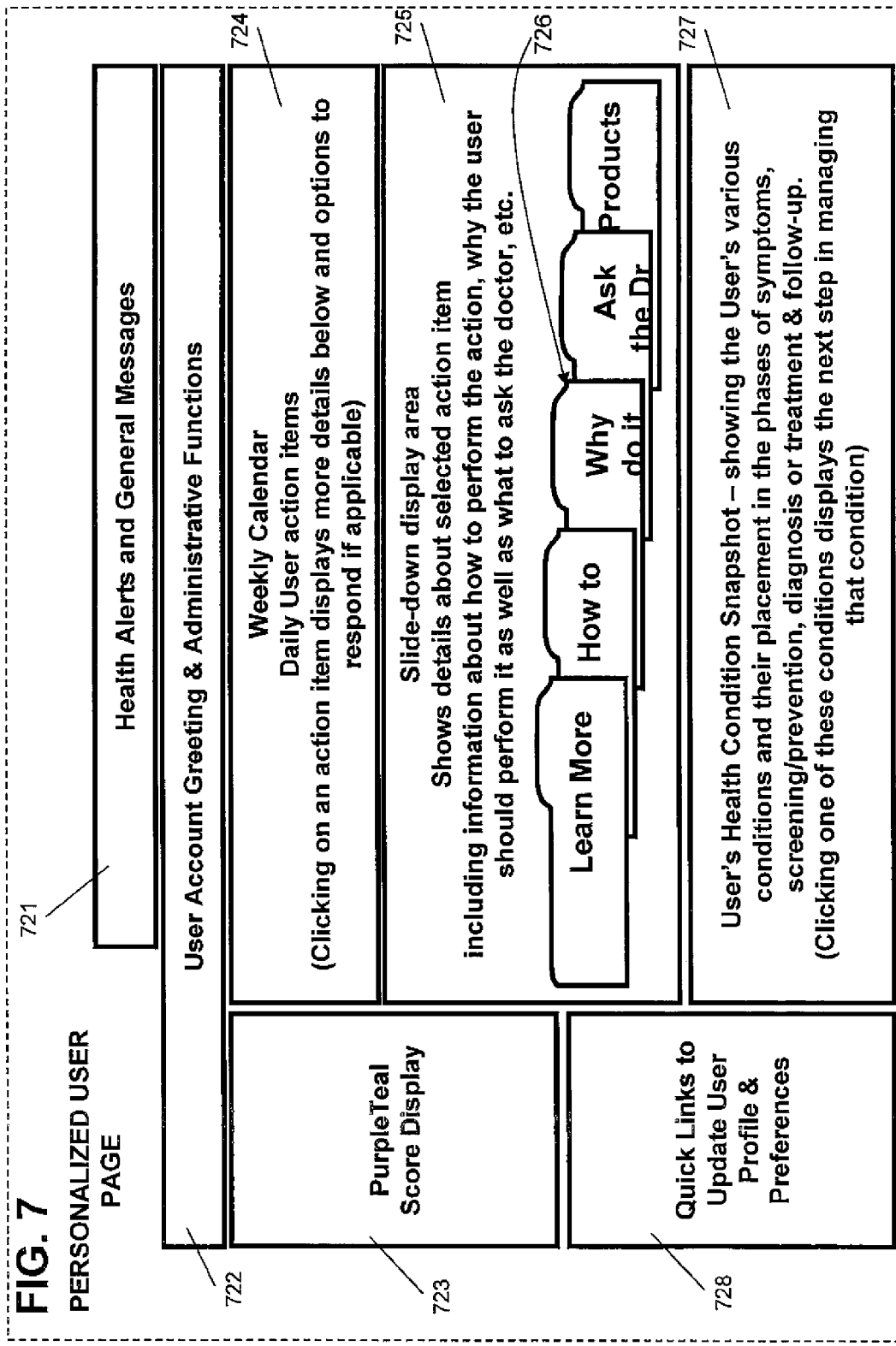

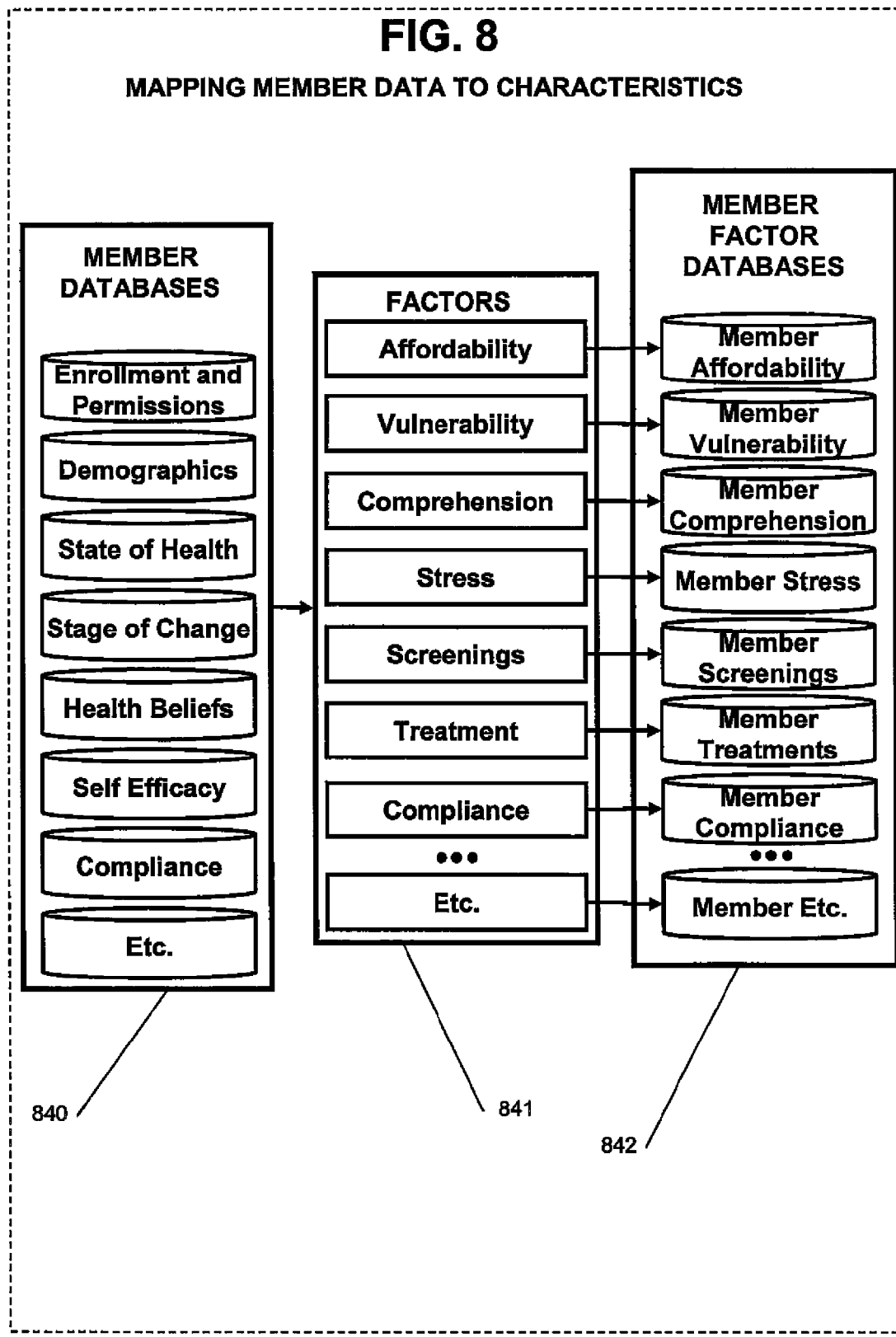

MEMBER DEMOGRAPHICS

FIG. 13 CONSOLIDATED INTERVENTIONS

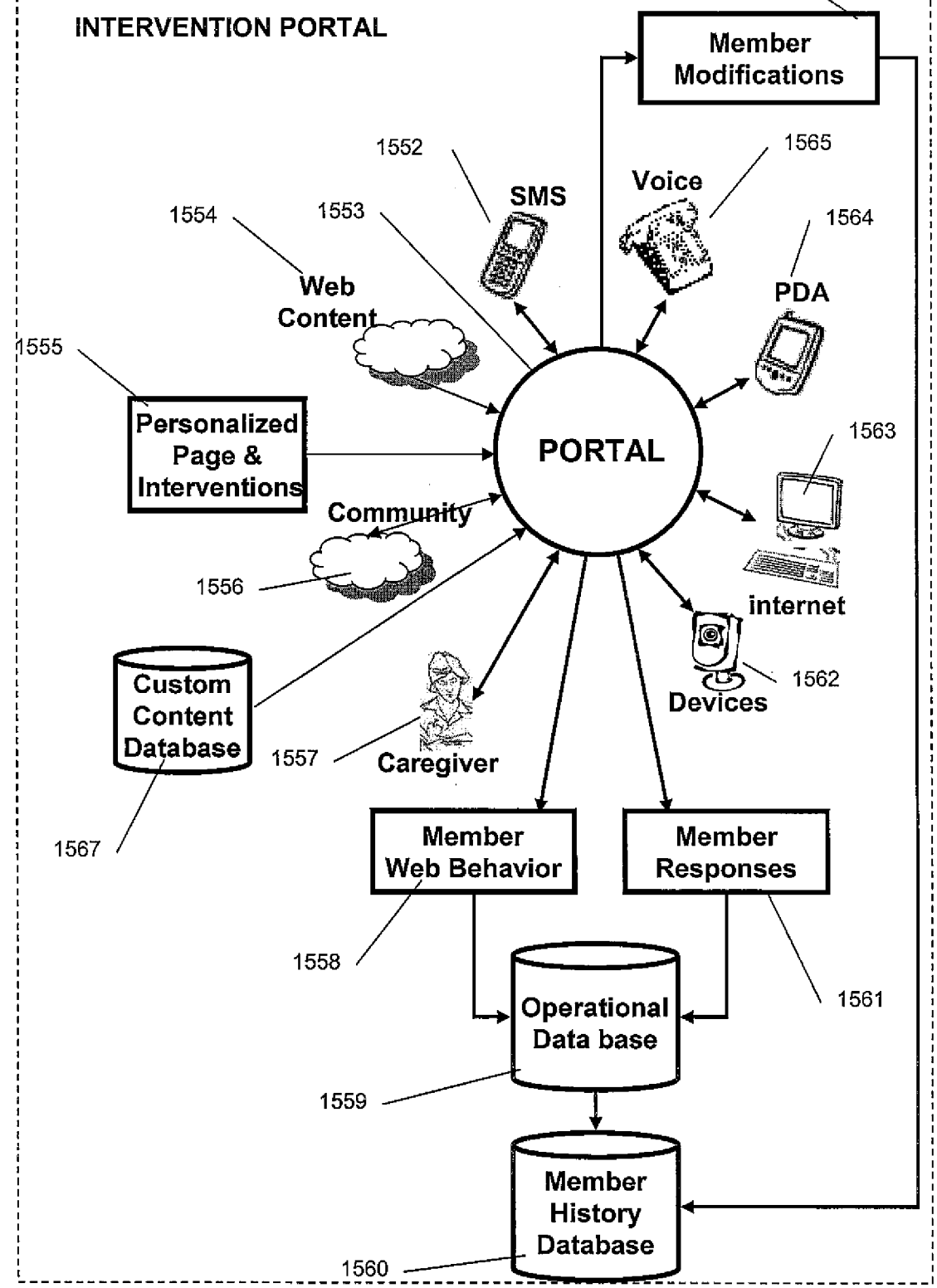

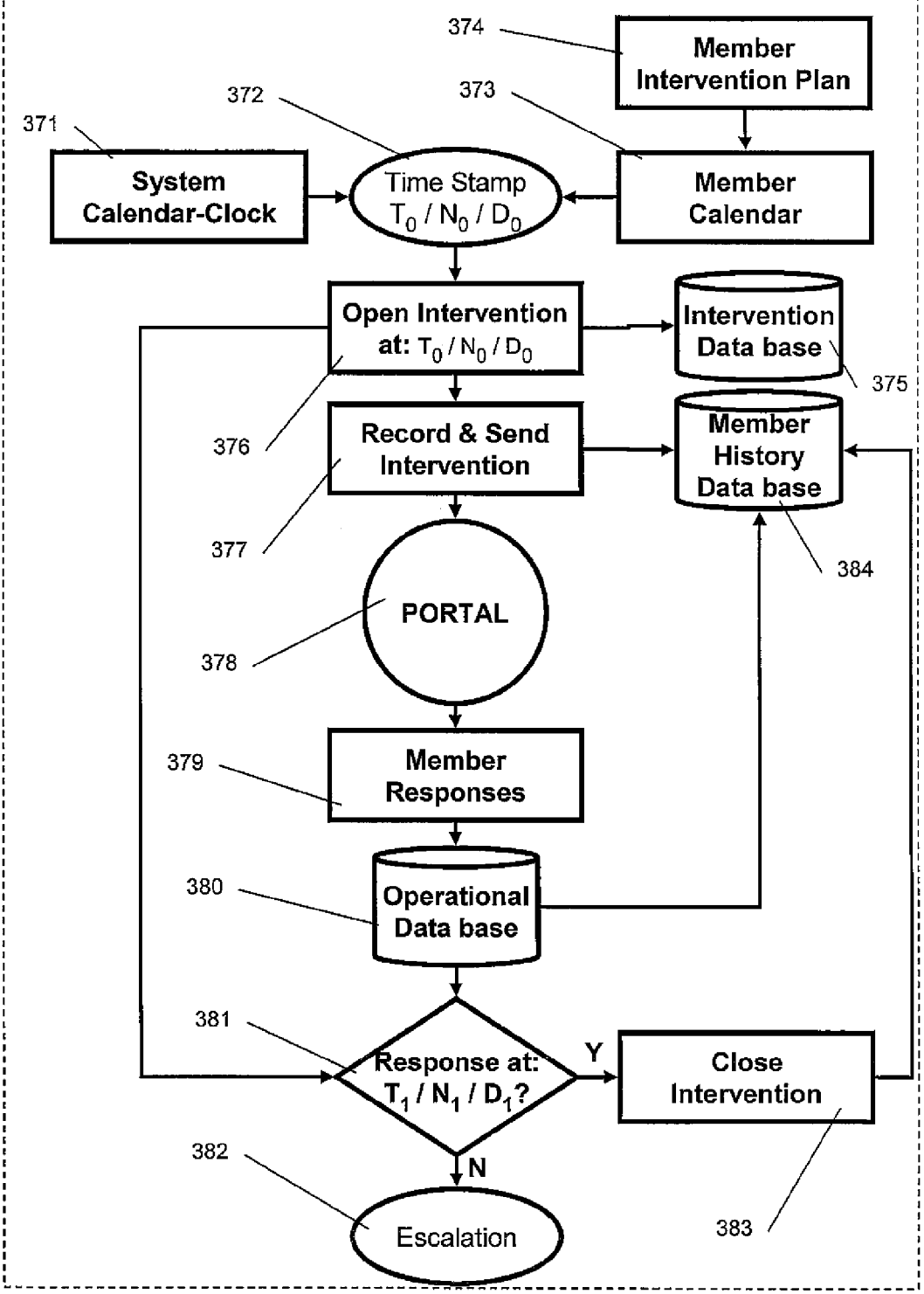

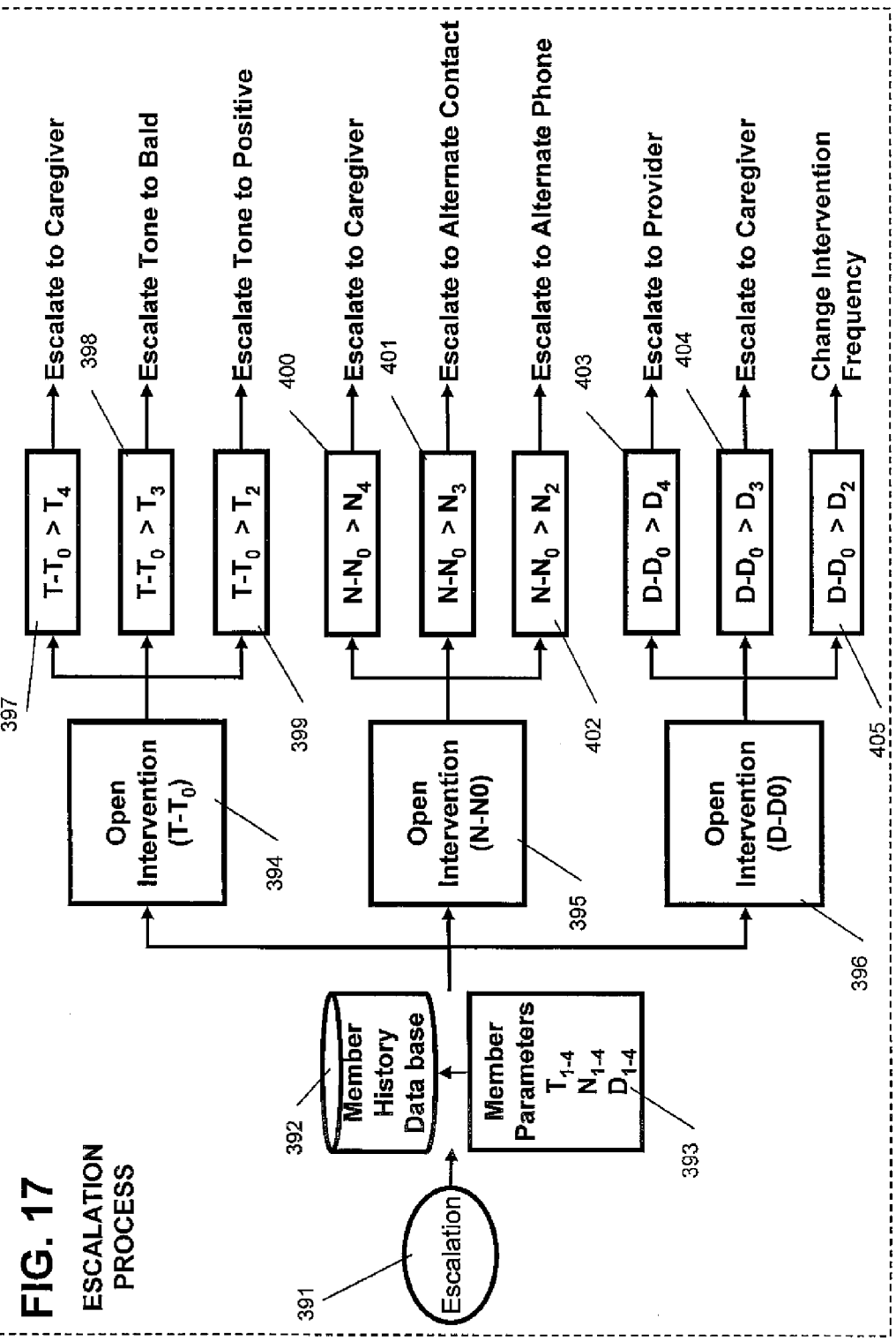

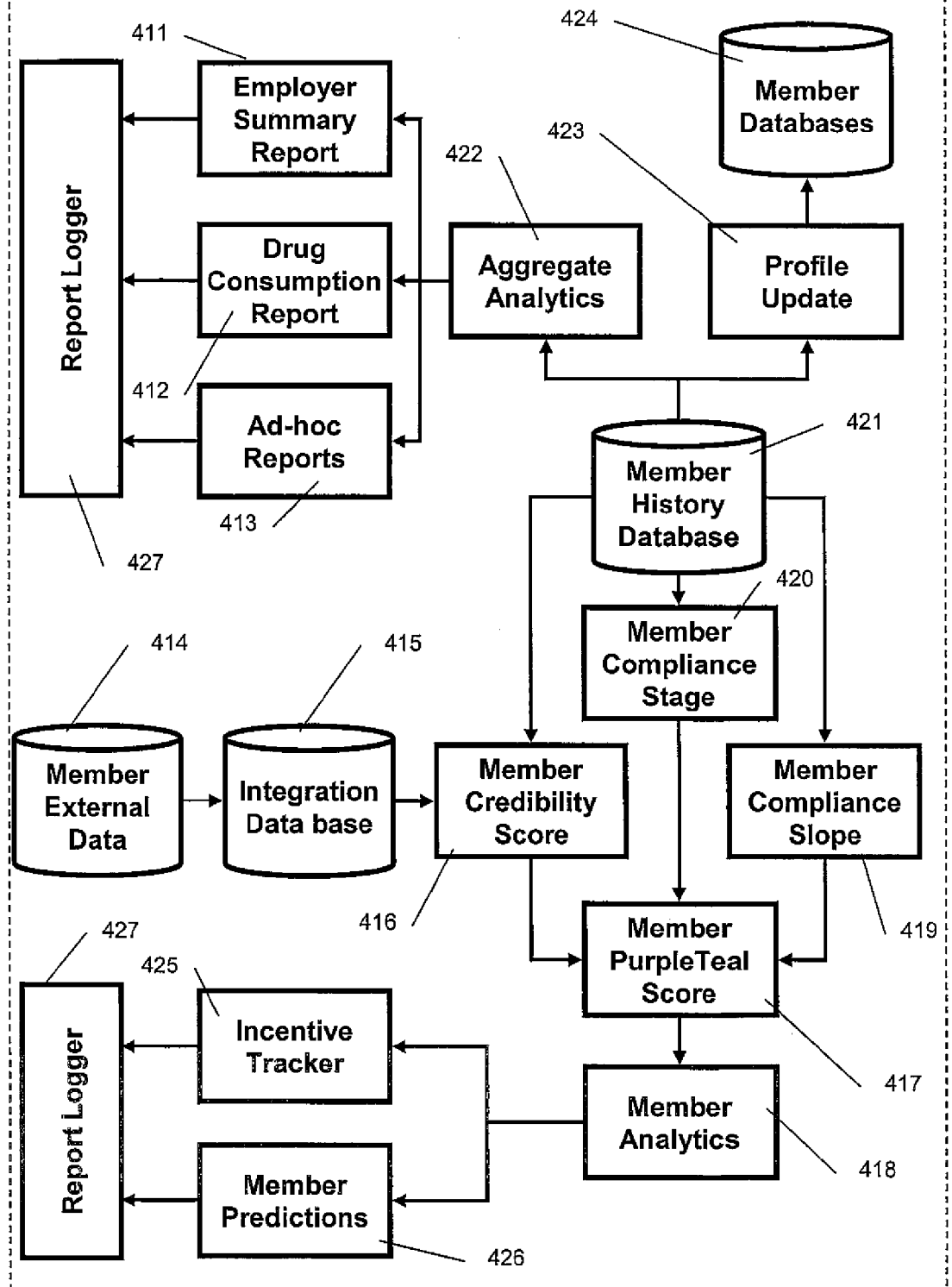
FIG. 18 ANALYTICS

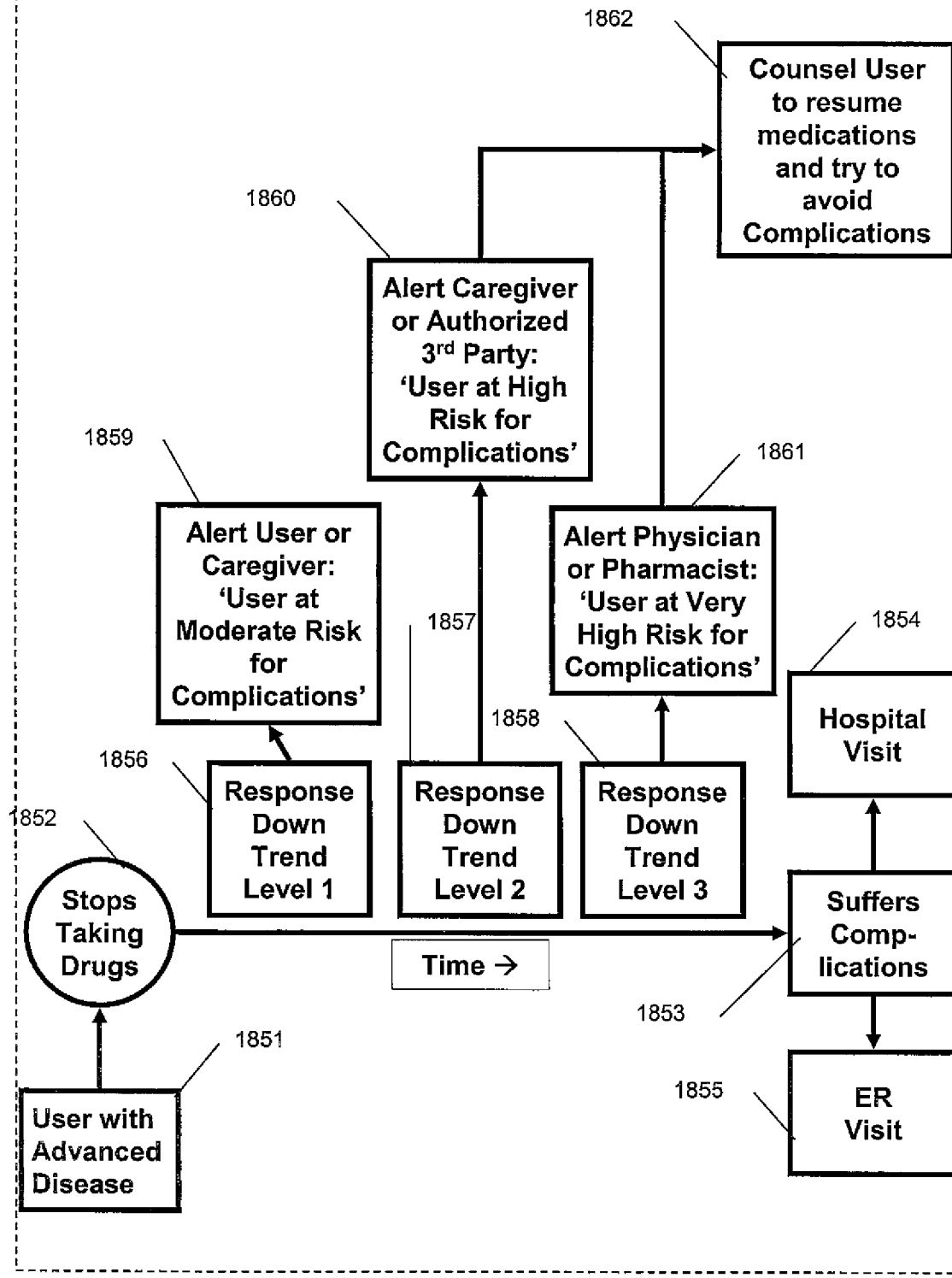

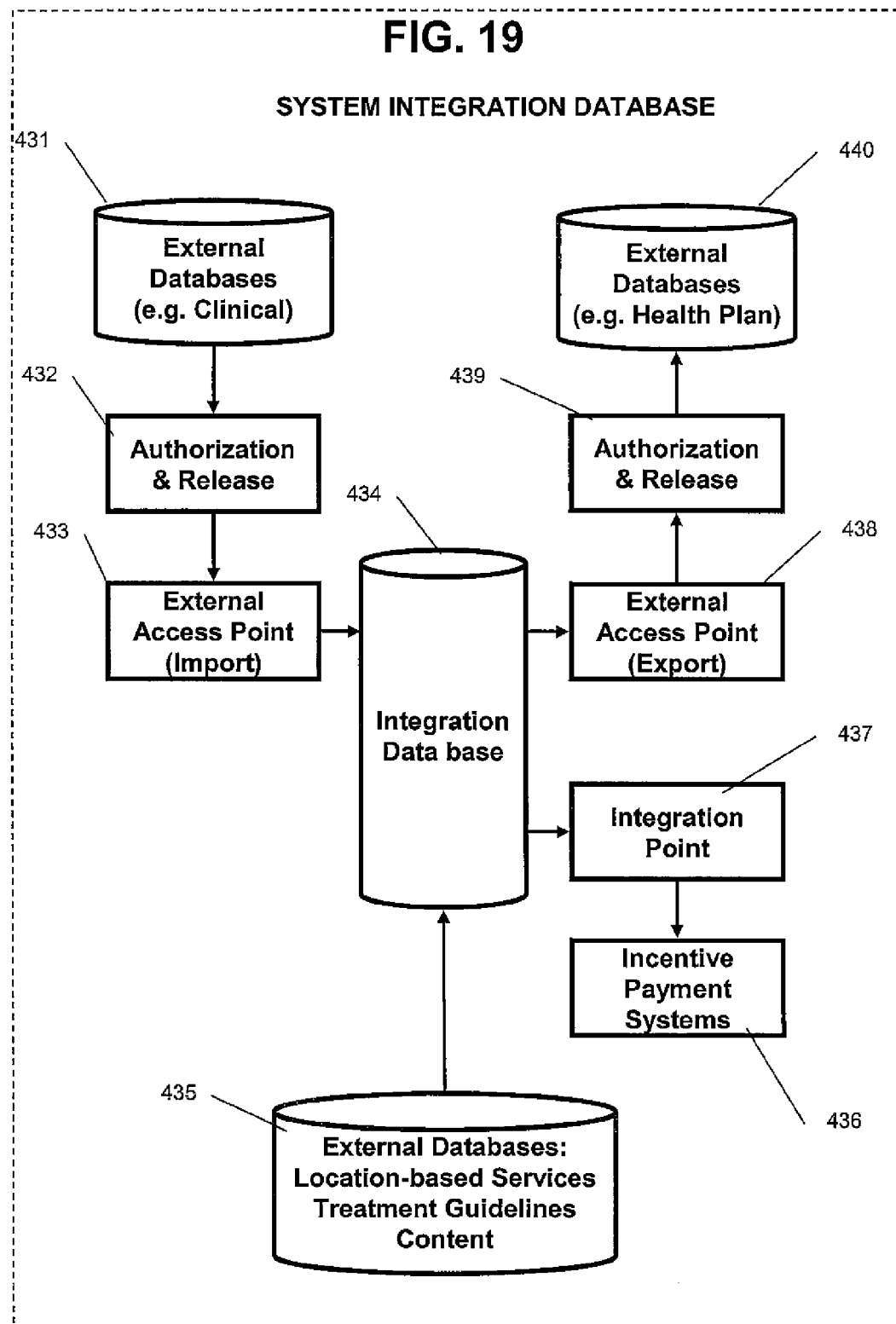

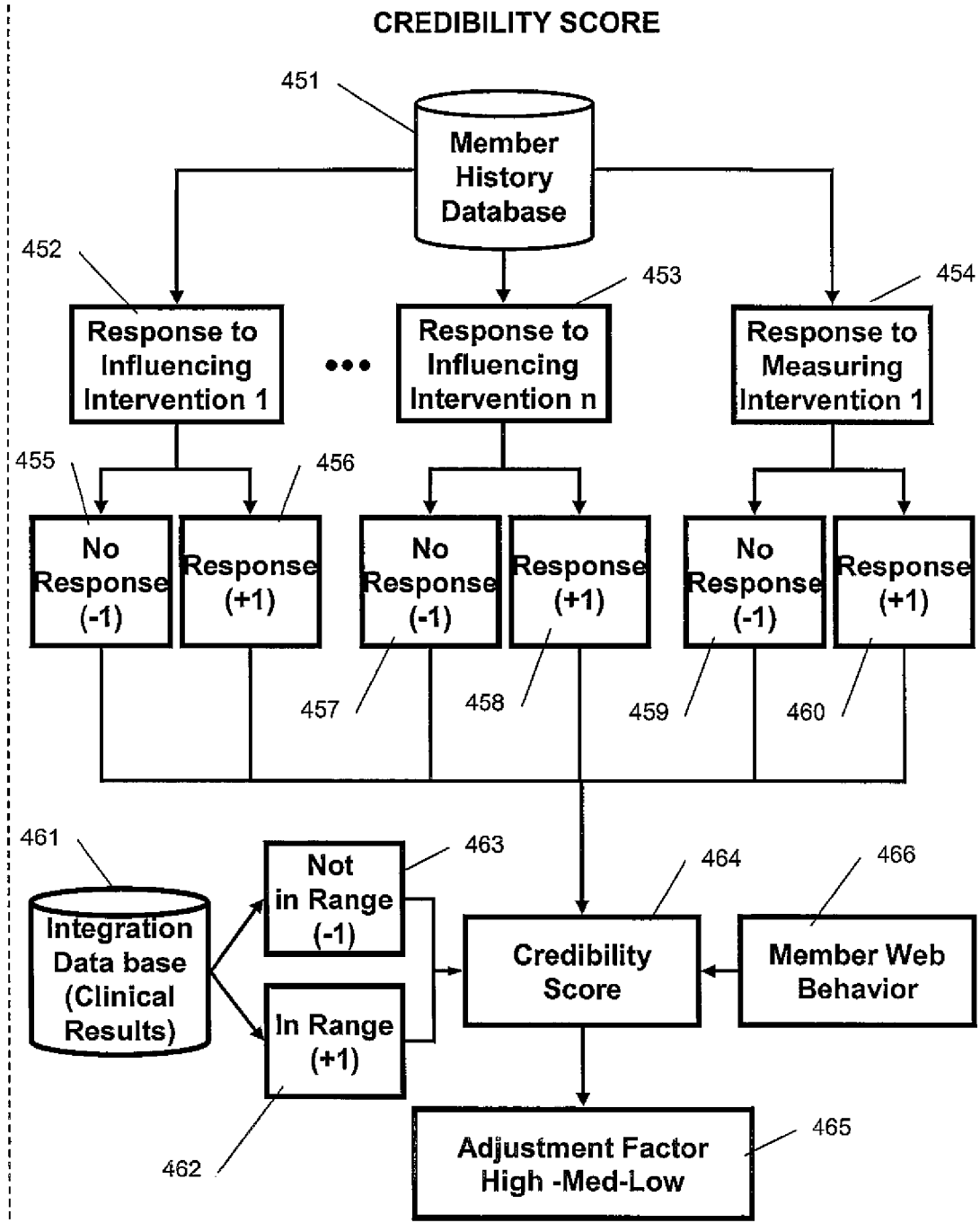

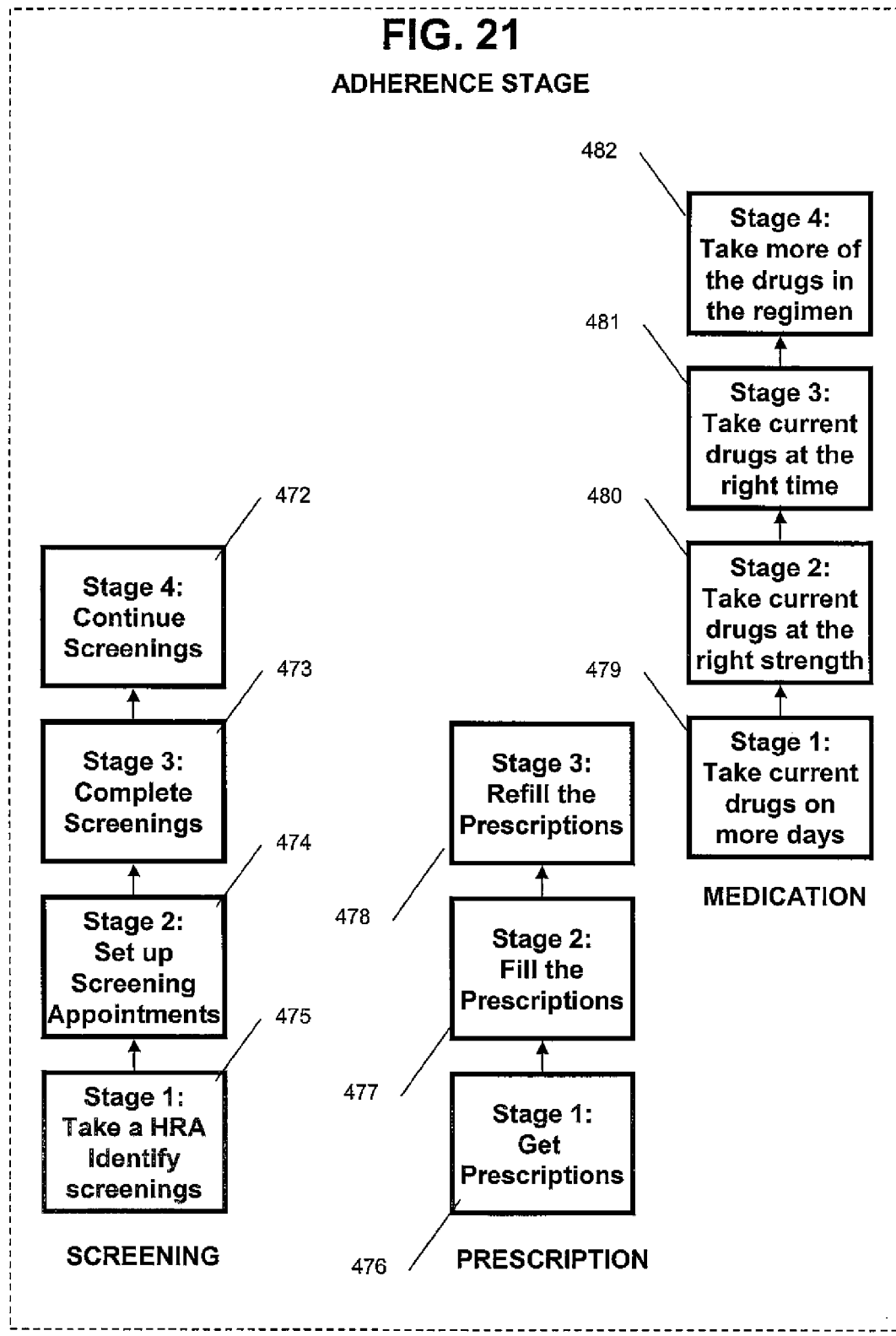

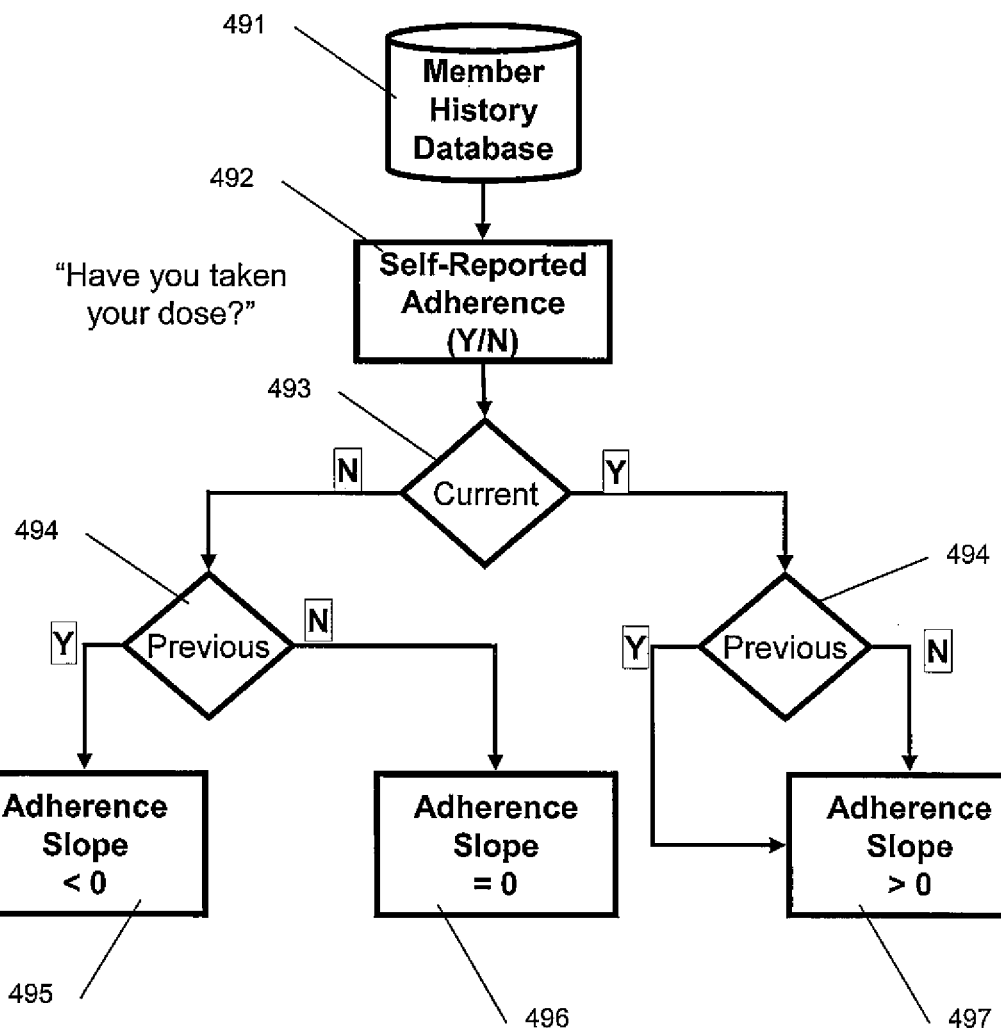

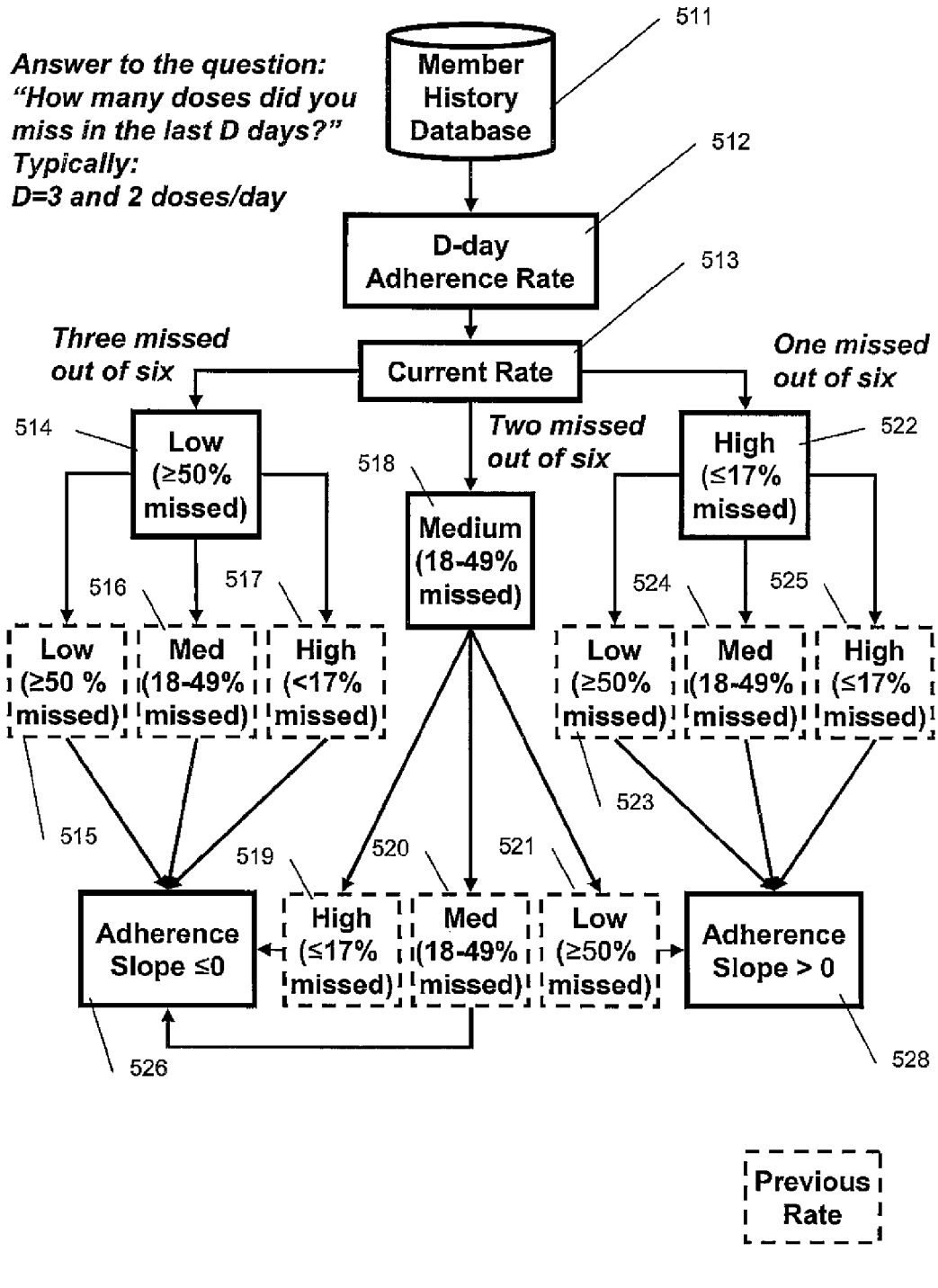

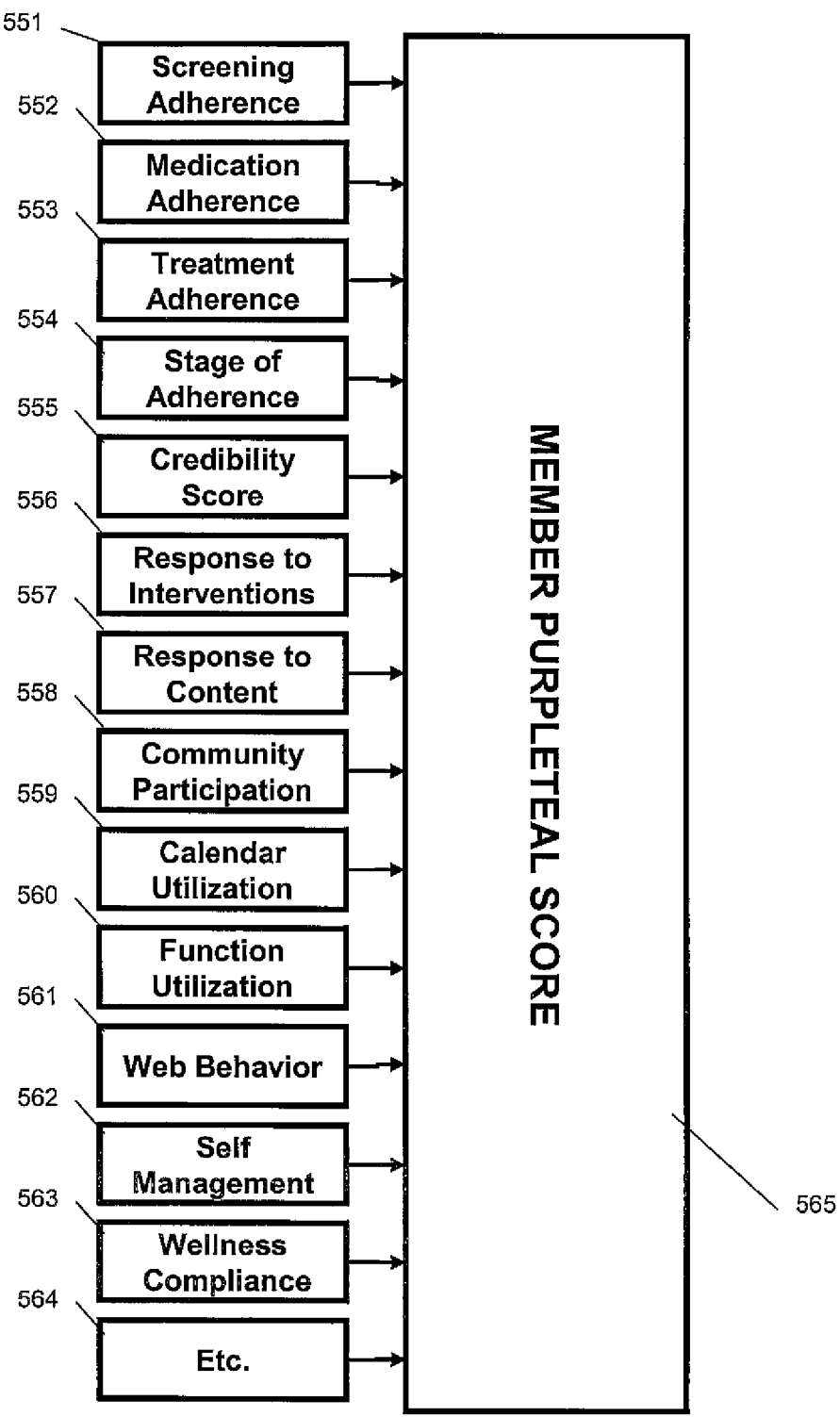

INTERVENTION ADAPTATION MODEL 1

INTERVENTION FREQUENCY ADAPTATION MODEL 2

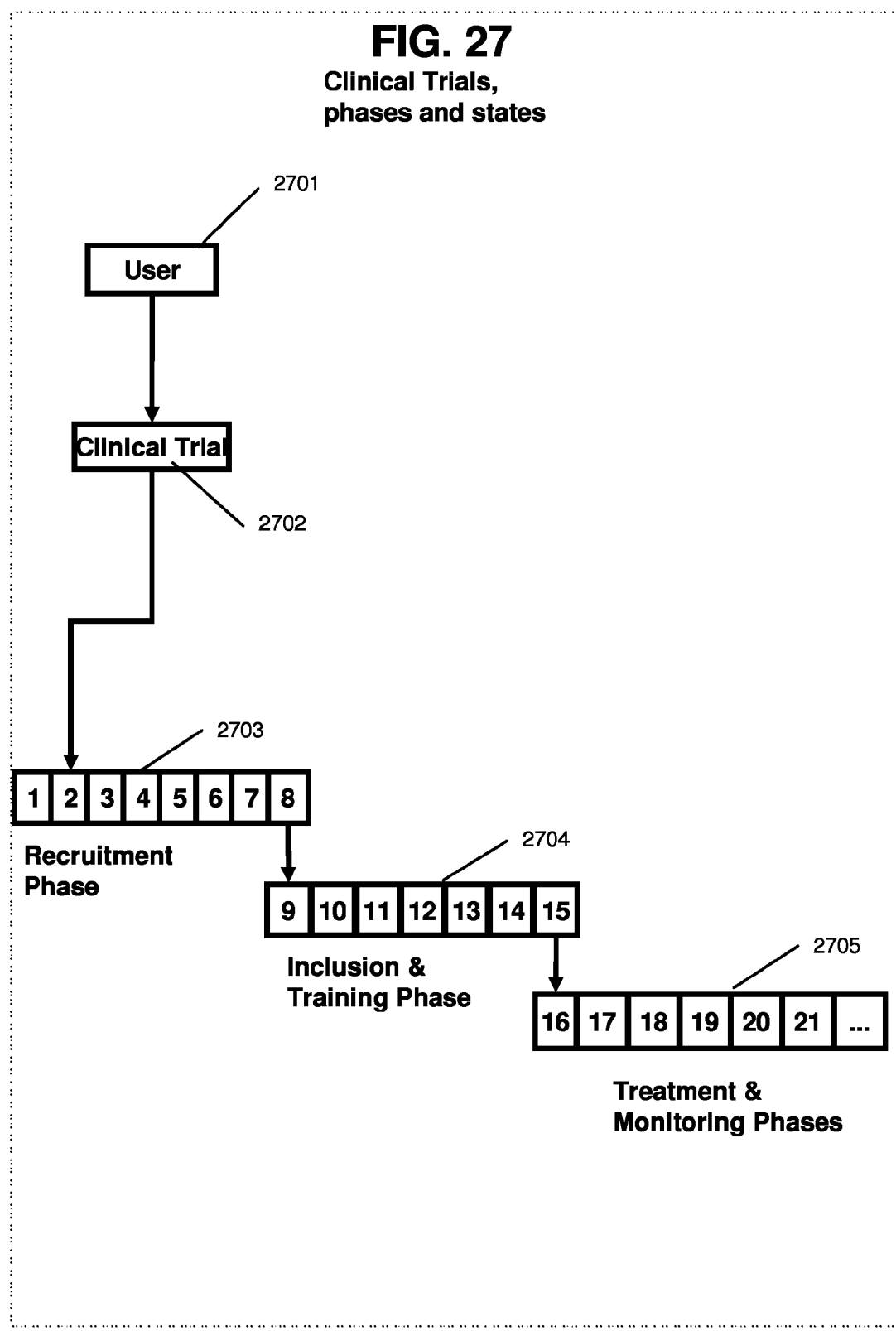

PERSONALIZED MEDICAL ADHERENCE MANAGEMENT SYSTEM

RELATED APPLICATIONS

This application is a Continuation-In-Part of U.S. patent application Ser. No. 11/511,703 filed on Aug. 28, 2006 now abandoned, entitled "Techniques for Improving Loss Ratios", which in turn claims priority to U.S. Provisional Patent Application No. 60/712,751, filed on Aug. 29, 2005.

This application claims priority to the following provisional application, the entire contents of which are incorporated herein by this reference: U.S. Provisional Patent Application No. 60/923,124 filed on Apr. 12, 2007, entitled "Personalized Medical Compliance Self Management System".

FIELD OF THE INVENTION

The present invention relates to improving medical adherence. Medical adherence is defined here in terms of the following: (1) wellness adherence, or actively participating in programs designed to keep people healthy (diet, exercise, weight management, stress management, smoking cessation, etc.), (2) screening adherence, or getting screened for certain diseases based on age, gender, race, lifestyle and other risk factors as per medical guidelines, (3) medication adherence, or filling/refilling and consuming medications as prescribed by a qualified medical professional, and (4) treatment adherence, or going for specific condition-based treatments, procedures, lab tests, etc., as prescribed by a qualified medical professional.

BACKGROUND

Based on age, gender, genetic background, lifestyle and other health risk factors, people generally have health problems and chronic illnesses at different points in their lives. Some of the risk factors are modifiable. By intervening appropriately to reduce the modifiable risk factors, we can improve overall health outcomes, delay or even prevent the onset of diseases, and thus reduce healthcare expenses. The reduction in healthcare expenses represents savings for organizations that pay for the healthcare services.

According to this invention, the key to reducing health risks is improving medical adherence (defined above). Since treating diseases in their early stages is much more effective and cheaper, proper screenings can reduce costs by detecting emergent diseases before they become overt problems. For people who have not been diagnosed with any disease, but may be at risk, the objective is to keep them healthy by improving their participation in wellness and prevention programs. These programs delay or even prevent the onset of chronic diseases. Once diseases have taken root, however, wellness and prevention are not enough; medications or treatments become necessary to keep diseases under control. Thus, for people who have been diagnosed with disease(s), the objective is to retard or prevent the natural progression of the disease(s) by improving their medication or treatment adherence, in addition to improving their participation in wellness and prevention programs.

Medication adherence is characterized in terms of what the patient does after receiving a prescription from the doctor or nurse. Studies show that around 14 percent do not even fill the prescription at a pharmacy, and overall medication adherence is only around 50 percent. Medication non-adherence takes place in various modes: missed drug, wrong drug, missed dose, wrong dose, or wrong time. Any of these modes would make the drug-taking different from the controlled conditions of the clinical trial under which the drug's efficacy has been established. Thus the patient, taking the drugs in these non-adherence modes would not experience the expected health outcomes to the same level of effectiveness.

There are several reasons why medication adherence is so low. According to a detailed study of non-compliance, patients: (1) forget, (2) cannot get prescriptions filled or delivered, (3) do not want the side effects, (4) cannot afford the drug, (5) do not think they need the drug, or (6) do not know how to use the drug. Other cited reasons include personal feelings or beliefs, such as: (1) "I don't have symptoms", (2) "I feel fine", (3) "I am not convinced I need the drug or of the drug's benefit", (4) "It can't happen to me", (5) "I am afraid to take the drug because of adverse effects", (6) "the side effects are too uncomfortable", (7) "I can't remember to take the drug", (8) "The drug is too expensive", (9) "I think my health problem has been fixed"—and discontinue drugs as soon as they feel better, or (10) "If more is better, let me increase the dosage to speed up the cure".

Current interventions predominantly address a particular singular reason for non-adherence. For example, there are several 'reminder' services that automatically send a voice or SMS message to the individual's cell phone at the appropriate times of day to remind him or her to take their medicine. This is very useful for individuals who tend to forget, but only an irritant for those who are quite regular and don't forget. Another example is the suspension, by health plans, of co-pay or co-insurance for drugs that are used to control certain diseases, such as diabetes, in an effort to get individuals to at least fill their prescriptions (the hope is that they will later take the medicines as prescribed). This may help diabetics who are currently not filling their prescriptions because of cost considerations, but it may not be necessary for diabetics who can afford the copays and were going to fill their prescriptions anyway. Further, this only removes the cost barrier for diabetics to fill their prescriptions. It does not necessarily influence or enable them to take them as prescribed, at the right times and dosage strengths. In addition, there is no feedback loop to confirm that individuals are indeed taking the drugs as prescribed. A combination of the above two interventions might be quite effective for diabetics who not only have financial constraints that keep them from filling their prescriptions, but also tend to be forgetful. Thus, even with two potential interventions, we can see that the effective applicability can be quickly narrowed down to a small subset of individuals.

In general, there are hundreds of potential interventions and each intervention only works for a small segment of the population, at a particular time, so any single intervention will only have a small impact on overall adherence. This invention seeks to overcome this drawback by first selecting appropriate interventions based on the individual's needs and preferences, then personalizing the interventions, and further adapting the interventions as the individual's needs change. An individual's needs change with the natural (uncontrolled) progression of medical conditions over time, starting with a 'healthy, but at-risk' phase towards an 'early signs or symptoms' phase, followed by a 'diagnosis' phase, and, if diagnosed, a subsequent 'treatment and follow-up' phase. If left uncontrolled, some medical conditions may progress towards complications, disabilities and even death. At each phase, the individual needs to act in different ways.

There are yet other reasons for poor adherence, and these are very specific to individual patients. In terms of the 'State of Health', the reasons for non-adherence are different depending on the disease, whether it is hypertension, high cholesterol, depression, diabetes, multiple sclerosis, and so on. In terms of the 'Health Beliefs', adherence depends a lot on the patient's perceived susceptibility, severity, barriers, benefits, cues to action, trust in doctors, trust in medicines, and so on. In terms of behavioral 'Stage of Change', much depends on whether patients acknowledge their health issues or are in denial; specifically on whether they are in 'Precontemplation', 'Contemplation', 'Decision', 'Action', or 'Maintenance' stages. Following a diagnosis, patients may go through the stages of 'Denial', 'Anger', 'Bargaining' and 'Depression' before finally 'Accepting' that they have the diagnosed condition and that they need to actively seek and adhere to proper medical treatment.

Demographics also play a key role; age, gender, race, income, family size, family arrangements, education, and so on have an impact on the level of adherence. Personal factors, such as caregiver availability, type of job, hobbies, travel patterns, daily commute, personality type, inertia level, desire for secrecy and peer influences, enter into the picture as well.

These reasons are not only very specific to individuals, but they also vary over time for the same individual, since at any particular time, the individual is subject to various situational factors. These factors interact with the individual's current behavioral state and health beliefs, and produce a current level of receptivity to specific types of influences and information. Given this, merely transmitting pre-planned messages, even if they are somewhat personalized, has a reduced chance of being received and acted upon by the subject individual. If the individual does not consider the message or content to be relevant or of value, he or she may simply ignore it, or worse, tend to ignore subsequent messages from the same source—this is all well-known. It is also well known that individuals' receptivity and response to interventions improves when the number of interventions at any time is small. Faced with a large list of 'things to do', over long periods of time, as is the case with many web sites or services that deal with specific medical conditions, individuals find it difficult to decide which action to perform at any time, and end up procrastinating or doing things that are easier but not necessarily effective. The chances of getting the individual to act effectively are much higher if he only has to perform a few actions, over the course of a given day. Accordingly, in order to maximize the chances of being received and acted upon, a main goal of this invention is to provide timely interventions that are highly personalized, relevant and matched to each individual's current medical and behavioral stage, and also organized by daily, weekly, monthly, or other user-specified time windows, in an effort to present the smallest number of the most actionable interventions at any particular time.

Effecting change in behavior, such as going for health screenings, participating in wellness activities or medicine-taking, requires a consistent set of messages to get through to the subject individual for a certain length of time, at a frequency that keeps the messages from being forgotten. Studies on memory formation and forgetting are useful in setting the intervention frequency, and the often-cited cybernetic view that it takes three to four weeks for a new habit to develop is also useful in setting the duration of interventions. Thus not only do the interventions (that convey the messages) have to be highly personalized, relevant and matched to the current medical and behavioral stages, they must also be provided at a frequency that maximizes the likelihood of being received and not ignored. If the interventions are too frequent, the individual may turn them off, considering them a nuisance. On the other hand, interventions that are too infrequent have limited or no effect in changing the behavior. Interventions must provide some value to the individual, such as imparting interesting information, pointing them to useful hints and tips, and so on. Also, the content must be fresh and engaging—the same content repeated multiple times loses the effect. Accordingly, another goal of this invention is to select the interventions such that relevant, but possibly different, content is provided at different times. Yet another goal is to match the frequency of the interventions to the individual's preferences at a particular time.

Personalization of interventions based on static knowledge about the individual is a good starting point, but the impact is rapidly lost if the personalization is not refreshed based on the individual's response. Continuing to send interventions similar to those that have been ignored or dismissed by the individual serves no useful purpose and may even alienate the individual. On the other hand, avoiding these interventions can help. Modeling future interventions around those to which the individual has responded positively, is more likely to sustain the interest and level of engagement of the individual. Accordingly, a goal of this invention is to seek individual responses to interventions, in terms of usefulness, relevance, value etc., and to use these responses to model and adapt further interventions.

Existing approaches to improve adherence in general do not concern themselves with what happens after the patient fills the prescription; in other words, adherence equals 'possession'. However, what matters to good health outcomes is not whether the patient fills the prescription, but whether the patient actually takes the medication as prescribed. Accordingly, this invention seeks to improve adherence in terms of how well the patient follows the prescription, i.e., whether the right drug was taken at the right time, at the right dosage, and whether all the prescribed drugs were taken.

Some approaches provide interventions in the form of a one-time plan generated on the basis of static information about the patient. The patient is required to perform the activities in the plan, and there are periodic (e.g. quarterly) follow-ups. Issues of cost due to the reliance on physical mailings or expensive nurse labor may dictate this infrequent follow up. It is known that interactive and frequent interventions work better, so while these approaches are getting some results, much better results are possible with more frequent and personalized follow up. This invention, as mentioned previously, seeks to provide interventions frequently enough to change behavior, but limits the frequency to individual patient preferences in order to minimize the chances of being ignored.

Another drawback is that currently available interventions are not frequent or granular enough to enable individuals to take specific and timely actions. They periodically advise individuals by means of a list of various activities they need to perform, but do not provide an adequate framework for decision-making ('decision support') or action-planning ('action support'). The individual has to separately research each item on the list in order to decide on which activities to perform and within what timeframe, and then has to break the activities down to actionable tasks to perform the selected activities. For example, if the activity is to 'get a cholesterol screening', the actionable tasks may be: (a) making an appointment, (b) fasting before the appointment, (c) going for the appointment, (d) obtaining the screening results, etc. It is typically up to the individual to break each activity into such actionable tasks and remain vigilant in order to make sure that the tasks are being performed in a timely manner. All this imposes a large burden, especially for working individuals whose busy schedules leave little room for this sort of vigilance and perseverance; as a result, they frequently fail to perform their required health-related tasks. In other words, individuals are expected to remember and take a number of health related actions on a daily, weekly, monthly, quarterly and annual basis, but with very little by way of day-to-day support. One of the aspects of this invention is that it provides the necessary day-to-day 'hand-holding' support that enables individuals to perform the required health related tasks in a timely manner.

Individuals with multiple chronic medical conditions or susceptibilities are required to perform a number of regularly scheduled health-related actions on a daily, weekly, monthly, quarterly or annual basis in order to keep their conditions under control. They interact with medical professionals for a very small fraction of the time, during which they are instructed about these actions, but are pretty much 'on their own' for the majority of the time during which they have to take these actions. Typically, individuals cannot recall much of the instructions even after a day or two, so it is very difficult to remember them on a long-term basis. There is a need for a way to help individuals find out what actions they should be taking, to help them decide which actions to take immediately ('decision support') and to assist them in actually performing these actions ('action support') on a day-to-day basis. There is a need for far greater granularity in identifying the actions than is provided by existing interventions. This invention provides a health action calendar on a daily, weekly, monthly, quarterly, annually or individually specified periodic basis, in order to inform the individual about various actions in different timeframes. Further, this invention provides detailed information, relevant to each action, in order to assist the individual to 'learn more', understand 'why do it' and see instructions on 'how to do it', as well as 'what to ask the doctor', and so on, in an attempt to help individuals make decisions about performing specific actions. Information about relevant products and services may also be provided, all in the same user interface.

Such detailed information in the categories of 'learn more, or 'how to do it' etc., are provided on many web sites, using clickable links to the information—these links are typically static urls that can be deleted or changed or otherwise become inaccessible over time because they are maintained by third parties. This requires continued investment, in the form of constant vigilance and maintenance of these links. The present invention is novel in the way in which the detailed information is displayed—links to detailed information are dynamically retrieved, created and presented to the individual, in real time. This is done using pre-configured search words associated with the specific action and information category. The search words are passed to free web search engines (e.g. Google, Yahoo, etc.), and the search engines return the search results, or dynamic links, which are summarized and displayed in the user interface. Upon clicking on any of the dynamic links, the system opens a browser window and displays the detailed information. Thus there is no need for any investment in maintaining any links since the relevant and up to date detailed information is retrieved from the web upon clicking on any of the dynamic links. Links to 'certified' or 'trusted' or 'custom' content can also be provided in a similar manner.

Yet another drawback of existing approaches is that the emphasis is on 'telling' the patient what to do, but not sufficiently 'motivating' the patient to take charge of their own health. 'Telling', especially in strong terms indeed has an impact on adherence, but it disappears soon after the intervention is removed. Change in behavior resulting from being motivated has a sounder basis and thus has a better chance of maintaining itself as circumstances change. Accordingly, another goal of this invention is to first understand the 'stage of change' of an individual in terms of target health behaviors (such as medicine-taking or going for health screenings or participating in weight-loss or smoking-cessation programs), then construct a personalized intervention plan. Individuals progress serially through the stages of: (a) pre-contemplation, when they are not even thinking about the target action, to (b) contemplation, when they have begun to consider the target action, to (c) decision, when they are making a decision about taking the target action, to (d) action, when they are actually taking the target action, to (e) maintenance, when they are continuing to take the target action on a regular basis. At any stage, individuals can revert to a previous stage (such as in a relapse), and the progression is restarted from the reverted-to stage. As an example, if an individual is not even contemplating going for health screenings, he needs to be influenced to do so, using interventions with compelling content designed to increase his awareness of screenings, and his perception of susceptibility to disease because of age, gender, ethnicity, lifestyle, etc. The objective is to move the individual to the point of contemplating screenings; once this objective is achieved, a different set of interventions might serve to move the individual to the subsequent decision-making stage, and so on. Thus by using different sets of interventions targeted at different stages of change, the individual is moved forward (i.e. motivated) towards self-efficacy. Accordingly, a key objective of this invention is to progressively 'activate' the individual into taking specific health actions on a regular basis.

An individual may not respond sufficiently to interventions; when this happens, it is necessary to escalate the content in an attempt to increase the urgency or awareness of severity in an attempt to improve responsiveness. A different set of interventions, featuring content designed to increase his perception of seriousness, e.g., what can happen if he lets a condition to progress uncontrolled for too long, and so on. A good example of content in this regard is the TV commercial of a young man who has gone blind because he neglected getting screened for diabetes. Another goal of this invention is to provide a method by which interventions are escalated automatically, based on member response or non-response, through one or more levels. For example, a non-response to an intervention may initially be escalated, after a certain elapsed time, to an alternate contact; on continued non-response, it may be escalated to an authorized caregiver; on further continued non-response, an exception may be generated, and the physician, pharmacist or other authorized provider may be alerted so that proactive measures may be taken, such as a personal phone call for coaching or triage intervention.

Interventions that involve personalized, human-interactions with individuals have so far been the most successful of the different approaches in current use—nurses or other qualified persons contacting individuals by phone or email on a regular basis to ask questions about heath, symptoms, side effects, adverse effects and so on. Coupled with these questions is some motivational interviewing designed to improve medication or treatment adherence. Due to the high cost of nurse-labor, these interventions are reserved for the sickest patients who might otherwise end up in the emergency room or hospital, and are not made available to the moderately-ill or healthy population. Additionally, a very large number of nurses would be needed to handle the latter population, at a time when there is a significant national nursing shortage, which makes this type of labor-intensive interventions impractical—it is inherently non-scalable to large populations.

Existing approaches to improving health can be categorized into: (1) nurse-labor-intensive, highly personalized 'case management' interventions for the highest-risk patients, (2) marginally personalized mass-produced 'disease management' interventions for the lower-risk patients, and (3) voluntary, self-service 'wellness management' programs for the healthy population. The highly personalized interventions have been shown to work well, and will likely do so for the lower-risk and healthy populations in improving medical adherence. However, because of the dependence on skilled nurse labor, these interventions are both expensive and non-scalable for these populations.

There is thus a need for an approach that can: (1) provide deeply personalized and motivational decision support and action support, (2) frequent interventions at low cost, and (3) be scaled-up to service the demands of a large population of healthy and medium-risk patients. This approach would keep the medium-risk patients from deteriorating towards high-risk and the healthy population from deteriorating towards medium risk. The objectives of this invention are to address these needs. Doing so would significantly reduce the estimated $100 billion annual costs of treating medical problems due to non-adherence in the US alone. In addition, improving adherence would recapture some of the $30 billion worth of unfilled prescriptions every year, and thus increase pharmaceutical industry revenues. Accordingly, a key goal of this invention is to provide a deep level of personalization and adequate frequency in the interventions, but at greatly reduced cost, through automation. A further goal is to eliminate the barriers to scalability, also through automation using readily available personal devices such as cell phones, as opposed to distributing special purpose devices.

U.S. Pat. No. 5,642,731 monitors the disease process and health of a patient undergoing drug treatment by using a microprocessor embedded in a drug dispenser to record a variety of clinical information such as symptoms, side effects, adverse drug reactions and so on. It seeks to improve disease management by capturing the date and time of the dosage, analyzing the data and downloading instructions to alter patient behavior in taking medication. This invention mechanizes the recording of when patients are opening the medication containers to ostensibly take their medicines, as well as the recording of clinical information, so it addresses the need for recording actual adherence. However, it does not address the motivational issues around taking the medications—patients may take the medicine as long as this invention is present and stop thereafter, or they may go through the motions of opening the container but not actually ingest the medications. Further, they may not accurately enter all the information required.

U.S. Pat. Nos. 6,234,964 and 6,770,029 describe a system that performs disease management in a fully automated manner using periodic interactive dialogs with the patient to obtain health state measurements, to assess the patient's disease and adjust therapy, and to give the patient medical advice. They also describe features and a metric based on subjective and objective health measurements that are used to tailor disease management interventions to individual patients. The system builds a profile of the frequency and patient's reasons for using the system, understanding of the disease, response to various treatments and preferences. The system interacts with patients through regularly scheduled sessions. This invention automates the traditional approach to following up on patients with chronic diseases—gauging health status, risks, clinical results, etc. and developing therapy-oriented intervention plans.

U.S. Pat. No. 6,974,328 describes an adaptive interactive teaching system for the remote education that selects and provides lessons based on a patient's profile. The lessons offer the patient information reflecting the patient's health, and offers the patient's healthcare provider information regarding the patient's study of the lessons, the patient's health, and the patient's medical appointments.

US Patent Application 2002/0169635 (Shillingburg) uses a custom device for transmitting messages, whereas the present invention uses cell phones or PDAs or whatever devices the individual already possesses, and requires no distribution of special hardware. The custom device described in the above application also has storage compartments for dispensing medication at the proper time. Adherence is measured in the above application by means of recording the time of opening of the medication compartment. The technical act of measurement described in the above application provides little by way of motivational value, whereas the 'self-report' technique is inherently designed to motivate the individual to improve adherence. The drawback is that self-reporting over-estimates adherence, but the motivational value, over time, is expected to reduce the over-estimation.

In general, the above-mentioned examples address specific parts of the overall problem and are lacking in the depth of personalization, matching to individual health states, frequency of intervention, obtaining and incorporating feedback from members and in adapting to the changing needs of the individual members. The system described hereafter introduces novel elements and builds on some of the existing solutions, or parts thereof, and provides a more comprehensive solution.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1 is a flowchart that shows the pre-registration environment in which the user accounts are pre-populated by a group administrator.

FIG. 2 shows the preferred embodiment of the user registration and subsequent intervention process.

FIG. 3 shows another embodiment of the user registration and subsequent intervention process.

FIG. 4 shows the user registration, data entry and storage process.

FIG. 5 shows the intervention plan generation, intervention delivery and response handling process.

FIG. 5A-1 shows the underlying user, conditions, phases and stages (or states) model.

FIG. 5A-2 shows the mapping to the user's current phase and stage in each condition.

FIG. 5B shows the condition-stage model.

FIG. 5C shows the stage response and progression model.

FIG. 5D shows a generalized stage response and progression model.

FIG. 5E shows the stage—intervention—content model.

FIG. 5F shows the user regimens and stages model.

FIG. 5G shows the process of generating a multi-day action plan from the users conditions and regimens.

FIG. 6 shows custom content model.

FIG. 7 shows the personalized user page layout.

FIG. 8 shows another embodiment of the mapping of member data to member characteristics.

FIG. 15 describes the intervention portal.

FIG. 16 is a flowchart that describes the intervention service model.

FIG. 17 is a flowchart that describes the escalation model.

FIG. 18 is a flowchart that shows the different analytics derived by the system.

FIG. 18A shows a set of analytic-driven alerts that enable management by exception.

FIG. 19 describes the system integration database.

FIG. 20 is a flowchart that describes how the credibility score is derived.

FIG. 21 shows the different stages of adherence.

FIGS. 22 and 23 are flowcharts that describe how the adherence slope is derived from two different sets of measurements.

FIG. 25 shows the inputs to the PurpleTeal Score.

FIG. 27 shows the phase-stage model for clinical trials.

DETAILED DESCRIPTION

Overview

Figure 9:
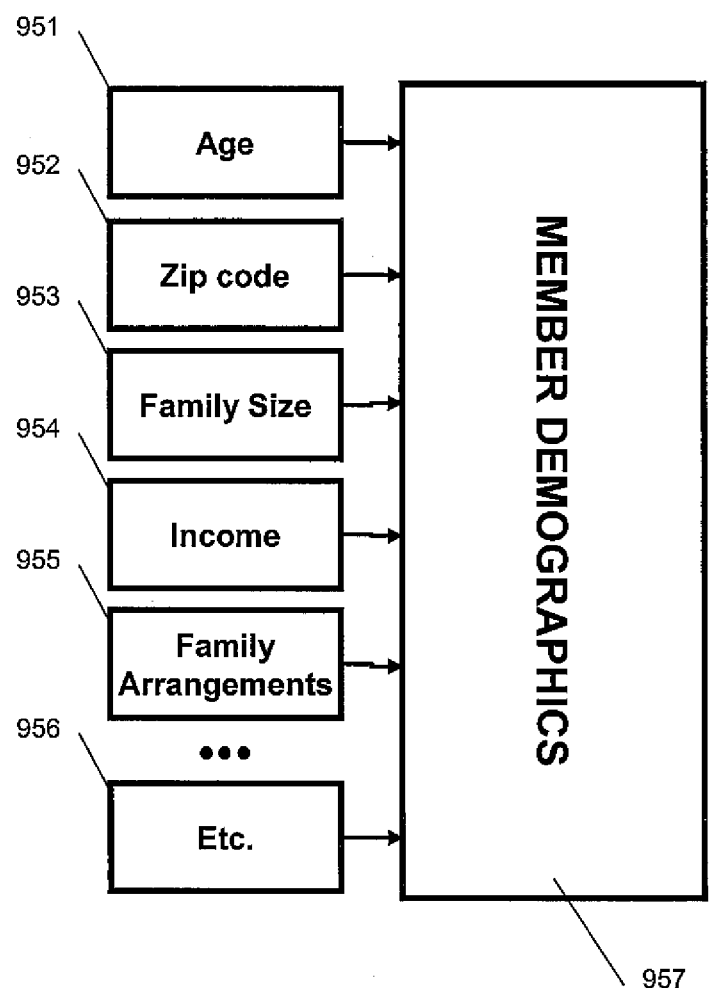
FIG. 9 shows the member demographics model.

Techniques and systems are described hereafter for reducing medical non-adherence by (1) providing a means for registering and profiling individual members, (2) using the profile to automatically generate and personalize a set of interventions, (3) categorizing, prioritizing and selecting the interventions, (4) incorporating the selected interventions into a personalized member user interface page, (5) serving the selected interventions to the member at the appropriate times via multiple channels, (6) observing and measuring member responses, (7) recording member responses in a database and analyzing the responses, (8) adapting the interventions, based on the analysis, to keep the member actively engaged, (9) escalating the interventions if the member response is inadequate and getting other authorized parties involved to persuade the member to respond, (10) updating the member's adherence profile based on analysis of the database, (11) providing member reports to authorized parties for purposes of paying member incentives, predicting and preventing member's utilization of high-cost healthcare services, etc., and (12) providing aggregate de-identified reports for purposes of predicting future risk reserve set asides, drug production and supply chain replenishment requirements.

Personalized Medical Adherence Management System Overview

A comprehensive system for reducing medical non-adherence is described. The system includes: (a) user data pre-population, registration and data entry (b) personalization (c) a portal to serve interventions via multiple channels, (d) methods to capture member adherence information, (e) a portal to receive adherence information and to provide secured user access, (f) a secured database to hold the member adherence and other records, (g) methods for handling response and non-response to interventions, and (h) individual and aggregate analytics. The system and its elements are described below.

DESCRIPTION OF FIGURES

FIG. 1 shows the major steps in the pre-registration process in a preferred embodiment. Starting with 1, in which a user with special Group Administration privileges (Group Administrator) logs in to the system. Group Administrators typically have read-write access to databases that pertain to the members of their particular group, and are authorized to perform the functions described below. Members are known to the system as 'Users' and will not be permitted by the system to access the other members' databases. Users will only be able to access their own databases. In the rest of this application, the terms 'User' and 'Member' are used interchangeably. Upon successful login, 2, the system initiates the Group Administrator's respective user interface, within which the Group Administrator can customize the Group's parameters, 2a, import user profile data, 3, from other databases, 4 and 5, to which he has access, and populate the user profiles for the group's members. The system then automatically sets up user accounts, including a randomized userid and password for each member and flags any missing data, 6, in the member's profile database. These flags and user accounts are secured in the pre-populated user profile database, 7. After setting up user accounts for each member, the system automatically composes and sends a welcome email to each member, 8, that includes an embedded link (url) to the user login page as well as the randomized userid and password.

FIG. 2 shows the steps in the registration, intervention and response process in a preferred embodiment. Following the receipt of the welcome email, 11, the member clicks on the embedded url, upon which the login page is displayed in a browser window. The member then enters the randomized userid and password provided in the email and logs in to the system. Upon successful login, the system initiates the user's working environment within the system and prompts the member to modify the userid and password, 12, to something not readily identifiable or associated with the member, yet meaningful to the User, so that they can be easily memorized. The system then reads the member-specific entries in the pre-populated user profile database, 14, composes the user interface display, 13, and displays the member's profile on a screen showing the pre-populated values and missing data flags. The member is given the opportunity to verify and/or update any of the profile information, 15, and prompted to accept the terms of use, privacy or other agreements. Upon agreement, the system updates the user profile, 16, in the user profile database. At this point, the member is considered to be a registered user of the system. Next, the system reads the member's profile data, makes assumptions about missing data and computes the member's most likely health status, stage of change and other characteristics, 18, and based on these dimensions, identifies specific interventions designed to elicit the actions recommended by medical guidelines, 17. The system then composes and displays the personalized 'Healthmonitor' page, 19, with which the user interacts and responds to interventions, 20, and logs out. At the same time, the system also sends the same interventions, 21, in the appropriate formats and versions, to the member via email, cell phone or other channels, such as a VRU (voice-response unit). The member can respond to interventions via any of the channels, 22; upon receipt of a response to a particular intervention, via any channel, the response is recorded, 23. Further or additional responses are recorded as well, and based on the rules established for each intervention, either the first or the latest response, within a pre-determined time window, may be accepted as the final response to that particular intervention. The system also records the member's interactions, such as login frequency, duration, content clicking, etc., commonly known as 'web behavior'.

FIG. 3 shows the steps in the method for improving medical adherence, according to another embodiment. Starting with 31, a member is first registered in the system and member data is collected and stored in the system in step 32. In step 33, the member data are mapped to several member factors that have a bearing on adherence behavior. In the subsequent step, 34, the member factors are mapped to expected behaviors from the member; these behaviors include adherence-related behaviors such as going for medical screenings, taking medications on time and so on. For example the Centers for Disease Control (CDC) states that 'the likelihood that a woman has had a mammogram at some time in her life varies by race/ethnicity. Hispanic women were the least likely to have ever had a mammogram, whereas non-Hispanic white women were the most likely.' Thus a Hispanic woman can be expected to have higher screening non-adherence, and will therefore need to be influenced to a greater extent to get a mammogram. This type of expected behavior is the basis for matching a set of specific interventions and incentives to the member in step, 35, that are designed to influence and enable the member to act (in this case, to get a mammogram). In step 36, the selected interventions and incentives are personalized, and relevant on-line community links are added and all the interventions are consolidated into a member-specific intervention plan. Personalization involves modifying the interventions to suit the member's preferences and requirements. An intervention has several parameters such as channel, tone, frequency, and so on—these are described in detail in a later section—these are preset based on the expected behaviors. In step 37, the intervention plan is converted into a set of instructions that transmit the interventions to the member through the portal. Once the interventions have been provided, the system monitors the responses in order to obtain member feedback and measure adherence, in step 38. This ends (39) the top to bottom flow. A number of analytics, 40, are provided, based on the member responses, feedback and measurements—which are described in a later section. One set of analytics provides the information to generate reports, 41, and trigger the escalation of interventions, 42. Based on member responses, interventions may be adapted, 43, in terms of further personalization, increased urgency in the tone of the content, intervention repetition, frequency, etc., in an attempt to elicit responses from the member. Also, based on the member responses, the member's profile information may be modified or updated, 44.

With reference to FIG. 4 which shows yet another embodiment of the member registration process, data inputs and storage in databases, the following are described. Members are first required to enroll and indicate permissions 51 for access to their health information, subject to the applicable laws; they are also required to enter certain personal and contact information. In addition, they are required to electronically indicate agreement with the terms and conditions of use, and to acknowledge that they understand the disclaimers. This is common internet practice. Following this, members are asked to enter detailed information about themselves 52, and answer some questionnaires 53 to 57. A calendar 58 is also provided for direct entry of events. The primary mode of data entry is through the internet, using a website 59. However, in cases where the member is unable or incapable of entering the data directly on the website, an assisted registration process 60 is invoked, in which a paper copy of the entry screens and questionnaires is provided, and a third party will specifically be authorized to enter the data into the system through the website 59. Alternatively, a member may enroll and enter the data for dependents. In the following, the words 'member', 'patient' and 'dependent' are used interchangeably. The entered data about a member is next stored in member-identified databases 62 to 69. With the proper permissions, authorizations and safeguards in place, some member data may be imported from external databases 70 such as those of health plans, employers or providers, using the integration database 71. These databases may optionally be consolidated into a single member database.

FIG. 5 illustrates the intervention, response and adaptation process in the preferred embodiment. At pre-determined times, the system automatically initiates a scan, 81, of the user database, 83, which contains the user's profile data and other imported data, and compares it to published medical guidelines for screening, prevention, diagnosis and treatment, 82 which are stored in a phase-state database 80 which comprises conditions, regimens and processes. The phase-state database 80 may have hundreds of conditions broken down to phases and stages, and will be continuously maintained—as and when new treatments are recommended or new conditions are added by recognized medical authorities. If a set of disease states is updated in the phase-state database 80, while the patient is already in a particular stage of the previous version of the same disease, as part of the migration, the system has rules for dealing with patients in different stages and switching those patients to make use of the updated phase-state database 80 where appropriate.

The system then identifies the user's relevant conditions and stages. The system also scans the user's database to identify regimens, 97, applicable to the user, such as medications, readings, and other health or self management regimens. Based on this information, the system then develops a personalized user intervention plan, 84, with specific interventions based on the user's medical conditions and states, along with the applicable channels, response options and the date and time at which each intervention is to be sent. Interventions may also include relevant web content and custom content, 87, as well as elements of specific health programs, 85, such as a diabetes management program. In the next step, the system automatically sends the interventions, 86, along with the relevant custom content links and/or pre-configured search words, at the appointed date and time, via the selected channels, and waits for user interactions, responses or measurements, 88. When responses or measurements are received, they are automatically entered into the user database, 89. If user responses are not received within a pre-determined elapsed time interval, the interventions are escalated, 90, to alternate contacts or caregivers. With continued non-response to interventions, based on pre-determined rules, exceptions, 93, are generated and handled by alerting other authorized complementary services or organizations, 94, such as health coaches, disease management nurses, physicians' offices or pharmacies, and informing them that the user may need personal attention. At pre-determined intervals, or as and when responses or measurements are received and stored in the user database, the system analyzes the responses or measurements, 91, then, based on pre-determined rules, automatically adapts the respective interventions, 92, in terms of frequency, repetition, or content, in an effort to maximize the user's engagement with the system.

The user can also adapt the interventions manually using the intervention adaptation user interface, 95, to make similar intervention adaptations.

FIG. 5A-1 illustrates the user-condition-state model that is the basis for generating the user's intervention plan at a particular time, in the preferred embodiment of this invention. Each User, 101, can have multiple conditions, 102, 106, 107, and each condition has multiple phases, such as a screening phase, 103, a diagnosis phase, 104 and treatment & follow-up phases, 105. Each phase is comprised of multiple stages in a pre-determined sequence for each condition: 1-8, 9-15, 16-21, and so on. These stage numbers are only representative examples to illustrate the sequence; the actual number and sequence varies for different conditions. At any point in time, a particular User may be in different phases and stages for different conditions that the User may have. The User may be in the Screening Phase for a particular condition, because of an 'At-Risk' status by virtue of the User's age, gender, ethnicity, family history, lifestyle, warning signs, and other profile factors. In this phase, the User is required to be screened as recommended by medical guidelines. For a different condition, the User may be in the Diagnosis Phase. In principle, this should occur if and after a User screening for the condition is positive, but it may also happen because the User experienced symptoms or the condition was discovered incidentally while receiving medical attention for some other problem. After Identification as 'at-risk' through screening, a formal diagnosis is recommended by medical guidelines. After the User gets a formal diagnosis, the Treatment & Follow-up Phase begins, also per medical guidelines. There is a natural progression from screening to diagnosis to treatment and follow-up. In order to properly identify a user as being in one of the phases in each of the applicable conditions, and to further identify the user as being in a specific state within each phase, user input is needed. Initially, the system assumes that the user is in the 'Screening' phase, but the system provides a menu, for each condition where the user can specify the actual current phase and state. The system then proceeds to the actual phase and state and begins the interventions from that point.

FIG. 5A-2 shows how the system initially determines the current phase and state of the user with respect to each of the conditions applicable to the user in the preferred embodiment. As described above, for each condition, there is a screening phase, 731, a diagnosis phase, 732 and a treatment & follow-up phase, 733, comprised of stages 1 to 8, 9 to 15 and 16 to 21, respectively. As mentioned above, the actual number of stages in each phase is only shown for illustrative purposes; they will most likely be different for each condition. The mapping to the user's current stage in a particular condition is carried out as follows: for each applicable condition, the user is presented with a questionnaire having questions, 734 to 740. Each question is internally mapped to a certain stage in the condition-phase-stage model; for example, 'I have recently been diagnosed' is mapped to the last stage in the diagnosis phase. For a particular condition, if the user selects this question, the system immediately maps the particular user's state to the last stage in the diagnosis phase for that condition. Similarly, the system maps individual users to their respective current stages for their respective applicable conditions, based on the questions selected. It should be noted that some of these questions that serve to gauge the change-readiness or 'stage of change' of the user with respect to diagnosis or treatment. For example, a user who clicks on 'I need to start treatment within a month' is more advanced stage of change with respect to getting treatment for the applicable condition than a user who does not.

In the preferred embodiment, in case external user data are available, such as a HRA (Health Risk Assessment), 742, or a PHR (Personal Health Record), 743 or lab data, 744 or health insurance or pharmacy claims data, 745, the system has an analytics routine, 741, to identify a user's applicable conditions as well as the current phases and stages. The data from these sources may contain diagnosis codes (ICD) that indicate diagnosed conditions, common procedure terminology (CPT) codes which indicate screenings or treatments, or national drug codes (NDC) which indicate drug prescriptions, etc. that are the inputs to the analytics routine. For example, if a CPT code for diabetes treatment and an NDC code for a diabetes drug exist for a user, it may safely be concluded that the user is in the treatment and followup phase.

In the preferred embodiment, with reference to FIG. 5B, within each phase, there are diagnosis phase stages, 111, for example, that comprise a sequence of events or actions (stages 9 through 16). For illustrative purposes, this figure shows the sequence for a doctor visit for the purpose of diagnosing whether the User has a cholesterol problem, but this is generally applicable to other event sequences. The diagnostic test for cholesterolemia involves taking a venous blood sample from a fasting patient and running lab tests for total cholesterol, LDL (low density lipoprotein), HDL (high density lipoprotein), and Triglycerides, commonly referred to as a 'lipid panel'. It is very important for the patient to be fasting for 10 to 12 hours before the blood is drawn, and it is not uncommon for the patient to forget to do that, thus requiring that the appointment be rescheduled. It is also not uncommon for the patient to completely forget about the appointment, especially if it is later in the day, due to work-related or other pressures and priorities. In this example, the present invention seeks to improve the chances of a successful visit, as scheduled, by planning and sending, at the appropriate date and time, reminders to perform the required actions. Once the User schedules and appointment with the doctor and records the date and time in the system, 112, the system waits until the evening before the appointment, at a time set by the User (or predetermined by the system), and sends a 'Begin Fasting Reminder' to the User, 113. This reminder may be in the form of an email or cell phone text message that informs the User that he has a cholesterol check on the next day and that he should begin fasting within an hour. The specific messages are customizable and are typically pre-programmed in the system. On the morning of the appointment, at a time specified by the User or at a time pre-determined by the system, a 'Cholesterol Appointment & Fasting Confirmation' reminder, 114, is sent in the same manner. The system then waits for a pre-determined time (or as specified by the User) after the appointment event, 115, and sends another message to confirm that the User attended the appointment, 116, and if known, to enter the results or diagnosis, 117. Based on the User's response, the system then transfers the User to the Treatment phase (in case the diagnosis is positive), 119, or to a 'Wait Stage' for 12 months, 120, or some specified time interval (in case the diagnosis is negative), and then restarts the same cholesterol evaluation sequence.

In the preferred embodiment, as shown in FIG. 5C, with each of the above interventions and reminders, User responses or non-responses may trigger other actions in the sequence or transfer the User to a different sequence of stages, based on pre-determined rules. A User who is initially at a particular stage 'Stage I' with respect to a particular condition gets an intervention, 134, and may respond with a 'Yes', 138, or 'No', 135, or may not respond at all (non-response, or NR), 141, within the allocated time period. Based on pre-determined rules applied to responses to interventions for 'Stage I', the User is transitioned to 'Stage I±J', 136, or Stage I±K, 139, respectively. For example, if the initial stage (11) is one where the User is reminded about the appointment and is asked whether he has been fasting for at least 10 hours, thereafter, the User's responses determine the next stage or sequence. If the User responds 'Yes' (i.e., he has been fasting), then the system transfers the User to the stage (12) in which the system waits for the appointment to be over, and then subsequently moves to the appointment confirmation stage (13). If, however, the User responds with a 'No' (i.e., he has not been fasting for at least 10 hours), then the system transfers the User to the beginning of the sequence, or stage 9, where he has to reschedule the appointment and restart the sequence. If the User does not respond with either a 'Yes' or a 'No' within a pre-determined time, the system automatically initiates an escalation cycle, 142.

In the preferred embodiment, FIG. 5D shows a more general picture of the stage-response and progression model in which a User, has at least one condition with screening, 151, diagnosis, 152, and treatment/follow-up, 153, phases, and it is assumed that the User is initially at a particular stage 'Stage I', 155, with respect to this particular condition. Based on rules applied to responses to interventions for 'Stage I', the member can be promoted to 'Stage I+K', 156, or demoted to 'Stage I−J', 154. For example, if the condition is Cholesterolemia, and the User is in Stage 12 (let's say, lab test for cholesterol), the member can either transition forward to Stage 18 (treatment) because the tests were abnormal, or backward to Stage 1 (screening) because the tests were normal. These transitions, in general, is effected through stage-specific 'Promote Triggers', 157, 158, or 'Demote Triggers', 159, 160, which define the rules by which a User may be transitioned forward, or 'promoted' to a forward stage, or transitioned backward, or 'demoted' to a backward stage. In general, the stages to which the User is transitioned may be in any phase of the condition.

FIG. 5E shows the Stage-Intervention-Content model in the preferred embodiment. A stage, 171, is comprised of an intervention, 172, which has several attributes, 174 to 179. The purpose of an intervention is to successfully convey a timely action-oriented message to the User, with relevant content, both custom, 182, and derived from the web, 183. Interventions can be of different types 174 (influencing or enabling or measuring, mandatory or supplementary, time-based, count-based or day-based), convey different messages 175, use different channels 176, at different timings 177, with certain frequency 178, with the proper tone 179 that conveys urgency or importance, and other aspects. Custom content, 182, is typically accessed by the User by clicking on the appropriate url links provided in the Personalized User Page described in a later section. A separate browser window displays the selected content. Similarly, web content, 183, is displayed in a separate browser window during a User session as and when the User clicks on any of the retrieved links displayed in the Personalized User Page. Web content links are retrieved from multiple sources, such as from search engines, 184, like Google, 186, Yahoo, 188, or other engines, 190, or from certified content sources, 191, like WebMD, 193, Mayo Clinic, or other sources, 195. When the User views the current intervention, these links are retrieved in real-time, based on pre-configured search strings, 185, 187, 189, 192, 194, that are customized for different search engines or content sources. Interfaces are provided both for search engines, 184, and certified content sources, 191, that present the content to the User in separate browser windows.

In the preferred embodiment, FIG. 5F shows the regimens that pertain to a User and the stages in each regimen; this is similar to the condition-stage model discussed above. A particular User, 301, in addition to having a number of conditions, can also be required to participate in a number of regimens such as taking medications, 302, 303, 304, participating in a diet program, 305, participating in an exercise program, 306, taking blood pressure readings, 307, taking fasting glucose and post-lunch glucose readings, 308, 309, and taking the body weight, 310. Each of these regimens has a sequence of stages through which the User passes, in a manner similar to that discussed for conditions, above. For example, the regimen of taking 'Medication 1' begins with a Doctor's prescription, then proceeds to the actions to fill the prescription at a pharmacy, then to the actions of taking the medication daily at the appointed time, then watching for the number of doses to fall below a certain number, then refilling the prescription, and so on.

In the preferred embodiment, FIG. 5G shows the derivation and consolidation of time-bound action plans for a User, from the overall set of conditions and regimens that pertain to the particular User, 321. Action time windows, 335, on a daily, weekly, or 'N-day' basis, are preset in the system, with either the current date or the Sunday or Monday of the current week, or a User-specified Date as the Start Date, 334, for the windows. The window can be changed at any time, by the system or by the User, and multiple windows can be operational at any time. Based on the specific stages of the User in each of the conditions, 322, 323, 324, or regimens, 325 to 333, the system identifies the specific actions that need to be performed in the different time windows, and consolidates these actions into window-limited Action Plans, 336. These action plans are then displayed by the system in the weekly/daily calendar section of the user interface. Action Plan consolidation windows can also be user-specified or optimized algorithmically. The user can specify whether action plans can be consolidated or not. This allows for combining multiple visits into a single visit, based on rules such as: the visits are valid within the respective consolidation window, the visits are to the same doctor, the 'combine visit' option is selected by the user, and so on. Other actions can also be consolidated automatically based on rules; for example multiple daily reminders can be consolidated into a single reminder in order to simplify user interaction and reduce irritation with multiple messages within a short time period.

FIG. 6 shows the Custom Content Model. Custom Content 613 is comprised of the raw information that is to be conveyed to the member. The information can pertain to a topic 601, be related to a disease 602 or disease stage 603, or to a stage of change 604. The information may be in a certain language 605 and at a 'less or more than $8^{th}$ grade' readability level 606. The information may be oriented towards certain demographics 607, such as pictures of children, young adults, middle-aged people etc. that children, young adults etc., would better relate with. The information may also be age-appropriate such as avoiding intensely graphic images for those below 13 years of age. The information may also be present in multiple formats 608 in order to facilitate transmission via multiple channels. The content may also be ranked 609 in terms of usefulness to members, based on collective feedback. Special content pertaining to a clinical trial may also be included, 610. Content may be imported from external databases 611 using the integration database 612. The custom content may also be stored in a database, 614.

FIG. 7 shows the Personalized User Page in the preferred embodiment. The purpose and layout of this page is to present information to the User in a way that compels a response and/or action. In addition to the typical banner health alerts and general messages, 721, and User account greeting and administrative functions, 722, the page displays several other elements unique to this invention. For example, a weekly calendar area, 724, displays specific actions to be taken on a day to day basis—on each day of the current week. Clicking on any of the daily action items displayed here opens a slide-down display area, 725, that displays more detailed information about the selected action item, where the user can learn more about the action item, how to perform it, why it is important, what to ask the doctor regarding this action item, and so on. Each type of information is presented in separate tabs (e.g. Learn More, How to, Why do it, Ask the Doctor, Products), 726, to facilitate User navigation. The User is not required to peruse any of this information, but it is there if the User needs it, without any effort by the User to search for the information on the internet. There is no technical limitation on the number tabs and in fact, more tabs can be added dynamically, for example to display information about suitable products and services. The tabs can also be reordered to reflect a pre-determined priority. Another key area is the User's Health Conditions display area, 727, which provides a snapshot showing the User's various conditions and their respective placement in the condition-phases of: symptoms, screening/prevention, diagnosis or treatment & follow-up. Clicking on any of these conditions displays the next step in managing that particular condition in the slide-down area, 725. This presents a consistent, intuitive user interface that allows the User to see, at a glance, what conditions he has, in what phase they are, in which stage is each condition, and what specific actions he needs to take immediately. In addition, a large amount of relevant information, organized to support decision-making and action, is readily available on a click. On the left side of the display, there is a graphical 'meter' display, 723, that provides real-time feedback to the User on his adherence performance, in the form of proprietary 'PurpleTeal Score'. A glance at the meter quickly tells the User how well he is doing in terms of managing his medical conditions. Finally, on the bottom left side of the display, hard-coded buttons, 728, are provided as 'Quick Links' for commonly performed tasks like changing the time zone of the User or updating profile data or User preferences.

FIG. 15 shows the intervention portal and the elements that interact with the portal. The portal 1553 provides access to members with an internet terminal 1563 for initial enrollment, registration and data entry. Once member data has been entered, the system generates a personal page 1555. A member, accesses the portal using an internet terminal, views his/her personal page and makes modifications 1551 to interventions or links, which are then recorded in the member history database. Once the modified personal page is accepted, interventions begin per the member's personal plan. Interventions may be served by the portal through multiple channels such as SMS 1552, caregivers 1557, devices 1562, internet (email) 363, PDA's 1564, or voice 1565. The portal also serves as the conduit for online communities 1556 and external links to web content 1554. In addition, links to a custom content database 1567 can also be provided. Measurements may also be received via the channels shown with double-headed arrows linked to the portal and these measurements in the form of member web behavior 1558 and member responses to interventions 1561 are recorded in the operational database 1559, and later stored in the member history database 1560.

FIG. 16 is a flow chart of the intervention service model. The member intervention plan 374 makes intervention entries into the member calendar 373 that identify specific interventions, their timing and other parameters. The 'Time Stamp' algorithm 372, based on the system calendar-clock 371 and the member calendar, determines the appointed time $T_0$ for a particular intervention and passes the command to the 'Open Intervention' algorithm 376 that opens the particular intervention that is drawn from the intervention database 375. If the intervention is time-based, the algorithm records the time $T_0$; if the intervention is count-based, it records the zero count $N_0$; if the intervention is based on number of elapsed days, then the day count is zero'd. i.e. $D_0$. The 'Record & Send' algorithm stores the intervention record in the member history database 384 and the portal 378 then sends the intervention to the member. Member responses 379 are received and recorded in the operational database 380. The 'Open Intervention' algorithm continues to monitor the elapsed time, count or days as applicable to the intervention. At the appointed time $T_1$, the system checks the operational database to see if there has been a response to the intervention 381. Similarly if the appointed count is $N_1$ or appointed days are $D_1$. If there has been a response, the intervention is closed 383. If there has been no response, the system invokes the escalation process 382.

FIG. 17 describes the escalation process that begins 391 when there has been no response to an intervention at the first appointed time $T_1$, first appointed count $N_1$, or first appointed day $D_1$, depending on the type of the intervention. The appointed times $T_1, T_2, T_3, T_4$, appointed counts $N_1, N_2, N_3, N_4$, and appointed days $D_1, D_2, D_3, D_4$, are part of the set of member parameters 393 that are stored in the member history database 392. Once the system has passed control to the escalation process 391, a series of escalations 397 to 405 are implemented as described below. Three levels of escalation are shown for each type of intervention, to illustrate the process, but multiple and different numbers of escalations are possible for different intervention types. The 'Open Intervention' algorithm calculates the elapsed time $(T-T_0)$ 394, elapsed count $(N-N_0)$ 395 and elapsed Days $(D-D_0)$ 396, depending on the type of intervention. For a time-based intervention, when the elapsed time has exceeded the member parameter $T_2$, the tone of the intervention is escalated to positive 399, then to a 'bald' tone 398 when it has exceeded the member parameter $T_3$, and finally, when it has exceeded the member parameter $T_4$, the caregiver is notified 397. As an example, a reminder intervention (time-based) may begin with a neutral 'It is time for your morning medicine' at $T_0$, then escalate the tone to a positive-polite 'If you haven't taken your morning medicine already, please take it now', then to a bald 'Please take your morning medicine now'. In a similar manner, for a count-based intervention, the number of times the intervention has been repeated $(N-N_0)$ is tracked; at $N_2$, the intervention is sent to the alternate phone provided by the member 402, at $N_3$, the intervention is sent to the alternate contact (provided by the member, and could be an online mentor) 401, and at $N_4$, the caregiver is notified 400. Similarly, for day-based interventions, at $D_2, D_3$ and $D_4$ the escalation is to change the intervention frequency 405, notify the caregiver 404 and notify the provider 403, respectively.

FIG. 18 shows the different analytics derived by the system. There are two major types of analytics—member analytics 418 and aggregate analytics 422. The member history database 421 is the main source of data for the aggregate analytics. Aggregate analytics are based on de-identified data about multiple members who may belong in a group, and may produce reports such as an employer summary 411 (summarized data about employees), drug consumption report 412 (estimating how many units of a drug have been consumed), or ad-hoc reports 413 as required by an authorized group representative. The member history database is also used for profile update analytics 423, which then update the member databases 424 to reflect new or changed profile information.

As mentioned above, the member history database drives individual member analytics such as member adherence stage 420, member adherence slope 419. Further, using member external data 414 that has been stored in the integration database 415 in conjunction with the member history database, the system calculates the member credibility score 416. The member PurpleTeal score 417 is a combination of the member adherence score, adherence stage and member credibility score. The member PurpleTeal score drives the member analytics 418. Some examples, such as the incentive tracker 425 and member predictions 426 are shown. All analytics are recorded in the report logger 427. In order to provide real-time feedback to the User, in a readily understandable form, this invention also presents the User's PurpleTeal score in the user interface on a dashboard resembling a meter.

FIG. 18A describes a 'Response Down-Trend' analytic that can be used for exception-based interventions to prevent unnecessary hospitalizations or ER visits. For a User with an advanced disease, such as diabetes, 1851, it is well known that taking medications regularly is important to keep the disease under control and stave off complications. However, many patients do not adhere well to their medication regimens, and some even stop taking their medications for various reasons. When such a User stops taking medications, 1852, for a period of time as indicated in the figure, the disease deteriorates, and as time progresses, becomes worse, eventually to the point of suffering complications, 1853, that may require expensive hospital visit, 1854 or an Emergency-Room visit, 1855. This deterioration may take several weeks, which provides time for multiple interventions to progressively try to get the User to resume taking the medications and avoid an expensive hospital or ER visit. In this period of time, the system tracks an analytic called the 'Response Down-Trend', which is a trend line of the User's responses to medication reminders over a number of days or weeks. Multiple levels or thresholds of this trend are preset, and when these levels are reached by the user, alerts are automatically generated and sent to appropriate parties. For example, we may preset three levels, namely, Level 1, 1856, Level 2, 1857 and Level 3, 1858, of the response down-trend analytic. On a daily basis, the system calculates this analytic and checks whether any of these levels have been reached by the User. When the user reaches Level 1, the system automatically send an alert, 1859, via email or cell phone or other available channels, to the User or the Caregiver, with a message: 'User is at Moderate Risk for Complications and must resume taking medications'. Hopefully the user resumes taking the medications at this point and avoids complications. If the user does not resume taking the medications, the system eventually detects the attainment of level 2 and send an alert, 1860, via multiple channels to the Caregiver or authorized $3^{rd}$ parties like health coaches or disease management nurses, informing them that the 'User is at high risk for complications' and further includes an instruction, 1862, to 'Counsel the User to resume medications and try to avoid complications'. Similarly, at level 3, alerts are sent to physicians or pharmacists, 1861, who have more in-depth medical relationships with the user, with the same instruction, 1862. In this manner, the efficient principle of 'management by exception' is implemented, in which only those users who have triggered the preset thresholds receive expensive human attention, not everyone, by routine, whether they need it or not.

FIG. 19 describes the system integration database 434. This database serves as the staging area for data being imported or exported for purposes of integration between systems. Clinical and other member data from external databases 432 are imported through an external access point 433, but only after clearance from the authorization & release module 432. Data housed on public external databases 435 are directly imported into the integration database after the usual anti-virus and other integrity checks. Another integration point 437 transmits de-identified member-specific data to incentive payment systems 436 that may be operated by employers, who are not allowed to see individual member identifying information, by law. These incentive payment systems release the appropriate funds to specific members who meet the incentive requirements. Yet another external access point 438 is used for exporting data, subject to the required authorizations and releases 439, to external databases 440 that are operated by health plans and others who are authorized to view individual member information.

FIG. 20 describes the process by which the credibility score is derived. This is done on a continuous basis, being triggered whenever new information is recorded in the member history database 451. The credibility score is used to adjust the self-reported adherence information to compensate for the known over-estimation bias in self-reports. One determinant of the credibility score is the level of member engagement, as indicated by the number of member responses to interventions. The source of data for this process is the member history database 451, from which the responses to interventions 452, 453, 454 are evaluated. If there is no response, the item score is a −1, and if there is a response, the item score is a +1. The number of non-responses 455, 457, 459 and the number of responses 456, 458, 460 are summed to provide one component of the credibility score 464. Another component of the credibility score comes from the member web behavior 466, which also indicates the level of the member's engagement with the system at a user-interface level. The more engaged the member, in terms of clicking on the links provided, participating in online communities, and so on, the higher this component of the credibility score. A third component of the credibility score comes from the member's clinical information which typically resides in external databases held by providers and physicians and is imported into the integration database 461, assuming the required permissions and access rights are in place. The specific clinical data of interest are the key indicators of disease control, such as serum cholesterol levels, glycosylated hemoglobin for diabetics, and so on. Regardless of the member's adherence self-reports, the true test is whether the desired health outcomes are achieved. If a member's diseases are being controlled, the relevant disease indicators should be within normal ranges. If these indicators are not within normal ranges 463, the item score is a −1, and if they are within normal ranges 462, the item score is a +1. The item scores are summed and incorporated into the credibility score. The underlying assumption is that higher adherence, if self-reported by the member, should be reflected in the clinical results that are closer to normal values. There are situations where a particular drug, even if taken exactly as directed, may not produce the desired clinical results; these are treated as exceptions. The credibility score determines an adjustment factor 465, which is qualitatively set at high, medium or low, and the adjustment factor is used to reduce the self-reported adherence responses by 0, 25 or 50 percent, as an example. These are system parameters that can be set externally.

FIG. 21 shows the different stages of adherence. Adherence does not usually occur in one big step, going from a stage of poor adherence to full adherence, but proceeds in stages. For screenings, a member's Stage 1 475 would be simply to take a Health Risk Assessment (HRA) that would, among other things, indicate which screenings the member should go in for. Following that, one objective of this invention is to influence and enable the member to proceed onward to Stage 2 474 and actually set up the screening appointments, complete the screenings in Stage 3 473, and continue periodic screenings per clinical guidelines in Stage 4 472. For prescriptions, in Stage 1 476 the member needs to get the required drugs prescribed by the doctor or nurse, in Stage 2 477 the member has to fill the prescriptions, and in Stage 3 478 the member has to continue to refill the prescriptions. Once the prescriptions have been filled or refilled, the member proceeds to the consumption part of medication adherence. In Stage 1 479 the member takes whatever drugs he/she is currently taking, but on more days, in order to improve adherence in this dimension. Once the member has become habituated to taking the drugs on a regular basis, the focus moves to the dosage strengths. In Stage 2 480 the member is enabled and measured to take the drugs at the right dosage strengths. In Stage 3 481 the member is enabled and measured to take the drugs at the right time. Finally, in Stage 4 482 the member is influenced to take more of the drugs in their regimens. Eventually the member takes all of the drugs prescribed, not just a subset, takes the drugs at the right time, at the right dosage strengths and on all days as prescribed.

FIG. 22 describes a simple method by which the adherence slope is derived from one set of measurements that are responses to a question such as 'Have you taken your dose?' that requires a 'Yes or No' or '1 or 0' answer. The member history database 491 contains the historical responses to this measurement, including the current value 493 and the previous value 494. If the current value is a 'No' and the previous value is a 'Yes', the adherence slope 495 is deemed to be less than zero. If the current value is a 'No' and the previous value is also a 'No', the adherence slope 496 is deemed to be zero. If the current value is a 'Yes' and the previous value is either a 'Yes' or a 'No', the adherence slope 497 is deemed to be greater than zero.

FIG. 23 describes the method by which the adherence slope is derived from a different set of measurements, namely, a question such as 'How many doses did you miss in the last D days?' that requires a numeric response, typically 0 to 9. The response is converted to an D-day adherence rate 512. The member history database 511 contains the historical responses to this measurement and the calculated adherence rates. The rate is considered to be low if more than 50 percent of the doses are missed (typically three out of six doses in a 3-day period), medium if between 18 percent and 49 percent of the doses are missed (typically two out of six doses in a 3-day period), and high if only 17 percent or less of the doses are missed (typically one or none of the six doses in a 3-day period). If the current rate is low 514 and the previous rate is low 515, medium 516 or high 517, the adherence slope 526 is deemed to be less than or equal to zero. If the current rate is medium 518 and the previous rate is high 519 or medium 520, the adherence slope is also deemed to be less than or equal to zero. If the current rate is medium 518 and the previous rate is low 521, the adherence slope 528 is deemed to be greater than zero. If the current rate is high 522 and the previous rate is low 523, medium 524 or high 525, the adherence slope is deemed to be greater than zero. In this figure the previous adherence rates are shown in dotted boxes.

Figure 24:
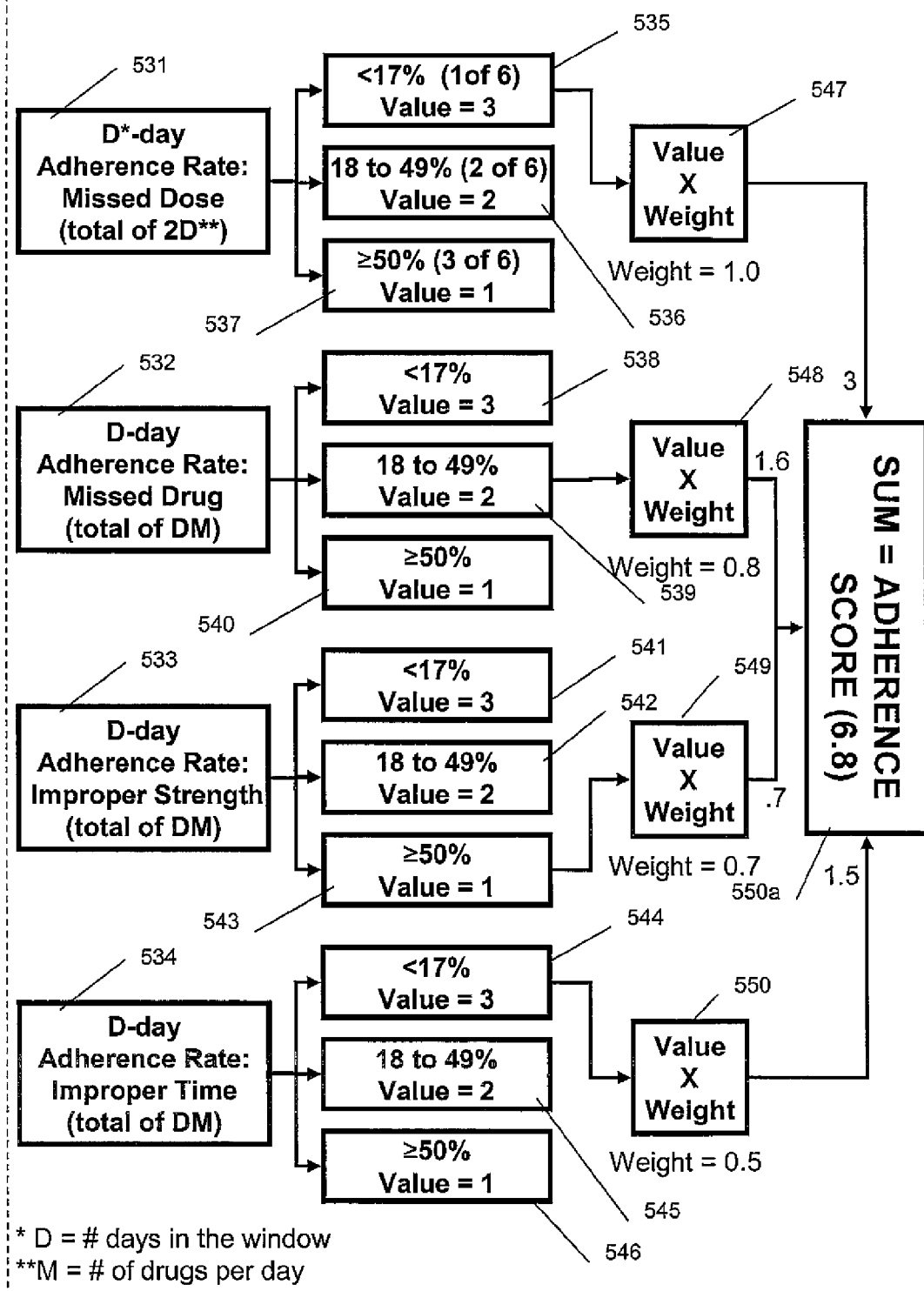
FIG. 24 is a flowchart that describes the Adherence score calculation.

FIG. 24 describes one embodiment of the Adherence score calculation method. The adherence score 549 is calculated on a periodic basis, or when triggered by a measurement of the D-day adherence rate, in terms of missed dose 531, missed drug 532, improper strength 533, or improper time 534. The missed dose adherence rate is measured in terms of how many doses were missed out of the 2×D doses in a period of D days, assuming two doses per day, which is typical. This can easily be adjusted for members who have to take drugs once a day or more than twice a day by setting the member parameters accordingly. For the missed dose adherence rate, a value 535 of 3 is assigned if the rate is less than 17 percent, or less than one dose missed in the three-day period. Likewise, a value 536 of 2 is assigned to adherence rates between 18 and 49 percent, and a value 537 of 1 to adherence rates greater than or equal to 50 percent. Depending on the member's current adherence rate, the appropriate value is chosen, either 1, 2 or 3, as stated above. The value is then multiplied by a weight 547 and the result becomes one of the components of the adherence score 550a. Similarly, the missed drug adherence rate is also assigned values 538, 539, 540 of 3, 2 and 1, representing the rates of less than 17 percent, between 18 and 49 percent, and greater than or equal to 50 percent, respectively. In the same manner as with the missed dose adherence rate, depending on the member's current adherence rate, the appropriate value, 1, 2 or 3 is chosen, the value is multiplied by the respective weight 548 and the result becomes another component of the adherence score. The same method is used to calculate the other two components of the adherence score, namely improper strength adherence rate 533 and improper time adherence rate 534.

FIG. 25 shows the inputs to the Member PurpleTeal Score 565. The PurpleTeal score is a figure of merit that characterizes a member's overall health behavior, similar to a person's credit-rating. It is a combination of several scores: screening adherence 551, medication adherence 552, treatment adherence 553, credibility 555 and wellness adherence 563, and indicators: stage of adherence 554, response to interventions 556, response to content 557, community participation 558, calendar utilization 559, function utilization 560, web behavior 561, self management 562, and other indicators included in 'Etc.' 564. The scores and indicators for a particular member are combined to result in a single alphanumeric rating to yield the member's PurpleTeal score.

Figure 26A:
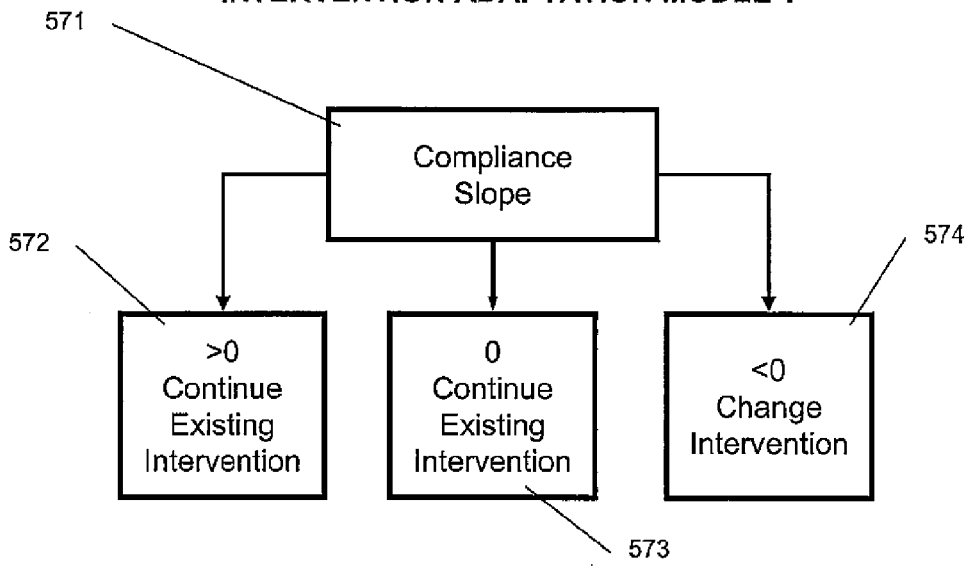
FIG. 26A describes the intervention adaptation model.

FIG. 26a describes one embodiment of the intervention adaptation model. In this embodiment, the underlying premise is if an intervention is working, it should be continued and interventions that have stopped working should be changed. The decision may be driven by the adherence slope 571, as shown in this figure, but other indicators such as the trend in adherence slope may also drive the decision. If the slope is greater than zero 572, or zero 573, the intervention is working and will not be changed. If the slope is less than zero 574, the intervention is not working and will be replaced or changed in some way.

Figure 26B:
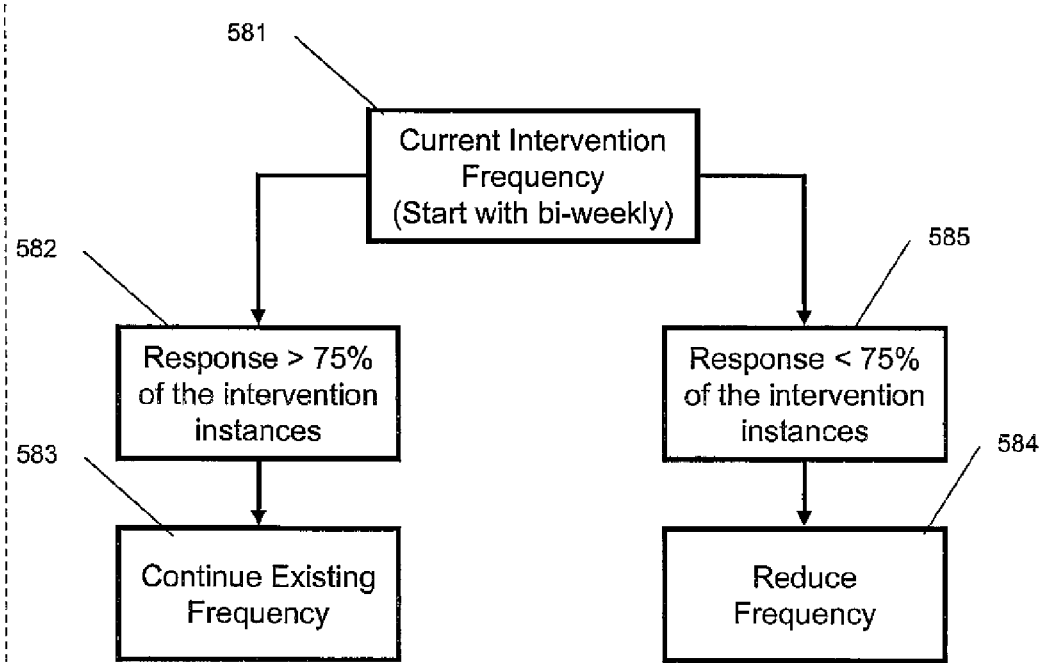
FIG. 26B describes the intervention frequency adaptation model.

FIG. 26b describes one embodiment of the intervention frequency adaptation model. In this embodiment, the underlying premise is that if a member does not respond to interventions (such as adherence measurements) every time, then the interventions are too frequent and should be made less frequent. There are other reasons for not responding, but in this embodiment, non-response is the criterion. Interventions are initially served at the current frequency 581, typically bi-weekly. If the member responds to instances of an intervention more than 75 percent of the time 582, the frequency is deemed to be matched to the member's preferences and the intervention frequency is continued 583. If the member response is less than 75 percent of the time, the intervention frequency is reduced 584.

In another embodiment of the present invention, FIG. 8, shows the mapping of the data in the member database(s) 40 to certain member 'Factors' 841, the raw data collected about a member is correlated with the factors. The member factors are determined from these correlations and subsequently stored in the factor database(s) 842.

For this embodiment of the present invention, in FIG. 9, some of the member demographical data elements are identified. The intent in this and the following figures is to provide clarity by limiting the number of data elements or factors shown; there may be additional data or factors that are included in the 'Etc' category; this should not be viewed as a limitation of any kind. Some examples shown include: Age 951, Zip code of residence 952, Family size 953, Household income 954, Family arrangements 955, etc. 956.

Figure 10:
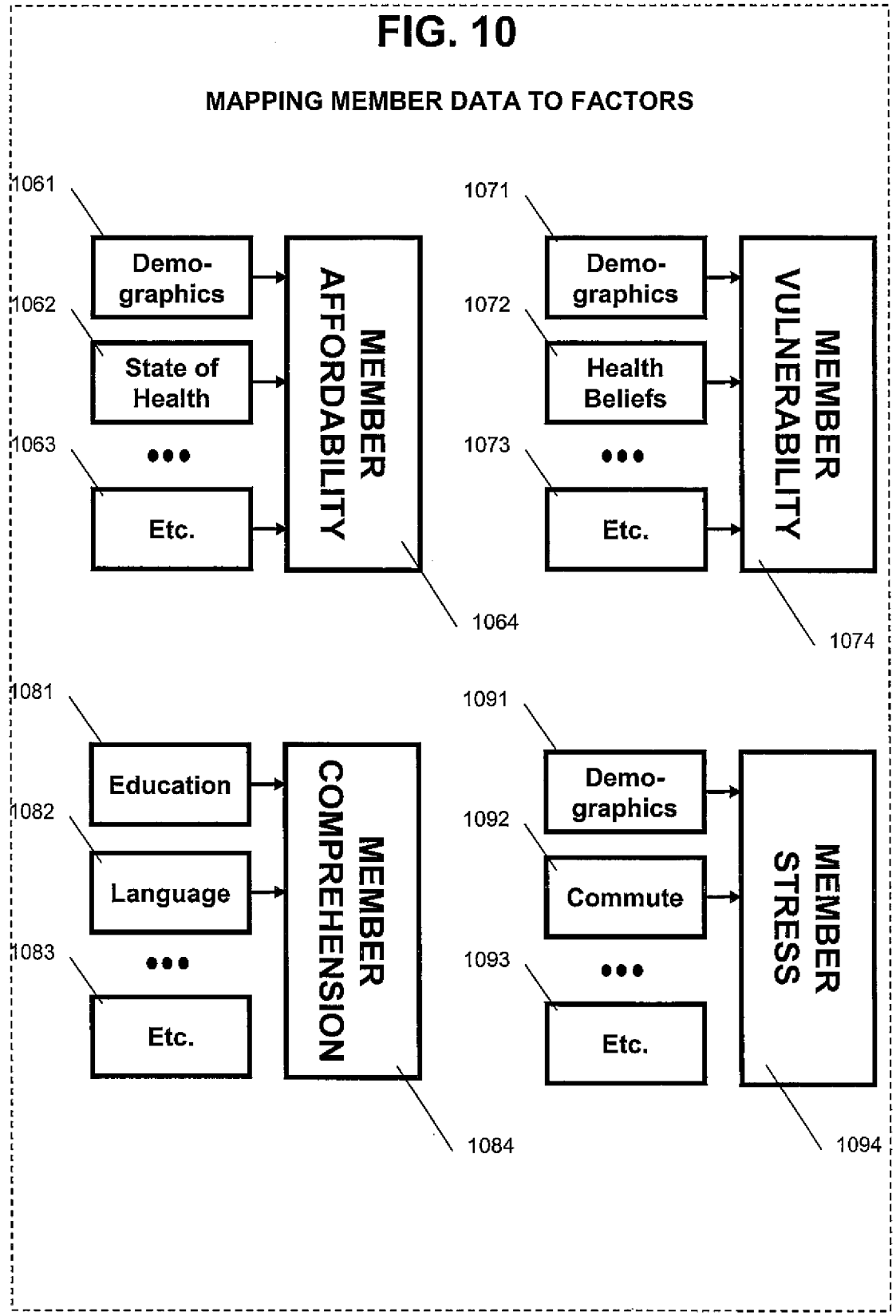
FIG. 10 shows the mapping of member data to member factors.

For this embodiment of the present invention, FIG. 10 shows the mapping of member data to the factors: Affordability 1064, Vulnerability 1074, Comprehension 1084, Stress 1094, screening, treatment, communities, and incentives (not shown). In each case, only a subset of the data mapped to the factors is shown for brevity, and this should not be construed as a limitation of any kind. For example, Affordability is shown as being mapped from demographics 1061 and state of health 1062, but there are other data that have not been specifically enumerated here, but are included in the box labeled 'Etc.' 1063. Similarly Vulnerability 1074 is mapped from demographics 1071, health beliefs 1072 and other data included in 'Etc.' 1073. Comprehension 1084 is mapped from education 1081, language 1082 and other data included in 'Etc.' 1083. Stress 1094 is mapped from demographics 1091, commute 1092 and other data included in 'Etc.' 1093.

Figure 11:
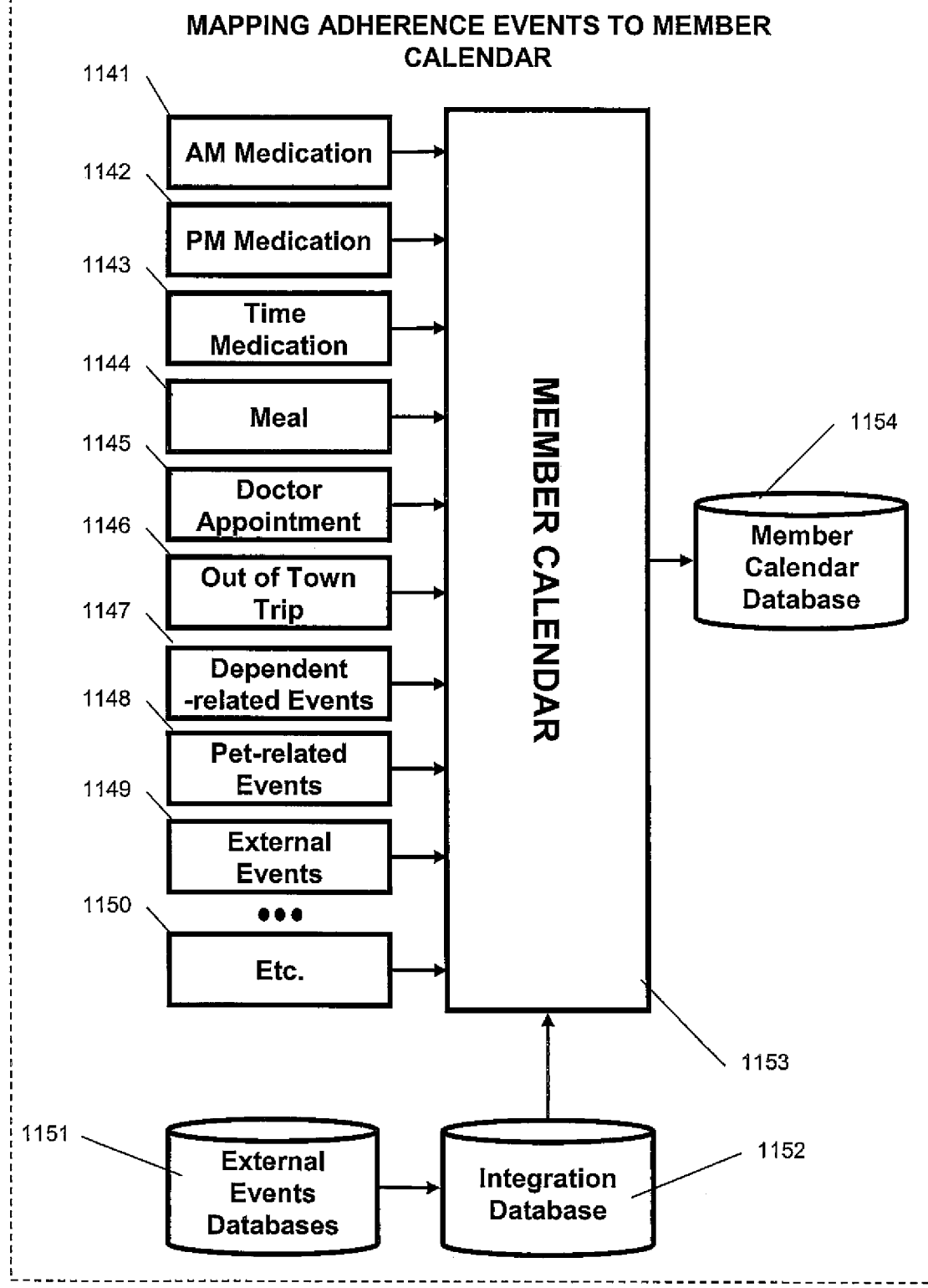
FIG. 11 shows the mapping of adherence events to the member calendar.

For this embodiment of the present invention, FIG. 11 shows various adherence events and their mapping to the member calendar 1153 and then stored in the member calendar database 1154. The events include: AM (morning) medication 1141, PM (evening) medication 1142, medication at a set time 1143, meal 1144, doctor appointment 1145, out of town trip 1146, events related to dependents 1147, events related to pets 1148, external events 1149 imported from external sources or created by the member, and others included in 'Etc.' 1150. The external events databases 1151 may reside on other internet sites; the data from these sites are imported into the integration database 1152 and used to populate the member calendar 1153. Events can be entered or modified by the member at various times by accessing the system as authorized. Once entered, the events are stored in the member calendar database 1154.

Figure 12:
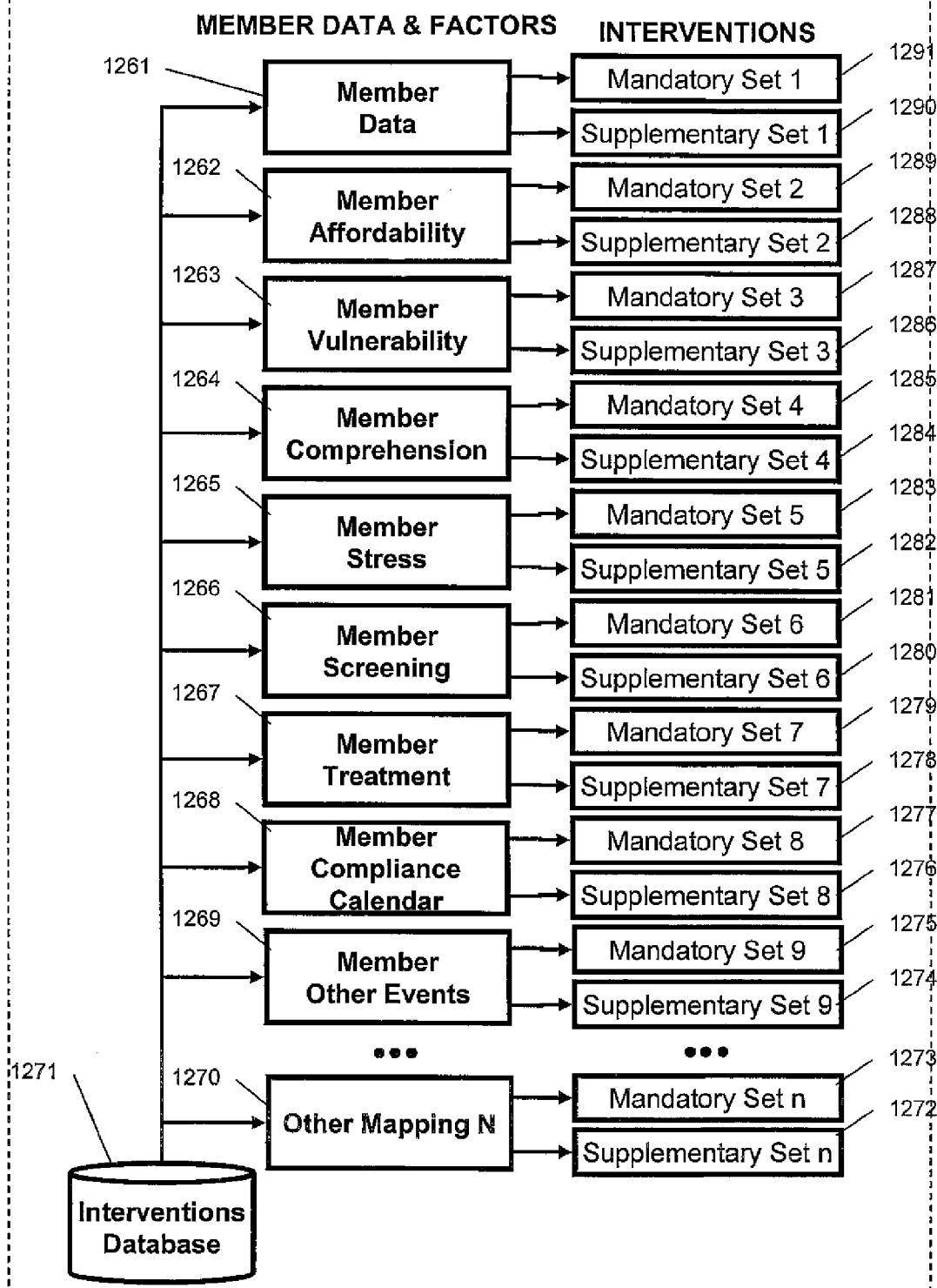
FIG. 12 shows the first step in the generation of the intervention plan

For this embodiment of the present invention, FIG. 12 shows the automatic generation of specific mandatory interventions 1273, 1275, 1277, 1279, 1281, 1283, 1285, 1287, 1289 and 1291 and supplementary interventions 1272, 1274, 1276, 1278, 1280, 1282, 1284, 1286, 1288 and 1290 based on member data and factors. Mandatory interventions cannot be deleted by the member, but they can be modified. Supplementary interventions can be deleted or modified by the member. Typically mandatory interventions require a response or measurement from the member while supplementary interventions serve to influence and enable behavior. Member data 1261, such as state of health, which identifies the member's diagnosed diseases, ensure that only interventions relevant to the member's selected diseases are generated. Member factors, calendar, events and other mappings 1262 to 1270 generate several mandatory and supplementary interventions. For example, the member affordability 1262 factor may generate mandatory interventions for free screening events or supplementary interventions for options to get medication copays waived or reduced, for a member with low affordability. The vulnerability 1263 factor may generate mandatory interventions for cholesterol and diabetes screening based on member demographics and risk factors.

Figure 13:
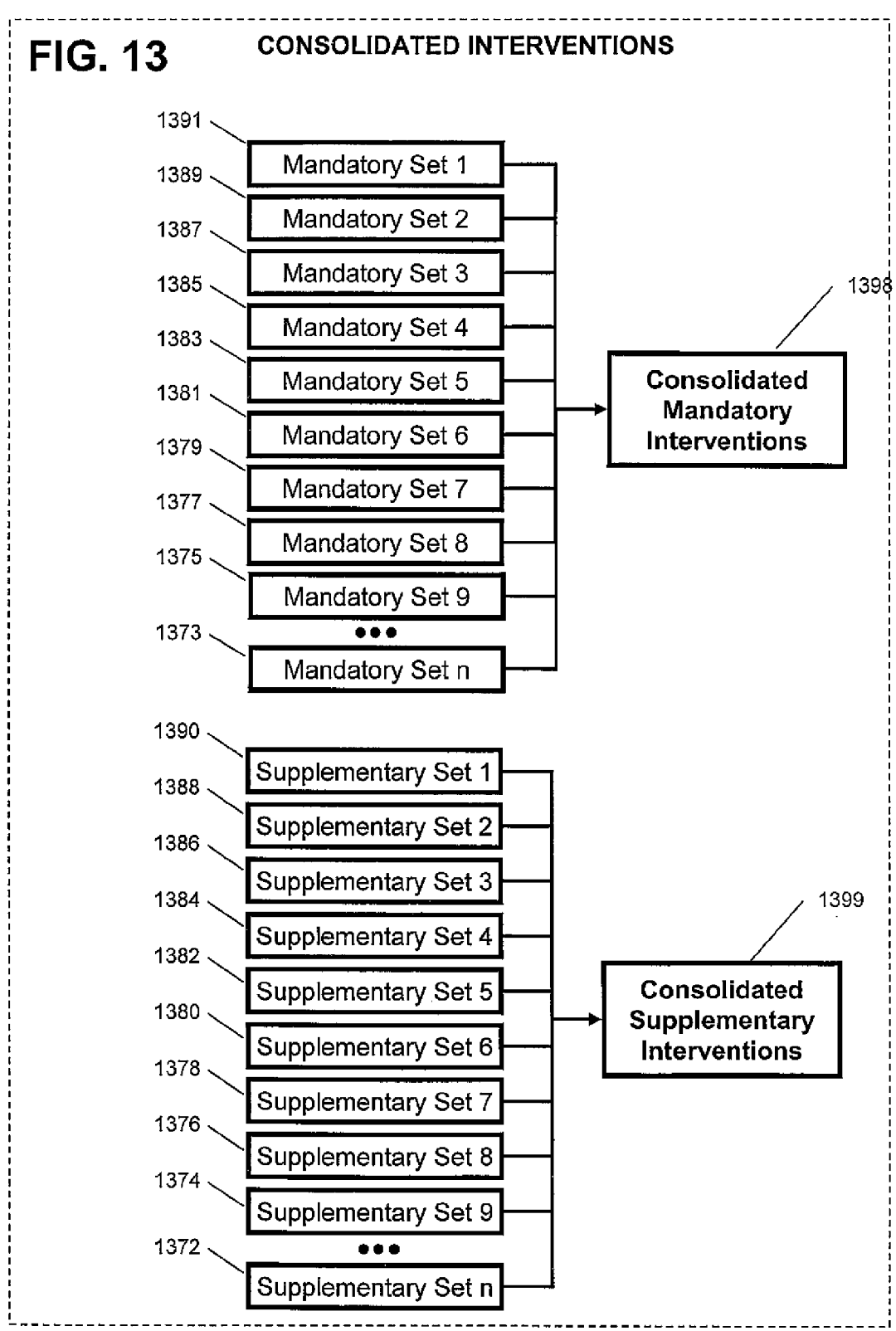
FIG. 13 shows one method by which interventions are consolidated.

For this embodiment of the present invention, FIG. 13 shows the consolidation of like interventions. The generated mandatory interventions 1373, 1375, 1377, 1379, 1381, 1383, 1385, 1387, 1389 and 1391 and supplementary interventions 1372, 1374, 1376, 1378, 1380, 1382, 1384, 1386, 1388 and 1390 are consolidated into like groups—mandatory 1398 and supplementary 1399.

Figure 14:
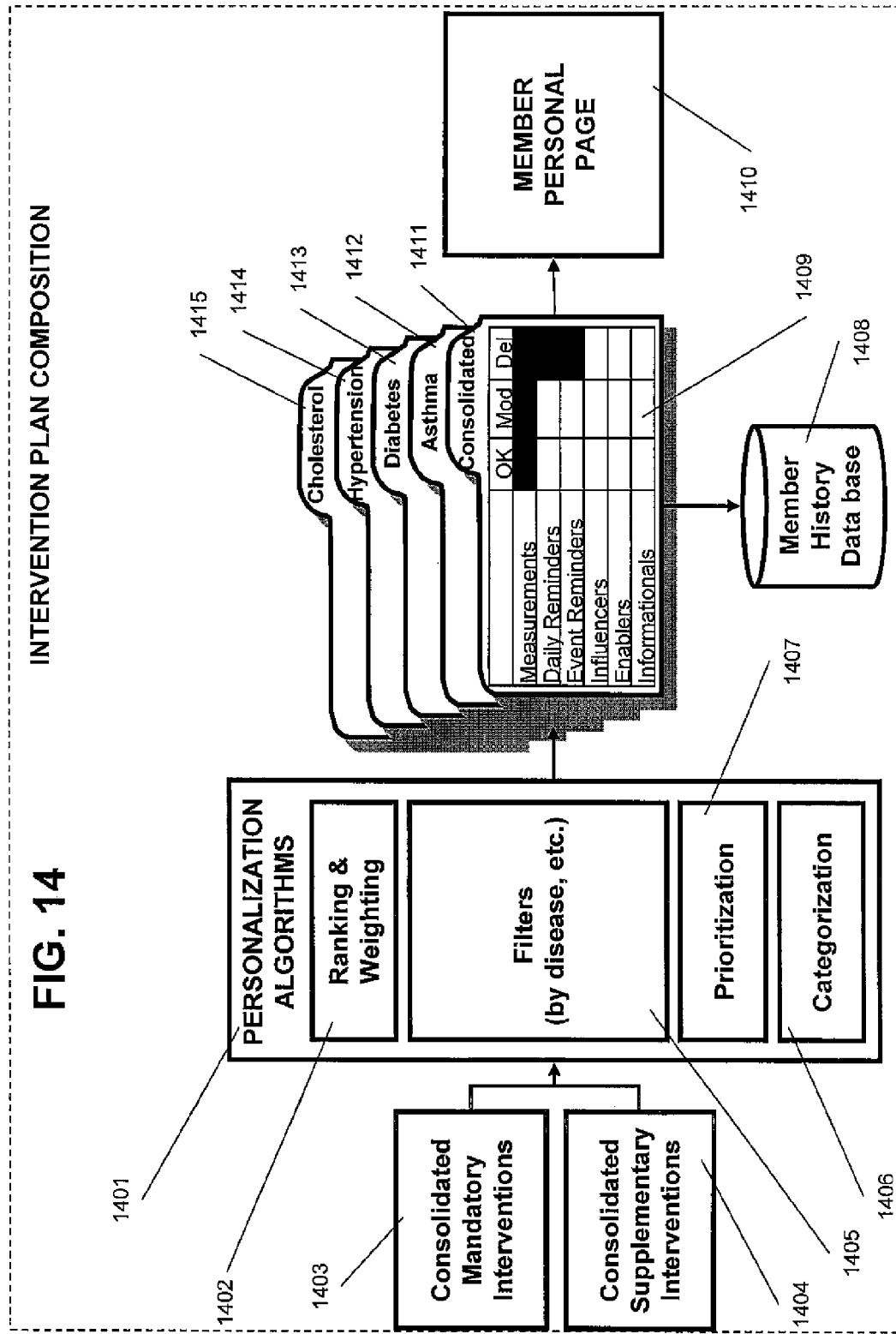
FIG. 14 shows the composition of the intervention plan.

For this embodiment of the present invention, FIG. 14 shows the method of composition of the intervention plan. Given the consolidated mandatory interventions 1403 and supplementary interventions 1404, personalization algorithms 1401 are used to automatically rank and weight 1402, filter 1405, prioritize 1407 and categorize 1406 the interventions. The result is a set of ranked interventions 1409 categorized by disease and presented for each disease that is applicable to the member, for example asthma 1412, diabetes 1413, hypertension 1414 and cholesterol 1415. These interventions comprise the member's intervention plan that becomes part of the member's personal page 1410.

Figure 14A:
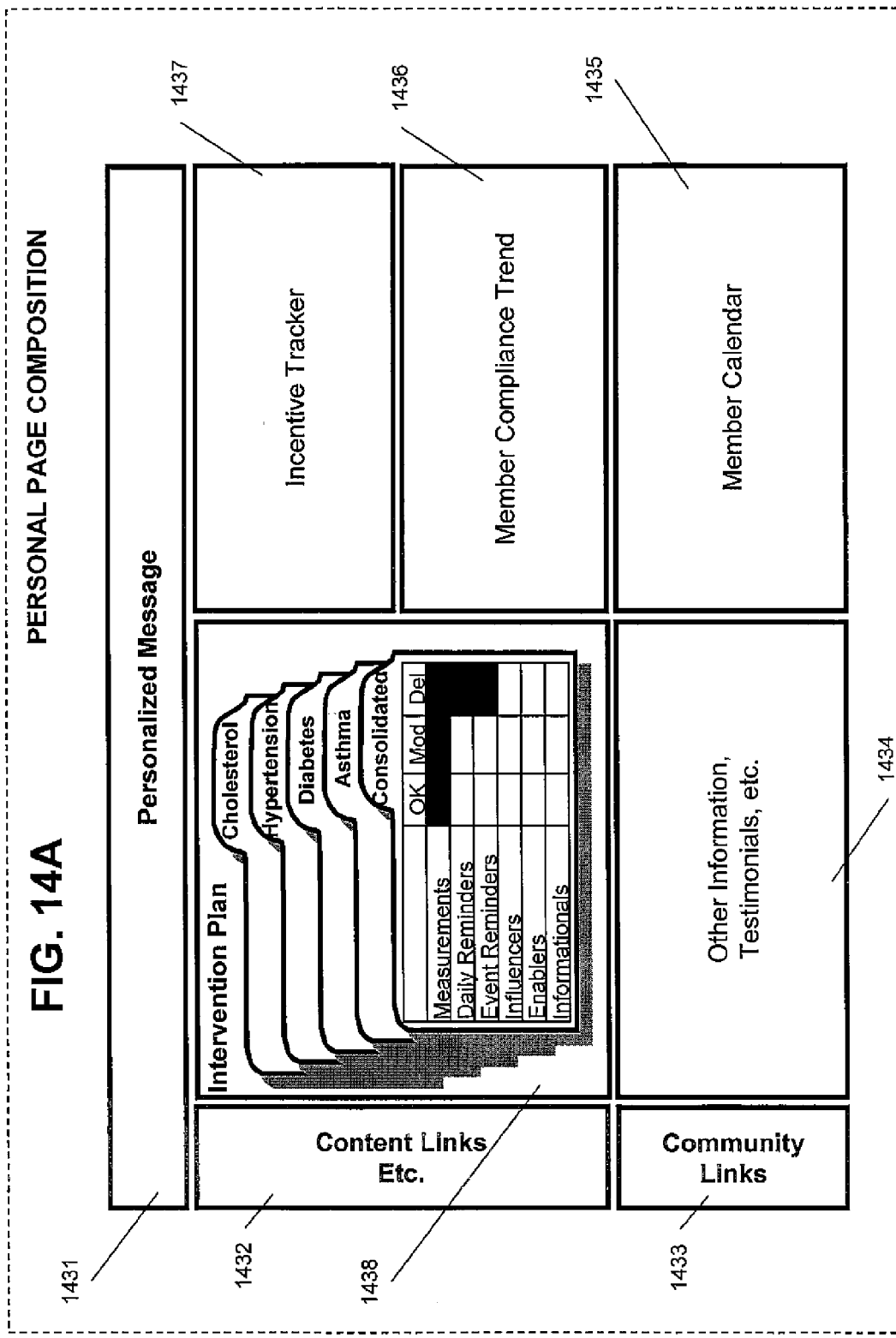
FIG. 14A shows the composition of a personalized web page.

For this embodiment of the present invention, FIG. 14A shows an example composition of the personal web page. The objective of the personal page is to present a member with the information, actions, enablers and links that are most likely to elicit a response from the member. Each member will have a unique page that is generated from the data provided by the member. In one embodiment of this invention, the personal will have a personalized message area 1431, relevant content links 1432, relevant community links 1433, other information such as testimonials 1434, a member calendar 1435 showing the member-specific events, reminders etc., a member adherence trend chart 1436, and a member incentive tracker chart 1437. It will also display the member intervention plan 1438.

In yet another embodiment, this invention is applied to the field of clinical trials, as shown in FIG. 27. A user, 2701, is usually not permitted to participate in multiple clinical trials at the same time. Clinical trials, 2702, have multiple phases and each phase is comprised of multiple stages in a sequence, very similar to conditions. After the recruitment phase, 2703, in which new patients are recruited for the trial, there is an inclusion and training phase, 2704, in which the recruited patients are screened for suitability and either included or excluded from the trial. Included patients are trained in this phase. Following this, the treatment & monitoring phase, 2705, begins in which the patient is treated and monitored per the clinical trial protocols. A member typically goes from start to finish but some may drop out of the trial at any stage. In clinical trials the phases and stages are pre-planned (e.g., recruitment steps, welcome visit, inclusion & training, study visits, treatment visits, study & concomitant medication adherence, etc.). Since the actions are pre-planned, the specific dates and times for these actions are known up front, and detailed action plans are created and consolidated in advance by the system. The action plans are then consolidated and presented with the user's condition and regimen management action plans as described above. In a similar manner, detailed information pertinent to the clinical trial is provided through the custom content links described above, such as online training. In addition, links are provided on the user interface to contact investigators, coordinators, social workers, and so on. Trial visits are pre-populated as calendar events and appropriate interventions such as reminders are provided automatically. Measurements are collected for medication adherence, trial protocol adherence, side effects, adverse effects, experiences, etc. In case of non-response, escalations or exceptions are automatically provided to caregivers, social workers, coordinators or investigators.

Adherence Management System

The techniques described herein seek to improve an individual's health and thereby reduce the individual's utilization of expensive health care services, by providing personalized health interventions that not only influence and enable an individual to maintain a high medical adherence, but also observe the member's behavior, measure the individual's adherence and use this information to adapt the interventions as the member's needs change.

Medical adherence consists of the following: (1) wellness adherence, or actively participating in programs designed to keep people healthy (diet, exercise, weight management, stress management, smoking cessation, etc.), (2) screening adherence: getting screened for certain diseases based on age, gender, race and other risk factors as recommended by medical guidelines, (3) medication adherence, or filling/refilling and consuming medications as prescribed, also known as 'patient adherence', and (4) treatment adherence, or going for specific condition-based treatments and follow-ups as prescribed. These and related terms are described below.

Adherence Events

Opportunities for adherence occur at certain events. An individual's goes through several age-based stages such as pediatric, adolescent, dependent adult, adult, and geriatric. During a lifetime, many medical encounters and events may take place. Events include going in for health screenings, doctor visits, filling prescriptions, taking medication, etc.

Events have a common structure and flow: (a) targeting a specific event, (b) making a commitment to the event, (c) preparatory activity, (d) participation in the event, and (e) following up after the event. In the case of a doctor appointment, the individual targets the physician, purpose and time of the appointment, then sets up the specific appointment (commits). If the appointment includes a lab test that requires the patient to be fasting, then starting at the recommended interval before the appointment event, the patient fasts (preparatory activity). Next comes the actual clinical encounter, or targeted event, i.e., the doctor appointment, at which the lab test may be reviewed, the patient examined and prescriptions for medications or referrals for further treatment may be given (participation). After the appointment is the follow up period, during which the patient and doctor periodically conduct additional appointment to ensure the prescribed medications or treatments are working and the patient is cured, or in control of the disease (following up).

Wellness & Prevention Adherence

Wellness & prevention programs require individuals to engage in specific behaviors that reduce health risks these activities include health risk assessments, immunizations, exercise, diet control, weight management, stress management, smoking cessation, etc. Many of the above are subsidized by employers, and some even offer incentives for enrollment or participation. In spite of the incentives, the actual rate of participation, in terms of how many individuals participate or how intensely they participate or how long they maintain the participation, is poor.

Screenings Adherence

A significant fraction of the population is unaware of the chronic illnesses lurking in their bodies; the CDC estimates that almost 32 percent of those who have hypertension do not know that they have it, a full XXX percent has not been screened for diabetes, XXX percent have not had a Pap smear, xxx percent has not had a mammogram, and so on. Clearly, these statistics indicate a significant level of non-adherence to screening programs. Planned adherence events such as screenings for specific diseases like hypertension or diabetes, provide opportunities for early detection and treatment of latent diseases. For example, a local pharmacy may sponsor a free hypertension screening event, or an employer may sponsor a work-place cholesterol and diabetes screening event. However, many individuals do not take advantage of these events for many reasons, both situational and behavioral.

Medication Adherence

A critical part of managing disease is medication—taking the right medicines at the right time at the right strength, taking all of the medications, and taking them for the duration prescribed by the doctor. An individual with multiple chronic illnesses may be prescribed several medications to be taken at different time during the day, for the foreseeable future. These times of day represent medication adherence events—times when an individual is required to take certain medications as prescribed. Whether the individual actually took these medications, and at what time of day, is of great interest from an adherence point of view. Using data about medication adherence events, physicians would be able to verify that their patients were indeed following their prescriptions properly, insurance companies would be able to verify whether patients were adhering to their regimens and offer incentives to improve adherence (if needed), pharmacies would be able to automatically process and deliver refills based on actual consumption, and pharmaceuticals companies would obtain more reliable clinical trial data.

Treatment and Follow-Up Adherence

Another critical part of managing disease is treatment—performing certain procedures on a regular basis to keep the disease from deteriorating and to catch emerging complications early, when they are cheaper and easier to treat. An individual with diabetes, for example, should ideally get an eye exam and a foot exam every year to evaluate whether the early signs of certain common complications are present so that appropriate medications can be prescribed or other treatments started. These recommended treatment and follow-up points are adherence events. The clinical guidelines for such treatments are well known but poorly followed, again for situational and behavioral reasons.

Doctor Appointment Adherence

Patients occasionally forget doctor appointments and this is an example of an adherence event that can easily be addressed using appointment reminders—phone calls from the provider to patients or caregivers the day before the appointment have been very successful in reducing the number of no-shows. In many cases, a doctor visit (office appointment) involves a lab evaluation and discussion, followed by prescriptions or treatment recommendations, or a referral. Many lab tests require the patient to prepare for the test before coming in. For example, cholesterol and glucose tests require that the patient be fasting for at least 10 hours. Other tests such as bladder ultrasound require the patient to drink a fair amount of water and not urinate before the test so the bladder will be in a distended state for the test. Failing to comply with these requirements will void the test results, so appointments are either rescheduled or the patient made to wait for the lab equipment to become available at a later time. A lot of inconvenience and false results can be avoided if patients comply with pre-visit requirements. A reminder to patients listing the specific requirements for the upcoming appointment would be an example of an intervention provided by this invention. For example, an automated call to the patient on the evening prior to an appointment to check cholesterol with a message to not eat anything after midnight would keep the patient from forgetting to fast. A similar call in the morning reminding the patient to not eat breakfast would be another example of an intervention in this regard.

System Inputs

The various inputs to the system are described below. The following are discussed for illustrative purposes and represent an embodiment of the present invention. Additional elements or changes to existing elements do not affect the nature of the system, and such modifications are expected. These inputs are entered by the member or by an authorized party on behalf of the member. Some of these inputs may also be imported from pre-existing databases and automatically entered into each member's profile. The member can subsequently verify and modify their data. After entry and member verification, the data are stored in secure member databases, and the members are considered to be registered users. After registration, there are six categories of inputs and a calendar: demographics, state of health, stage of change, health beliefs, self-efficacy and adherence factors. The calendar is a separate form for entry of events etc. It is anticipated that additional categories of inputs may be included at a future date within the scope of this invention.

Based on these inputs, each member's profile is characterized in terms of: (1) medical conditions, (2) stages of screening, diagnosis, treatment or followup for each condition, (3) stages of readiness for action or behavior change with respect to specific health actions, etc. These characterizations are determined in one or more of the following ways: (1) direct input by the user into questionnaires, (2) import of the data from other databases and subsequent verification by the member, (3) serving interventions based on initial profile assumptions, analyzing the member's responses and determining the appropriate stages in terms of conditions, readiness and action.

Registration

Registration is the first step for the member. A member accesses the registration page by either accessing the website directly using the url provided, or by clicking on a link provided in an introductory email or on the employee benefits management page. Once the member accesses the web site there is a 'new user' link on the page. Clicking on the link will take them to the registration page. There are two options for registration: (1) 'registration', in which the member has to enter multiple pages of profile data, and (2) 'express registration', in which the system either pre-populates or pre-fills the required profile data based on pre-determined rules, thus relieving the member of the burden of entering this data in one sitting. In this option, the system makes assumptions about a member's behavior and condition stages and presents a member view based on these assumptions—the view can be later modified by the member by modifying the pre-filled profile data entries. In the former option, the member manually enters all the profile data and thus the member profile is much closer to the actual status of the member. Examples of the profile data sections are described below—it should be noted that these are only examples, representative of a particular embodiment and that they may be different in other embodiments.

A Progress bar will show the progress of the input session, what percentage of the inputs has been filled, the position of the current page, and how much is left to complete the input session. The member can stop and save the session anytime; the session is also auto-saved every few minutes, hence the member can pause at anytime and resume after logging in at a later time.

Demographics

Demographics questionnaire captures the member's demographical data. Demographical data includes age, gender, race, family size, family arrangements, caregiver access, education, language, religion, job, industry, work class, income, work schedule, travel schedule, commute, hobbies, disabilities/pain, insurance coverage, access to computer, access to phone, etc.

The age of the member is a key factor that determines susceptibility to medical conditions. Age is recorded in one of two ways: (1) direct entry of the date of birth, from which the system calculates the current age, and (2) selecting an entry in the Age questionnaire that has selectable radio buttons for the following ranges: <5; 5-9; 10-14; 15-19; 20-24; 25-34; 35-44; 45-54; 55-59; 60-64; 65-74; 75-84 and 85+

Other demographics entries such as gender, ethnicity, etc., are entered through similar commonly used data entry techniques such as clickable drop down menus or check-box lists that have pre-programmed selections. There is also room for free-form entry by the member in case he does not fit one of the pre-programmed selections.

State of Health

The State of Health of a member is captured through questionnaires. Starting with the member's health interests in terms of disease information, treatment information and risk information, other questionnaires include the member's state of disease screening, participation in prevention and wellness programs, any disease symptoms, whether any diseases have been diagnosed, and if so, have treatments been prescribed, and whether the diagnosed diseases are under control. In addition, a health risk assessment may also be administered, or if one has already been submitted previously, the relevant data may be directly imported into the member's profile.

The disease questionnaire has the following items for which a check box is provided to indicate interest in the following diseases. These are shown for illustration only and the list may grow in other embodiments: Arthritis; Asthma; Allergy; Sinus disease; Cancer; CVD (cardio vascular disease); COPD (chronic obstructive pulmonary disease); Depression; Diabetes; Elevated cholesterol; Migraine; GERD (gastric esophageal reflux disease); Hypertension (high blood pressure); Hormonal disorders; Kidney disease; Ulcers; Colorectal cancer; Breast cancer; Cervical cancer; Prostrate cancer and other conditions specified by the member.

In the preferred embodiment, the screening questionnaire has a set of mutually exclusive items that can be selected by the User to indicate the current status with respect to each condition. The items are as follows:
I plan to go for a screening in the next [ ] six months [ ] month
I have set up a screening appointment [ ]
My screening results are normal [ ]
Each of these items is mapped to a specific stage in the screening phase of the respective condition. When a User selects one of these items, the system immediately identifies the User as being in the particular mapped stage corresponding to the selected item. Similarly, there are questionnaire items for the Diagnosis and Treatment phases, which follow the same method. The questionnaires for all three phases are presented to the User at the same time, allowing the User to select which phase and stage are current for each condition selected fro the User. For illustrative purposes, the questionnaires for the Diagnosis and Treatment phases are as follows:
Diagnosis:
I plan to go for diagnosis tests in the next [ ] six months [ ] month
I have set up an appointment for diagnostic evaluation [ ]
I have been diagnosed with (condition) [ ]
Treatment:
I plan to go for treatment in the next [ ] six months [ ] month
I have set up an appointment for treatment [ ]
I am being treated for (condition) [ ]

In another embodiment, the screening questionnaire has a series of items relating to specific diseases that should be screened for per medical guidelines, and have multiple checkboxes or other means to indicate the member's screening status with respect to each disease. For example, the questionnaire may have the following items:
My blood pressure was measured by a health professional:
[ ] never measured [ ] 1 year ago [ ] 2 yrs ago [ ] 3 yrs ago [ ] 4 yrs ago [ ] over 5 yrs ago
I was tested for colorectal cancer (sigmoidoscopy or colonoscopy) by a health professional:
[ ] never measured [ ] 1 year ago [ ] 2 yrs ago [ ] 3 yrs ago [ ] 4 yrs ago [ ] over 5 yrs ago
I was tested for breast cancer (Mammogram) by a health professional:
[ ] never measured [ ] 1 year ago [ ] 2 yrs ago [ ] 3 yrs ago [ ] 4 yrs ago [ ] over 5 yrs ago
I was tested for cervical cancer (PAP smear) by a health professional:
[ ] never measured [ ] 1 year ago [ ] 2 yrs ago [ ] 3 yrs ago [ ] 4 yrs ago [ ] over 5 yrs ago
I was tested for prostate cancer (PSA) by a health professional:
[ ] never measured [ ] 1 year ago [ ] 2 yrs ago [ ] 3 yrs ago [ ] 4 yrs ago [ ] over 5 yrs ago
For Wellness & Prevention state of health, an example is as follows:
Weight-loss program—I am: [ ] not enrolled [ ] enrolled [ ] active [ ] achieving results
Exercise program—I am: [ ] not enrolled [ ] enrolled [ ] active [ ] achieving results
Smoking Cessation program—I am: [ ] non-smoker [ ] not enrolled [ ] enrolled [ ] active [ ] achieving results
Vitamins—I am: [ ] not taking [ ] taking
Alcohol—I consume: [ ] none or occasionally [ ] 1-5 drinks a week [ ] 6-14 drinks a week [ ]

In the 'Disease Symptom' state of health questionnaire, only those diseases that the member has indicated to be of interest in the 'Disease' questionnaire above, are shown to the member, although the complete list consists of all the diseases listed. An example of the questionnaire for each shown disease is given below:
I have (for disease):
[ ] None or Hidden Symptoms [ ] Overt or Visible Symptoms [ ] Mild Symptoms [ ] Moderate Symptoms [ ] Severe Symptoms [ ] Impairments [ ] Complications In the 'Diagnosis' questionnaire, again, only the diseases selected by the member are shown, and for each shown disease the following questionnaire is displayed:
I have (for disease):
[ ] Early signs [ ] Diagnosed less than 1 year ago [ ] Diagnosed more than 1 year ago In the 'Treatment' questionnaire, only for the diseases that have been diagnosed, the following questionnaire is displayed:
For (disease) I am:
[ ] not taking treatment [ ] medications prescribed [ ] medications being taken as prescribed most of the time [ ] medications being taken but not exactly as prescribed [ ] treatments prescribed [ ] treatments being taken In the 'Control' questionnaire, again, only for the diseases that have been diagnosed, the following questionnaire is displayed:
For (disease):
[ ] not under control [ ] under control less than 1 year [ ] under control less than 5 years [ ] under control more than 5 years Stage of Change Long-term studies of behavioral change, coming from the field of addiction treatment, show that lasting behavioral change comes only when the patient is motivated to change. Externally imposed cues to change behavior only work as long as they exist; as soon as the cues are removed, the behavior quickly reverts. In this regard, it has been found that people who have successfully changed their behavior in the face of barriers and challenges go through the same five stages of change: (1) pre-contemplation, in which even the thought about changing behavior does not occur, (2) contemplation, in which the person starts to think about changing their behavior, (3) decision, in which the person makes a decision to change their behavior, (4) action, in which the person takes specific actions towards changed behavior, and (5) maintenance, in which the actions are sustained over time, in the face of life-events that would normally have driven the person to the previous behavior. This is not a perfect straight-line model, so in the maintenance stage, 'relapses' do occur, and the person may go through all or some of the other stages repeatedly, but over time, will adhere more to the new behavior than to the old. In the present invention, these concepts are applied to the field of medical adherence. Taking a young individual who is not even thinking about disease risks to the point of seeking the recommended screenings, for example diabetes screenings, requires consistent, highly targeted (i.e., personalized) interventions. Such an individual is in the 'pre-contemplation' stage and first needs to be influenced to start thinking about disease risks, i.e., to move to the 'contemplation' stage. Thus the present invention may provide interventions highlighting the potential consequences of neglecting certain diseases—an example would be a testimonial from person similar in age, gender, race socioeconomic status etc. (i.e., as close to the individual's profile as possible), showing the effect of neglecting diabetes, such as blindness. Multiple interventions, repeated periodically, with different content, but conveying the same message ('you need to go in for a diabetes screening') are necessary. The frequency of the interventions is also important—daily interventions would probably cause the individual to consider them a nuisance and 'tune them out', whereas monthly interventions would probably not register in the individual's memory and would therefore not be effective either. The present invention derives the initial frequency from the individual's profile and automatically adjusts the frequency based on the response or non-response from the individual, thus increasing the chances of getting the message through, and moving the individual to the 'contemplation' stage. Once in the contemplation stage, the individual needs different types of interventions—'enabling' rather than 'influencing', to help decision-making and move the individual to the next stage, namely, 'decision'. In the action and maintenance stages, the individual requires yet other types of interventions, enabling (such as reminders) and measuring (to ascertain the level of adherence). As the individual moves from stage to stage, forwards or backwards, the present invention adapts and provides the required types of interventions to keep the individual engaged in their health and moving towards self-efficacy, or the 'maintenance' stage.

The inputs for the stage of change are in the form of a questionnaire with either 'yes/no' or a scaled response option. The exact form, number of items and scoring method may vary as more is learned, but in one embodiment, the stage of change questionnaire may be as follows, with a five-point scaled response option indicating strong agreement, agreement, neutral, disagreement or strong disagreement to the items:
(1) I am OK with how I take my medications
(2) I am trying to take my medications more regularly than I used to
(3) I sometimes miss taking my medications
(4) I should cut down on the times I miss taking my medications
(5) It's a waste of time thinking about missing my medications
(6) I have just recently changed my habits of taking medications
(7) Anyone can talk about taking medications regularly, but I am actually doing something about it
(8) I am at the stage where I should think about taking my medications regularly
(9) I have a problem with taking my medications
(10) It's alright for me to keep taking my medications as I do now
(11) I am actually changing my medication taking habits right now
(12) My life would still be the same, even if I missed fewer of my medications
The scoring method is to add up the points corresponding to the items that represent the different stages of change and place the individual in the stage with the highest score.

Health Beliefs

Health beliefs determine the specific actions of the individual. As described above, in order to get an individual to even think (or contemplate) health risks, initial interventions are oriented towards raising awareness of the individual's 'perceived susceptibility' to certain diseases. Sometimes this is not enough and the interventions have to be raised to another level in order to raise the individual's 'perceived severity' if the diseases are allowed to take root, such as horror stories. These interventions, repeated at the right frequency, will eventually cause the individual to think about doing something, but typically all sorts of 'perceived barriers', real and imagined, come up. At this point, the individual needs 'enabling' interventions that highlight ways in which the barriers can be overcome, testimonials about how others have overcome similar barriers, links to online communities where questions can be asked with anonymity, link to an online anonymous mentor who can guide the individual and so on. Interventions highlighting the benefits of taking action, such as testimonials can also 'influence' the individual into taking action. The individual may also need, based on perceived self-efficacy, 'cues to action' that exploit existing habits of the individual to improve adherence, for example, linking the already established habit of brushing teeth at night to taking the evening dose. In addition, the individual's trust plays a key part in adherence. If there is adequate trust in the healthcare system, the doctor or the pharmacist—that they are indeed looking out for the individual, the chances of adherence are higher. If the individual's trust in medications or treatments is poor, the chances of high adherence are also poor. Therefore, one goal of the present invention is to provide interventions geared towards increasing the overall health beliefs of the individual.

The inputs are in the form of questionnaires with either a 'Yes/No' or a scaled response option and cover the following dimensions: trust in the healthcare system, trust in the physician, trust in the pharmacist, trust in medications and treatments, perceived susceptibility, perceived severity, perceived barriers, perceived benefits and cues to action. The exact form, number of items and scoring method may vary as more is learned, but in one embodiment, the health-belief questionnaires may be as follows, with five-point scaled response options indicating strong agreement, agreement, neutral, disagreement or strong disagreement to the items presented. The <disease> indicates a variable such that the specific name of a disease may be specified for a particular individual.
A. Perceived Susceptibility:
(1) People like me do not get <disease>.
(2) I would rate my chances of getting <disease> as poor.
(3) Whenever I hear of someone getting <disease>, it makes me realize that I could also get it.
(4) I think about the possibility of getting <disease> some day
(5) I am at risk for getting <disease>
B. Perceived Severity:
(1) <disease> can be serious if I get it
(2) <disease> will affect my job
(3) <disease> will affect my personal life
(4) <disease> will limit my activities
(5) <disease> could make me disabled
C. Barriers:
(1) I would have to change many habits to follow my diet, exercise or medication regimen.
(2) It will be difficult to follow the diet, treatments or medication regimens prescribed for me.
(3) I cannot understand or remember what I've been told about my diet, treatments or medications.
(4) Exercising, watching my diet, and/or taking my medications interferes with my normal daily activities.
(5) Knowing about all my health conditions makes life miserable
D. Benefits:
(1) Improving my diet and exercise habits will make me feel better.
(2) Going in for health screenings every year will catch any diseases early
(3) Taking my medications regularly will keep my <disease> from getting worse.
(4) Good diet, exercise and medication habits will maintain my health
E. Cues to Action:
(1) I follow the same routine every day when I get up
(2) I make notes to myself to take my medications during the day
(3) I have things to help me remember to take my medications at the appropriate time
(4) Someone usually has to remind me to take my medications Self Efficacy Self-efficacy is a measure of the confidence and independence of the individual. An individual with high self-efficacy can be expected to find out what to do and actually do them, whereas someone with a low self-efficacy needs help. An individual with high self-efficacy is likely to be high in adherence as well, and vice versa. Self-efficacy applies to multiple areas of health, and an individual's self-efficacy can be different in each area. For example, someone who is completely self-efficacious in taking medications can be totally not so in the area of smoking-cessation.

The inputs to self-efficacy are in the form of short questionnaires indicating levels of self efficacy in each of the areas of: screening, diet, exercise, stress, smoking cessation, medication and treatment. In one embodiment, the screening self-efficacy questionnaire may be as follows:

[ ] I can figure out what to do and do it myself
[ ] I need some help to figure out what to do
[ ] I need someone to figure it out for me
[ ] I need someone to make sure I<perform the action> (such as go for screenings, follow my diet, exercise regularly, manage stress levels, stop smoking, take medication and go for treatments.

Medication Adherence Factors

Medication adherence, as mentioned previously, is taking all the prescribed medications as directed, at the right time and at the right dosage strength. This turns out to be quite difficult for many individuals. Studies show that overall adherence is only around 50 percent. In this embodiment, we characterize the individual in terms of several factors that influence adherence, namely regimen complexity, unpredictability of life/work, forgetfulness, cost, drug efficacy, access to medications, knowledge about medications, knowledge about clinical results, side effects, secrecy, denial, health beliefs, self-efficacy, confidence, and other factors.

A complex regimen with multiple pills and capsules to be taken at different times on a daily basis (such as regimens for those with HIV or multiple chronic illnesses) can be challenging and individuals frequently miss a dose or two, or forget that they have already taken them and take them again (resulting in potentially dangerous overdosing), or simply give up and stop taking them.

Unpredictability of life/work frequently prevents individuals from taking their medications at the proper times of day. If they are in meetings or otherwise occupied, they might not be able to take the dose at the right time, but may have to wait for an opportunity to take them.

Forgetfulness is one of the main reasons for non-adherence. In the course of their busy lives, people frequently forget to take their medicines or to pack them before going on a trip.

Cost is another dominant reason for non-adherence. People are usually required to pay some amount of money in the form of co-pays or co-insurance, depending on their health plan. If the co-pays are high, people sometimes skip the drug. This behavior is also a function of socio-economic and insurance coverage status, with poorer or uninsured people more likely to skip the drug.

Drug efficacy has to do with whether the individual continues to take the prescribed drugs even if symptoms are not present in the belief that the drugs are working to control disease. It is quite common to see people stopping their medications as soon as they feel better, especially in the case of antibiotics. Some diseases do not present overt symptoms such as hypertension, yet wreak havoc within the body, and the effects only become apparent when a catastrophic cardiac event occurs.

Knowledge about medications—when people understand how the medications work to control disease, they are more likely to take their medications as directed.

Knowledge about clinical results—when people know what the clinical results (lab tests) represent, whether they have the disease under control or not, they are more likely to take the medications as directed. When they know the results are abnormal, they will tend to take their medications more regularly.

Side effects are a big reason for non-adherence. Even if an individual realizes that a medication is necessary to control a disease, side effects can be bad enough to inhibit regular consumption. When the cure is worse than the disease, poor adherence is often the result.

Secrecy is another reason why people miss taking their medications. Not wanting anyone to know that they are taking medications, is a big concern especially in the work environment where it may be seen as a weakness. Others simply want to maintain privacy.

Denial of disease is quite common and people will resist taking medications since taking them would be an admission that they have a disease.

Confidence is a leading indicator of adherence behavior. It is a measure of the level of confidence of the individual in taking the medications as prescribed, in the face of common barriers. In providing the inputs for this dimension, the individual actually programs himself or herself for high adherence.

Calendar

The adherence calendar is a key element of the member's interaction with the system, both in terms of inputs and outputs. In terms of inputs, the calendar is used to directly enter events related to the member, dependents or pets (appointments, etc.). Certain scheduled adherence events, appointments, reminders, screening events, and so on can be pre-populated on the member's calendar by importing relevant event data from external calendars or databases.

Pre-Population of Fields

If member data exists in the employer, health plan or other database, they can be imported and the input data entry fields can be pre-populated. Members only need to verify or correct pre-populated data and add missing data, thus simplifying the data input.

Personalization

A key aspect of this invention is the deep level of personalization that is provided by the system. In the preferred embodiment, based on member inputs of: age, gender and ethnicity, provided during registration, the system first looks up a medical guidelines and recommendations database and identifies the conditions for which the particular member needs to be screened.

Next the user selects a set of questionnaire items indicating the current state of the user with respect to each of the identified conditions. These selections, as described previously, specify the phases and stages from which the interventions for each condition can begin. This personalizes the interventions to the User by matching the interventions to the specific condition—phase—stage for the User. Further personalization is based on the user's 'readiness for change' with respect to certain stages, such as going for a diagnosis visit to the doctor. A user may currently reject the need to go for a diagnosis, even with a positive screening, because of denial or lack of urgency; such a user is in the 'pre-contemplation' stage of change and needs to be persuaded to go for a diagnosis. This may take several interventions, each with appropriate content designed to influence the user to 'contemplate' a diagnosis visit. In this manner, the content of the interventions is personalized based on the user's current stage of change, to incrementally move the user towards the Decision, Action and Maintenance stages of change. This has been described in more detail previously.

In yet another embodiment, based on the member inputs, a multi-factor profile is developed and this profile drives the personalization of specific interventions. The inputs outlined above are loaded into the member database and a profile is developed in terms of member-specific factors. The following factors are used: vulnerability, affordability, stress, comprehension, screening and treatment. In other embodiments, additional factors may be included or existing factors may be dropped. These factors are discussed for illustrative purposes only.

Vulnerability is an indicator of the diseases to which the individual may be susceptible, based on age, gender, race, job type and other factors. An individual's genetic endowment predisposes him or her to certain diseases, but environmental risk factors and lifestyle also play a key part. For example, if the member is of a certain age, gender and race combination that has a high prevalence of a disease, say, diabetes, then the member is deemed to be at high risk for diabetes and is therefore a candidate for screening. Screening for diabetes typically includes a fasting glucose and/or an oral glucose tolerance test—there are medical guidelines from organizations such as the AHRQ (Agency for Healthcare Research and Quality) that recommend screening tests for various diseases. Screening tests are sometimes covered by some health plans, making it easier for the member to get screened. The member's job title indicates whether it is an active or sedentary job, and if it is the latter, then the risks for diabetes are higher. The member's screening state of health indicates whether the member has already been screened for diabetes, and how many years ago. If the member has not been screened at all or for more than two years, then he/she needs to be influenced to do so. The member stage of change data may indicate that the member is in the pre-contemplation stage, so the influencers need to be oriented towards increasing awareness of the disease prevalence, increasing the perceived susceptibility to diabetes by virtue of age, gender and race, and increasing the perceived severity of the disease.

The vulnerability mapping algorithm uses 'if-then-else' type of logic to take these factors into account and identifies a set of candidate interventions of two types: mandatory and supplementary, from the interventions database. An example of a mandatory intervention in this case might be emails regarding a specific diabetes screening event at the workplace a week before and a day before the event respectively, an SMS reminder just prior to the event urging the member to go for the screening, and an SMS measurement a day after the screening to verify that the member went for the screening. Examples of supplementary interventions might be links to content on the member's PurpleTeal personal page about the dangers of neglecting diabetes, statistics about how many people neglect diabetes and horror stories about people who have neglected their diabetes and gotten into severe complications. These interventions are generated by the mapping algorithm and then consolidated into the mandatory and supplementary categories.

Affordability is an indicator of whether the member can pay for the screening, drug or procedure. In one embodiment, affordability is based on income, family size and insurance coverage (from the demographics inputs) and indicates whether the member is likely to go for the recommended screenings or take the prescribed drugs and treatments.

In a manner similar to the vulnerability mapping above, the affordability mapping algorithm uses 'if-then-else' type of logic to take these factors into account and identifies a set of candidate interventions of two types: mandatory and supplementary from the interventions database. In the case where the member is not filling drug prescriptions because of cost, an example of a mandatory intervention might be emails suggesting programs that offer free drugs, an SMS message to remind the member to contact the free drug program and another SMS message to verify that the member has contacted the program. Some employers have waived co-pays for certain chronic disease medications, and in this case, the member should be made aware of this via a mandatory email. Supplementary interventions may include emails to ask the doctor for samples, ask for a higher dosage prescription and split the tablets (if feasible), manufacturer discount program links or links to coupons and so on. As with the vulnerability mapping, these interventions are also generated by the mapping algorithm and then consolidated into the mandatory and supplementary categories.

Stress, in one embodiment, is determined by the member's job, work schedule, daily commute, family size, family arrangements and state of health. Other factors may also be included on different embodiments. In a manner similar to that described above for vulnerability and affordability, the stress mapping algorithm generates a set of mandatory and a set of supplementary interventions, that are then consolidated.

Comprehension, Screening and Treatment are other mappings in this embodiment that generate respective sets of mandatory and supplementary interventions that are subsequently consolidated. These mappings are cited for illustrative purposes. In other embodiments, additional and different factors may be employed in different combinations to generate the same two sets of interventions: mandatory and supplementary, that are then consolidated.

Intervention Plan Composition

In the preferred embodiment, the interventions are based on the member's condition, stage and stage characterization, and are then consolidated in terms of a calendar time window (daily, weekly, monthly or other basis), as described in FIG. 5G above.

In another embodiment, once all the mappings have been executed and the mandatory and supplementary interventions have been generated and consolidated, the member-specific intervention plan is composed (see FIG. 13). The following methods may be used to further personalize the interventions. These methods are discussed for illustrative purposes and other methods may be used in other embodiments.

Weighting & ranking: member factors such as vulnerability, affordability, etc., are not all of the same importance, and may be different for different members. For example, a member with a serious illness may be more concerned about vulnerability than affordability, whereas a member with low income may be concerned more about affordability, even at the cost of neglecting his or her health. These factors need to be weighted differently depending on the member profile. The weighting and ranking algorithm first calculates member-specific weights for the different factors and then applies the weights to the interventions driven by the respective factors. If an intervention is repeated, each instance is weighted by the respective weight, and the total weighted counts are added to yield a weighted score for each intervention. The interventions are then ranked in the order of the weighted scores.

Disease criticality ranking: in this method, certain diseases are deemed more urgent and severe than others, for instance, asthma, some types of diabetes or heart-related diseases are potentially life-threatening and the effects can be severe, so they are high on the criticality list. Diseases that involve pain or similar debilitating symptoms but are not life-threatening, are deemed to be lower in criticality, and diseases that do not have overt symptoms or have slow-changing effects, such as cholesterol are lower on the criticality list. In this method, the interventions are arranged in the order of disease-criticality.

Filtering: as another step in the personalization, in this method, the interventions are filtered using the member profile and factors. If any interventions generated by the various algorithms are mismatched to the member profile, the chances of being ignored are higher. This method serves as a final filter to eliminate interventions that do not match the member's age, gender, race, socio-economic status, education level, whether the member prefers concise or detailed information, etc. The objective is to ensure that only the most appropriate interventions and content are sent.

Categorization into disease-specific folders: as the final step in the personalization, the interventions are categorized into disease-specific categories and grouped together into separate 'folders' for display purposes. A consolidated view is also generated for display (see FIG. 13).

Initial frequency and timing: Each intervention has a frequency and timing when it is sent to the member. Depending on the intervention, the frequency is set at daily, twice weekly, weekly, monthly, quarterly or annually. For example, a medication reminder may be set at a daily frequency and the timing may be set at 8:00 AM and/or 8:00 PM. An adherence measurement reminder may be once every three days or once a week, or may be sent on random days, at random (but reasonable) timings. Timing is also event driven, for example sending a medication packing reminder to a member on the evening before an out-of-town trip is based on the timing of the trip.

Personal Page, member modifications and acceptance: the member is shown a personal page (see FIG. 14) with different elements, including the consolidated and categorized folder views of the interventions planned for the member. From this page, the member can accept or modify the interventions, their timing and other parameters. Mandatory interventions cannot be deleted but their timing and frequency can be modified. Supplementary interventions can also be deleted by the member. Once the member has modified the personal intervention plan, he or she has to accept the plan in order to activate it, after which the interventions are automatically sent. The member can login to their personal page at any time and modify the interventions. Until acceptance, none of the modifications are valid.

Intervention Database

The intervention database is a repository of all the interventions that can be sent by the present system. Links to third-party interventions are also stored here, to be drawn upon when appropriate, and the respective e-commerce interactions are enabled. The present system can thus be a single point of reference for all interventions to be sent to a particular member, whether the interventions are within the present system or within external parties. The interventions are structured into the intervention model below before storage in the database. This structure facilitates the identification of appropriate interventions from the database for a particular member.

Intervention Model

With respect to FIG. 5E, the attributes of an intervention and the response options and rules for handling the responses constitute the intervention model. The attributes shown in this embodiment are for illustrative purposes and may be expanded in other embodiments.

Types of interventions: interventions may be of different types depending on the purpose. The types in one embodiment are: informational, influencing, enabling, measuring, and event-driven. Informational interventions convey information one-way to the member, such as event dates or appointments. Influencing interventions seek to increase awareness, increase perception of susceptibility, and so on, with the expectation of some thought or action from the member. It may be informational but the intent is to elicit some response, either overt or hidden. As mentioned previously, compelling images of people who have suffered as a result of neglecting their diseases may influence the member to start thinking about their own situation. Enabling interventions are designed to help the member carry out some task. For example, a member in the decision stage of change with respect to screenings may find an action item checklist useful in scheduling and attending screenings, i.e. moving to the action stage of change. Measuring interventions are designed to ascertain various adherence behaviors. For example, a member who has moved to the action stage of change with respect to screenings and has set up the screening appointments may be sent a measuring intervention after the screening to ascertain whether or not the member actually went for the screening. Interventions are also event-driven. An example might be a checklist of items to discuss with the doctor that is sent before an appointment.

Intervention Channel: interventions are transmitted through multiple channels such as: SMS (cell phone), email, landline, alternate (family member, caregiver, and neighbor) phone, pager, PDA, internet, online community, online mentor, doctor, provider, nurse, pharmacist, volunteer and so on, as shown in FIG. 15. The purpose of the channel is to electronically or physically get the intervention to the member. Some channels are more effective than others, depending on the member's profile, and the present system automatically selects the most appropriate channels for the member. It is well known that multiple channels do a better job of conveying the message, so the same intervention may be sent over more than one channel.

Intervention frequency: each intervention has a frequency at which it is sent to the member. Depending on the intervention, the frequency is set at daily, twice weekly, weekly, monthly, quarterly or annually. For example, a medication reminder may be set at a daily frequency. An adherence measurement reminder may be once a week, or may be sent on random days. An annual checkup reminder may be sent once a year. In one embodiment, the intervention frequency is fixed, whereas in a different embodiment, means are provided for the member to modify the frequency.

Intervention timing: interventions also need to be timed for maximum response from the member. Morning and evening medication reminders may be sent to one member at 8:00 AM and 8:00 PM, and at different times for a different member. The timing can also be member-defined. In addition, if a member is traveling in different time zones, the reminder timings have to be automatically adjusted for the respective time zones. Timing is also event driven, for example sending a medication packing reminder to a member on the evening before an out-of-town trip is based on the timing of the trip. Other events include: before food, after food, before screening, after screening, before doctor visit, and so on.

Response options and handling rules: certain interventions require the user to respond while others are for informational purposes only. For interventions requiring responses, options for responding are preset in the system and presented in the user interface, along with the intervention message and content. Some interventions require a 'Yes' or 'No' response, such as those that ask a question (e.g. 'Have you set up an appointment?'), others require an 'OK' response, signifying acknowledgement that the interventions has been viewed and considered (e.g. 'Please talk to your pharmacist about food restrictions'), yet others require a text or number to be entered (e.g. 'What is your blood pressure today?'). Another type of intervention presents a number of items as a checklist in the user interface, and requires the user to select one or more of the items. Depending on the type of intervention, when the user enters or selects one or more of the response options, the system transitions the user to the next appropriate logical stage or process. For example, if the user responds with a 'Yes' to the 'Have you set up an appointment?' intervention, the system transition the user to the next logical stage to the user, namely, 'Please enter the appointment details'. If the user responds with a 'No', the system transitions the user to a different logical stage, namely, 'Please set up an appointment'. These transition rules comprise the rules for handling responses and are incorporated within the logic of the system, as shown in FIGS. 5C and 5D. In the case of an intervention with a checklist of options, the user may select one or more options and cause the system to transition the user to the next preset stage and to invoke multiple processes corresponding to each of the selected options. For example, a multiple checklist item stage might be as follows:

'Did the doctor:
[ ] ask you to come back for another visit?
[ ] give you any prescriptions?
[ ] ask you to take blood sugar readings?
[ ] ask you to get an eye exam?

The user can select any or all of these options. If the user selects the first option, the system transitions the user to the next stage which might be something like: 'Please set up an appointment' and the user would continue along a set of stages along the process of setting up and going for the next appointment. For the other options, each will invoke a separate process such as 'Filling or refilling prescriptions', 'Taking blood sugar readings', and 'Getting an eye exam', respectively. Each such invoked process has its own set of phases and stages, very much like a condition, and the system sends the respective interventions from each of these invoked processes following the same logic, and presents the current stages and interventions in the same user interface.

Content and Content Database

In the preferred embodiment, the system uses the web as the content database, retrieves content in real time, based on pre-configured search words, and dynamically displays the retrieved content links in the user interface. Search words are tied to specific condition-states and other attributes of the intervention such as 'learn more', 'how do I', 'why should I', 'ask your Doctor', and so on. These search words are transmitted to general search engines (e.g. Google, Yahoo, etc.), and the relevant content links are retrieved and displayed. The user can access any of the retrieved content by clicking on the displayed links. In this way, there is no need to maintain a database of content and there is greatly diminished need to maintain the freshness of the links, since they are all live links. In addition to retrieving content from general search engines, the system also retrieves similar content from 'certified' or 'trusted' sources such as WebMD or Mayo Clinic. Content from these sources has been vetted and verified by qualified medical professionals as opposed to content from general search engines which may or may not be verified in such a manner. Further, the content links can also be directed to a database of custom content, such as content relevant to a specific clinical trial that has been approved and released for trial participants. Another example might be product or program-specific content from pharmaceutical firms, employers or health plans.

As shown in FIG. 6, in another embodiment, the content database houses the raw information that is to be transmitted by an intervention. Content, in the form of test, graphics, photographs, audio, video, and other common formats are indexed and stored in the database. In some cases, external content may be imported and cached in the content database for quick, accurate and reliable access, especially for content from links that change over time.

All content, regardless of source, is stored in the content database and standard content management methods are used to maintain the freshness of the content.

Content Model

The content model characterizes each specific content item in terms of several elements: topic, disease, disease-state, stage of change, language, readability, demographic-appropriate, format and ranking. Individual content items are categorized in terms of these elements in order to facilitate selection for interventions. For example, a content item may be a highly rated (ranking) video (format) in English or Spanish (language) with subtitles (readability) of a young man (demographic-appropriate: age, gender) who has gone blind (disease-state) as a result of neglecting his diabetes (disease), that may be very compelling to a member in the (pre-contemplation) stage of change. The topic in this example would be disease sequelae.

The 'Topic' element indicates what the content item is about. The 'Disease' element indicates which disease(s) the content item is relevant to; there may be multiple diseases. The disease-state element refers to the state of the individual with respect to disease(s), and indicates the member's interests in the treatments or risk factors for specific diseases, which disease screenings the member has taken, participation in prevention and wellness programs, disease-state, interests, what symptoms the member has, which diseases the member has been diagnosed with, which of the diagnosed diseases the member is being treated for, family history of diseases, and the state of control of the diagnosed diseases. A personal health risk assessment may also be included. The 'Stage of Change' element has to do with the behavioral stage of the member with respect to a specific health behavior. There are five stages of change: pre-contemplation (in which the member is not even thinking about a behavioral change such as going in for screenings), contemplation (in which the member starts thinking about screenings), decision (in which the member decides to go in for a particular screening), action (in which the member actually goes in for the screening) and maintenance (in which the member goes in for ongoing screenings on a regular basis as recommended by medical guidelines). The 'Language' element specifies the language of the content (English, Spanish, French, etc.). The 'Readability' element is based on whether the content can be understood by someone with a grade 8 education or less. The 'Demographic-Appropriate' element specifies whether the content item is age-appropriate, gender-oriented or neutral, or has affinity to a specific ethnic or racial background, or is relevant to a certain socioeconomic status and so on. The idea is to categorize the content item in ways that enable the system to find the best suitable match to the member's own demographics.

Content items and variants of the same item may need to be stored in different formats in order to support multiple channels. Textual formats are useful for mail, email, and SMS transmission, but the SMS variant may be more condensed than the email version. Voice formats are useful for some people—the system can read the text and send it a landline phone. Similarly, for distribution via the internet using links, video and audio formats bring a lot of clarity. Content items are also ranked in terms of usefulness by members. Each content item includes a 5-point rating scheme on a scale of 1 to 5. Individual members enter the rating (at their option) to indicate whether the item was useful or not, and the aggregate score is used to rank the content item against other similar content items. In addition, content items also have variants representing different tones: negative polite, positive polite, bald, motivational, punitive and so on.

Portal

As shown in FIG. 15, in one embodiment, the portal acts on the personalized intervention plan, and serves specific interventions via the designated channel to the designated member at the appointed time. The personalized intervention plan specifies, for a particular member, the various interventions that are mandatory and supplementary, and includes member-specific parameters for each intervention such as the channel, timing, frequency, tone, format and so on. The portal also acts as the conduit from the member's personal page to all the internet resources such as links to content, online communities, messages, and so on. In addition, the portal provides a mechanism by which member web behavior and responses to measuring interventions are gathered.

The initial interface to the member from the portal is through the personal page which contains an ordered list of proposed interventions comprising the member's intervention plan. The member modifications to the interventions are recorded and stored in the member history database. At any time, the member can access the system via the portal and make further modifications to the inputs, profile or interventions. After the interventions are served to the member, the member's behavior is observed in terms of the response to the intervention and the content, and in terms of interaction with the portal, i.e., web behavior.

A member's web behavior indicates the level of engagement. A highly engaged member will access the system on a frequent basis, click on the links provided and respond to 'usefulness' ratings embedded in the content. A highly engaged member may also modify interventions more frequently than those who are disinterested or not comfortable with the user interface. Member engagement is also indicated by their participation on online communities—whether they merely visit occasionally or whether they actively participate in terms of entering questions, answering other's questions, act as mentors to others, and so on.

Member responses to interventions are also recorded as they indicate member engagement as well. Whether the member responds to interventions by carrying out the actions requested, including keying in numbers on a keypad, whether the member responds to the embedded content usefulness entry and whether the member does this on a consistent basis all have a bearing on the member's level of engagement. There responses are collected via the portal through multiple channels and recorded in the operational database where it is held for a short term and then stored in the member history database for the long term.

Methods to Capture Adherence Information

Adherence Tracking

Measurement interventions are used to capture adherence. A measurement intervention is typically in the form of a question to which the member is required to respond. If the SMS channel is used, a text message such as 'Did you take your morning medicine today?' would be followed by a prompt: "Please enter 1 for yes or 0 for no'. If the member responds as requested, with a 1 or 0, then the system interprets the entries as answers to the specific measurement intervention and records the measurement in the operational database. Other types of questions are also possible, requiring a number to be keyed in. An example would be an SMS text measuring intervention 'In the last 3 days how many doses did you miss?' followed by a prompt: 'Please enter a number using the keypad'. If the member responds to the intervention with a valid number (it cannot be greater then the total number of doses prescribed for the member), the system interprets the answer and records it in the operational database. In this embodiment, we are using this type of method known as a self-report, in which the individual directly answers the measuring interventions. In other embodiments, alternate ways of obtaining adherence data may be used. For example, medications may be dispensed in special containers instrumented with detection electronic circuitry that automatically transmit the time when the container was opened (the assumption is that the member actually consumed the drugs at the same time). These types of devices may be interfaced with the portal and adherence measurements may proceed automatically.

Member Databases

As shown in FIG. 2 and FIG. 3, in one embodiment, all the inputs and derived member factors are stored in secure member databases. This database is the source for the personalization and analytics.

Methods for Handling Non-Response

As shown in FIG. 16, in one embodiment the 'Time Stamp' algorithm determines the appointed time $T_0$ for a particular intervention and passes the command to the 'Open Intervention' algorithm that opens the particular intervention that is drawn from the intervention database. If the intervention is time-based, the algorithm records the time $T_0$; if the intervention is count-based, it records the zero count $N_0$; if the intervention is based on number of elapsed days, then the day count is zero'd. i.e., $D_0$. The 'Record & Send' algorithm stores the intervention record in the member history database and the portal then sends the intervention to the member. The 'Open Intervention' algorithm continues to monitor the elapsed time, count or days as applicable to the intervention. At the appointed time $T_1$, the system checks the operational database to see if there has been a response to the intervention. Similarly if the appointed count is $N_1$ or appointed days are $D_1$. If there has been a response, the intervention is closed. If there has been no response, the system invokes the escalation process.

Within the escalation process (see FIG. 17), there are different escalation procedures for different types of interventions. When there has been no response to an intervention at the first appointed time $T_1$, first appointed count $N_1$, or first appointed day $D_1$, depending on the type of the intervention. The appointed times $T_1, T_2, T_3, T_4$, appointed counts $N_1, N_2, N_3, N_4$, and appointed days $D_1, D_2, D_3, D_4$, are member specific parameters. The 'Open Intervention' algorithm calculates the elapsed time $(T-T_0)$, elapsed count $(N-N_0)$ and elapsed Days $(D-D_0)$, depending on the type of intervention. For a time-based intervention, when the elapsed time has exceeded the member parameter $T_2$, the tone of the intervention is escalated to positive, then to a 'bald' tone when it has exceeded the member parameter $T_3$, and finally, when it has exceeded the member parameter $T_4$, the caregiver is notified. As an example, a reminder intervention (time-based) may begin with a neutral 'It is time for your morning medicine' at $T_0$, then escalate the tone to a positive-polite 'If you haven't taken your morning medicine already, please take it now', then to a bald 'Please take your morning medicine now'. In a similar manner, for a count-based intervention, the number of times the intervention has been repeated $(N-N_0)$ is tracked; at $N_2$, the intervention is sent to the alternate phone provided by the member, at $N_3$, the intervention is sent to the alternate contact (provided by the member, and could be an online mentor), and at $N_4$, the caregiver is notified. Similarly, for day-based interventions, at $D_2, D_3$ and $D_4$ the escalation is to change the intervention frequency, notify the caregiver and notify the provider, respectively.

Interventions are also adapted based on member non-response. FIG. 26a describes one embodiment of the intervention adaptation model. In this embodiment, the underlying premise is if an intervention is working, it should be continued but interventions that have stopped working should be changed. The decision may be driven by the adherence slope, as shown in this figure, but other indicators such as the trend in adherence slope may also drive the decision. If the slope is greater than zero, or zero, the intervention is working and will not be changed. If the slope is less than zero, the intervention is not working and will be replaced or changed in some way. Mandatory interventions will not be deleted but the frequency or timing may be changed (see below), but supplementary interventions can be replaced entirely. There is a larger list of candidate supplementary interventions that are ranked in different categories (disease criticality, usefulness, etc.) from which the top few are selected to be initially served. Based on member response, the system will automatically eliminate interventions that are being ignored and replace them with other interventions that may be ranked lower in the different categories. FIG. 26b describes another embodiment in which the frequency of the intervention is adapted to suit the member's preferences. In this embodiment, the underlying premise is that if a member does not respond to interventions (such as adherence measurements) every time, then the interventions are too frequent and should be made less frequent. There are other reasons for not responding, but in this embodiment, non-response is the criterion. Interventions are initially served at the current frequency, typically bi-weekly. If the member responds to instances of an intervention more than 75 percent of the time, the frequency is deemed to be matched to the member's preferences and the intervention frequency is continued. If the member response is less than 75 percent of the time, the intervention frequency is reduced.

Analytics

As shown in FIG. 18, there are two major types of analytics, individual and aggregate. Member adherence data, stored in the member history database and other member inputs, stored in the member databases are inputs for the analytics. Individual analytics are performed on member-specific data that is de-identified but has pointers so that individual functions such as setting incentive payments for individual members may be performed. Aggregate analytics are performed on de-identified data without any pointers that can be used to trace the data back to any specific individual. Aggregate analytics are performed on data about groups of people in order to elicit group risk profiles, group improvements, drug consumptions, and so on.

Individual Analytics

Member profile updates: one of the key uses of the member web behavior and intervention response data is to refine and update the member's profile. Members' preferences and profiles change over time. For example a member may be in a pre-contemplation stage of change at some point and as a result of multiple influencing interventions, may move to a contemplation or even action stage of change in a few weeks. Another member may have some painful symptoms at one point in time which may be alleviated by taking pain killers, with the pain gone, the member's state of health will be different in a matter of days. Clearly, a member's profile changes over time and needs to be updated periodically or whenever a change is detected, so that further interventions are based on the current profile and not the older one.

Adherence Slope: with reference to FIG. 22 which describes the method by which the adherence slope is derived from one set of measurements that are responses to a question such as 'Have you taken your dose?' that requires a 'Yes or No' or '1 or 0' answer. The member history database contains the historical responses to this measurement, including the current value and the previous value. If the current value is a 'No' and the previous value is a 'Yes', the adherence slope is deemed to be less than zero. If the current value is a 'No' and the previous value is also a 'No', the adherence slope is deemed to be zero. If the current value is a 'Yes' and the previous value is either a 'Yes' or a 'No', the c adherence slope is deemed to be greater than zero. FIG. 23 describes the method by which the adherence slope is derived from a different set of measurements, namely, a question such as 'How many doses did you miss in the last D days?' that requires a numeric response, typically 0 to 9. The response is converted to a D-day adherence rate. The member history database contains the historical responses to this measurement and the calculated adherence rates. The rate is considered to be low if more than 50 percent of the doses are missed (typically three out of six doses in a 3-day period), medium if between 18 percent and 49 percent of the doses are missed (typically two out of six doses in a 3-day period), and high if only 17 percent or less of the doses are missed (typically one or none of the six doses in a 3-day period). If the current rate is low and the previous rate is low, medium or high, the adherence slope is deemed to be less than or equal to zero. If the current rate is medium and the previous rate is high or medium, the adherence slope is also deemed to be less than or equal to zero. If the current rate is medium and the previous rate is low, the adherence slope is deemed to be greater than zero. If the current rate is high and the previous rate is low, medium or high, the adherence slope is deemed to be greater than zero.

Credibility Score: FIG. 20 describes the process by which the credibility score is derived. This is done on a continuous basis, being triggered whenever new information is recorded in the member history database. The credibility score is used to adjust the self-reported adherence information to compensate for the known over-estimation bias in self-reports. One determinant of the credibility score is the level of member engagement, as indicated by the number of member responses to interventions. The source of data for this process is the member history database, from which the responses to interventions are evaluated. If there is no response, the item score is a −1, and if there is a response, the item score is a +1. The number of non-responses and the number of responses are summed to provide one component of the credibility score. Another component of the credibility score comes from the member web behavior, which also indicates the level of the member's engagement with the system at a user-interface level. The more engaged the member, in terms of clicking on the links provided, participating in online communities, and so on, the higher this component of the credibility score. A third component of the credibility score comes from the member's clinical information which typically resides in external databases held by providers and physicians and is imported into the integration database, assuming the required permissions and access rights are in place. The specific clinical data of interest are the key indicators of disease control, such as serum cholesterol levels, glycosylated hemoglobin for diabetics, and so on. Regardless of the member's adherence self-reports, the true test is whether the desired health outcomes are achieved. If a member's diseases are being controlled, the relevant disease indicators should be within normal ranges. If these indicators are not within normal ranges, the item score is a −1, and if they are within normal ranges, the item score is a +1. The item scores are summed and incorporated into the credibility score. The underlying assumption is that higher adherence, if self-reported by the member, should be reflected in the clinical results that are closer to normal values. There are situations where a particular drug, even if taken exactly as directed, may not produce the desired clinical results; these are treated as exceptions. The credibility score determines an adjustment factor, which is qualitatively set at high, medium or low, and the adjustment factor is used to reduce the self-reported adherence responses by 0, 25 or 50 percent, as an example. These are system parameters that can be set externally.

PurpleTeal Score: FIG. 25 shows the inputs to the Member PurpleTeal Score. The PurpleTeal score is a figure of merit that characterizes a member's overall health behavior, similar to a person's credit-rating. It is a combination of several scores: screening adherence, medication adherence, treatment adherence, credibility and wellness adherence, and indicators: stage of adherence, response to interventions, response to content, community participation, calendar utilization, function utilization, web behavior, self management, and other indicators included in 'Etc.'. The respective scores and indicators for a particular member are weighted, added and coded to yield the member's PurpleTeal score.

Predictive Analytics—Expected Adherence

The member profile may be used to more accurately predict and manage risk. In one embodiment, the member profile is used to predict the expected adherence behavior which in turn can then be used as a baseline against which future actual adherence behavior may be compared. For example, based on a member's age, gender and race, the vulnerability mapping algorithm predicts that the member is susceptible to certain diseases and automatically generates screening oriented interventions for these diseases. At the same time, the affordability mapping algorithm, based on the member's income, family size and other factors, predicts that the member will not go for the screening and automatically generates enabling interventions to ease the cost through sponsored free screening events. Thus, inherent in the different mapping algorithms are predictions of expected adherence behavior. These elements are combined to yield an expected adherence profile for each member.

Predictive Analytics—Probability of Hospitalization

In another embodiment, the system provides analytics that use patient adherence data as a leading indicator to improve disease management programs. Patient adherence is treated as another vital sign that is captured on a regular basis. When a particular patient stops taking medicines it is only a matter of time before health problems become serious enough to warrant medical attention. Thus adherence data can be useful in identifying which patients are likely to require medical attention if left unattended and disease management programs can proactively stratify risks. Additionally, such patients can be contacted and asked to resume their medications in an attempt to stave off unnecessary medical treatments.

Incentive Achievement Analytics

The system analyzes the database for adherence trends and history for individual patients. Subject to applicable privacy regulations, the trends and history may be provided to insurance companies, payers or managed-care organizations. These organizations may further use the information to structure incentives, such as rebates or premium adjustments, to improve the adherence performance of individual patients. This data may also be transmitted to providers for use in managing 'Pay-for-Performance' program incentives.

Aggregate Analytics

Drug Consumption Analytics: current supply chain management systems can only track drugs to the pharmacy level. Once the prescriptions are filled and taken from the pharmacy, it is difficult to track consumption. Adherence data collected from individual members is aggregated into drug specific consumption patterns and used to predict future drug requirements. This analytic is provided to pharmaceutical manufacturers, distributors and pharmacies to enable timely and accurate supply replenishment and production forecasting.

Employee population expected adherence risk profile: this is a consolidation of the individual expected adherence analytics. Using this analytic, employers and others can examines groups of people, estimate their risks of non-adherence and structure overall incentive programs to improve adherence.

Risk reserve projections: since adherence is a leading indicator of the level of utilization of expensive health services, the population adherence risk profile is used to estimate the heath expenditures on a more current basis. This can be done monthly or more frequently and the risk reserve monies can be adjusted on a more frequent basis. This improves the accuracy of the risk reserve projections.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A computer-implemented method comprising:
storing patient information about a particular patient;
storing medical condition information about one or more medical conditions;
wherein the one or more medical conditions includes a particular medical condition;
wherein the medical condition information for the particular medical condition comprises:
  phase information about one or more phases of the particular medical condition; and
  state information about one or more states of a particular phase of the one or more phases;
  each state, of the one or more states, being associated with a stored intervention message, wherein an intervention message comprises a message to be communicated to a patient about a particular action to be taken by the patient;
  state transition rules that are associated with a particular state of the particular phase of the particular medical condition;
  wherein the state transition rules include a particular state transition rule that specifies that a patient in a first state is to transition to a second state when the patient responds in a particular manner while in the first state;
determining, by one or more computing devices, that the first state is the current state of the particular patient by comparing said patient information with said state information;
in response to determining that the first state of said one or more states is the current state, associating, by the one or more computing devices, the particular patient with the first state;
in response to the particular patient being associated with the first state, selecting a first particular stored intervention message associated with the first state to be sent to the particular patient;
sending the first particular stored intervention message to the particular patient;
receiving a response to the sent first particular stored intervention message from the particular patient;
based, at least in part, on the received response and the particular state transition rule, associating the particular patient with a second state of said one or more states that is different from the first state, and causing the particular patient to no longer be associated with the first state;
in response to the particular patient being associated with the second state, selecting a second particular stored intervention message associated with the second state to be sent to the particular patient, wherein the second particular stored intervention message is different than the first particular stored intervention message;
sending the second particular intervention message to the particular patient.

2. The computer-implemented method of claim 1 further comprising:
determining that no response has been received to the second particular intervention message from the particular patient after waiting a predetermined amount of time; and
in response to determining that no response has been received to the second particular intervention message from the particular patient after waiting the predetermined amount of time, alerting a person that is not the particular patient about the lack of response from the particular patient.

3. The computer-implemented method of claim 1 further comprising:
in response to sending the first particular stored intervention message to the particular patient, retrieving search results related to the first state by executing a search using search strings associated with the first state; and
delivering said search results to the particular patient.

4. The computer-implemented method of claim 1 further comprising:
in response to sending the second particular stored intervention message to the particular patient, selecting a first piece of content related to the second state from a database storing pieces of content related to a plurality of states; and
sending the first piece of content to the particular patient.

5. The computer-implemented method of claim 4 further comprising:
associating one or more pieces of content of said pieces of content with urgency values indicating how likely the corresponding piece of content is to increase seriousness in a patient that would perceive the corresponding piece of content;
determining that no response has been received to the second particular intervention message from the particular patient after waiting a predetermined amount of time; and
in response to determining that no response has been received to the second particular intervention message from the particular patient after waiting the predetermined amount of time, selecting a second piece of content related to the second state from the database storing said pieces of content related to the plurality of states, wherein an urgency value of the second piece of content indicates that the second piece of content is more likely to increase seriousness in a patient that would perceive the second piece of content than the first piece of content.

6. The computer-implemented method of claim 4, wherein sending the first particular stored intervention message to the particular patient comprises sending the first particular stored intervention message through a particular channel of communication, wherein the particular channel of communication is selected from a set of channels of communications through which intervention messages may be sent associated with the first particular stored intervention message.

7. The computer-implemented method of claim 1, further comprising:
determining that no response has been received to the second particular intervention message from the particular patient after waiting a predetermined amount of time; and
in response to determining that no response has been received to the second particular intervention message from the particular patient after waiting the predetermined amount of time, selecting a second particular channel of communication from a set of channels of communications through which intervention messages may be sent associated with a third intervention message, based in part on said stored patient information; and sending the third intervention message to the particular patient through the selected second particular channel of communication.

8. The computer-implemented method of claim 1, wherein storing patient information about the particular patient further comprises:

importing information about the particular patient from particular databases;
gathering information from the particular patient;
identifying particular types of missing information; and
creating data of said particular types based on said imported information and said gathered information.

9. The computer-implemented method of claim 8, wherein gathering information from the particular patient comprises:

gathering desired intervention frequency information indicating how frequently the particular patient wishes to receive intervention messages;
calculating an intervention frequency value based on the desired intervention frequency information; and
storing said intervention frequency value.

10. The computer-implemented method of claim 9, further comprising:

determining that no response has been received to the second particular intervention message from the particular patient after waiting a predetermined amount of time; and
in response to determining that no response has been received to the second particular intervention message from the particular patient after waiting the predetermined amount of time, modifying said intervention frequency value to indicate that the particular patient is to be sent intervention messages more frequently than before said modification of the intervention frequency value.

11. The computer-implemented method of claim 1, further comprising:

assigning a credibility score to the particular patient;
storing said response to the sent first particular stored intervention message from the particular patient;
based on the assigned credibility score, modifying said response; and
storing said modified response.

12. The computer-implemented method of claim 11, wherein assigning a credibility score to the particular patient comprises:

calculating the credibility score by comparing a number of responses received by the particular patient to a number of times a pre-determined amount of time has passed without a response being received from the particular patient.

13. The computer-implemented method of claim 11, wherein assigning a credibility score to the particular patient further comprises:

accessing medical history data that comprises values indicating how well a particular disease has been controlled by the particular patient; and
determining the credibility score based on said values indicating how well the particular disease has been controlled by the particular patient.

14. A non-transitory computer-readable storage medium storing instructions, wherein the instructions, when executed by one or more processors cause:

storing patient information about a particular patient;
storing medical condition information about one or more medical conditions;
wherein the one or more medical conditions includes a particular medical condition;
wherein the medical condition information for the particular medical condition comprises:
phase information about one or more phases of the particular medical condition; and
state information about one or more states of a particular phase of the one or more phases;
each state, of the one or more states, being associated with a stored intervention message, wherein an intervention message comprises a message to be communicated to a patient about a particular action to be taken by the patient;
state transition rules that are associated with a particular state of the particular phase of the particular medical condition;
wherein the state transition rules include a particular state transition rule that specifies that a patient in a first state is to transition to a second state when the patient responds in a particular manner while in the first state;
determining that the first state is the current state of the particular patient by comparing said patient information with said state information;
in response to determining that the first state of said one or more states is the current state, associating the particular patient with the first state;
in response to the particular patient being associated with the first state, selecting a first particular stored intervention message associated with the first state to be sent to the particular patient;
sending the first particular stored intervention message to the particular patient;
receiving a response to the sent first particular stored intervention message from the particular patient;
based, at least in part, on the received response and the particular state transition rule, associating the particular patient with a second state of said one or more states that is different from the first state, and causing the particular patient to no longer be associated with the first state;
in response to the particular patient being associated with the second state, selecting a second particular stored intervention message associated with the second state to be sent to the particular patient, wherein the second particular stored intervention message is different than the first particular stored intervention message;
sending the second particular intervention message to the particular patient.

15. The non-transitory computer-readable storage medium of claim 14, wherein the instructions, when executed by one or more processors, further cause:

determining that no response has been received to the second particular intervention message from the particular patient after waiting a predetermined amount of time; and
in response to determining that no response has been received to the second particular intervention message from the particular patient after waiting the predetermined amount of time, alerting a person that is not the particular patient about the lack of response from the particular patient.

16. The non-transitory computer-readable storage medium of claim 14, wherein the instructions, when executed by one or more processors, further cause:
in response to sending the first particular stored intervention message to the particular patient, retrieving search results related to the first state by executing a search using search strings associated with the first state; and
delivering said search results to the particular patient.

17. The non-transitory computer-readable storage medium of claim 14, wherein the instructions, when executed by one or more processors, further cause:
in response to sending the second particular stored intervention message to the particular patient, selecting a first piece of content related to the second state from a database storing pieces of content related to a plurality of states; and
sending the first piece of content to the particular patient.

18. The non-transitory computer-readable storage medium of claim 17, wherein the instructions, when executed by one or more processors, further cause:
associating one or more pieces of content of said pieces of content with urgency values indicating how likely the corresponding piece of content is to increase seriousness in a patient that would perceive the corresponding piece of content;
determining that no response has been received to the second particular intervention message from the particular patient after waiting a predetermined amount of time; and
in response to determining that no response has been received to the second particular intervention message from the particular patient after waiting the predetermined amount of time, selecting a second piece of content related to the second state from the database storing said pieces of content related to the plurality of states, wherein an urgency value of the second piece of content indicates that the second piece of content is more likely to increase seriousness in a patient that would perceive the second piece of content than the first piece of content.

19. The non-transitory computer-readable storage medium of claim 17, wherein sending the first particular stored intervention message to the particular patient comprises sending the first particular stored intervention message through a particular channel of communication, wherein the particular channel of communication is selected from a set of channels of communications through which intervention messages may be sent associated with the first particular stored intervention message.

20. The non-transitory computer-readable storage medium of claim 14, wherein the instructions, when executed by one or more processors, further cause:
determining that no response has been received to the second particular intervention message from the particular patient after waiting a predetermined amount of time; and
in response to determining that no response has been received to the second particular intervention message from the particular patient after waiting the predetermined amount of time, selecting a second particular channel of communication from a set of channels of communications through which intervention messages may be sent associated with a third intervention message, based in part on said stored patient information; and
sending the third intervention message to the particular patient through the selected second particular channel of communication.

21. The non-transitory computer-readable storage medium of claim 14, wherein the instructions, when executed by one or more processors, further cause:
importing information about the particular patient from particular databases;
gathering information from the particular patient;
identifying particular types of missing information; and
creating data of said particular types based on said imported information and said gathered information.

22. The non-transitory computer-readable storage medium of claim 21, wherein gathering information from the particular patient comprises:
gathering desired intervention frequency information indicating how frequently the particular patient wishes to receive intervention messages;
calculating an intervention frequency value based on the desired intervention frequency information; and
storing said intervention frequency value.

23. The non-transitory computer-readable storage medium of claim 22, wherein the instructions, when executed by one or more processors, further cause:
determining that no response has been received to the second particular intervention message from the particular patient after waiting a predetermined amount of time; and
in response to determining that no response has been received to the second particular intervention message from the particular patient after waiting the predetermined amount of time, modifying said intervention frequency value to indicate that the particular patient is to be sent intervention messages more frequently than before said modification of the intervention frequency value.

24. The non-transitory computer-readable storage medium of claim 14, wherein the instructions, when executed by one or more processors, further cause:
assigning a credibility score to the particular patient;
storing said response to the sent first particular stored intervention message from the particular patient;
based on the assigned credibility score, modifying said response; and
storing said modified response.

25. The non-transitory computer-readable storage medium of claim 24, wherein assigning a credibility score to the particular patient comprises:
calculating the credibility score by comparing a number of responses received by the particular patient to a number of times a pre-determined amount of time has passed without a response being received from the particular patient.

26. The non-transitory computer-readable storage medium of claim 24, wherein assigning a credibility score to the particular patient comprises:
accessing medical history data that comprises values indicating how well a particular disease has been controlled by the particular patient; and
determining the credibility score based on said values indicating how well the particular disease has been controlled by the particular patient.

* * * * *